United States Patent
Cai et al.

(10) Patent No.: US 11,208,483 B2
(45) Date of Patent: *Dec. 28, 2021

(54) CTLA-4 ANTIBODIES AND USES THEREOF

(71) Applicant: Shanghai Kanda Biotechnology Co. Ltd, Shanghai (CN)

(72) Inventors: Zeling Cai, Shanghai (CN); Yi Chen, Shanghai (CN)

(73) Assignee: Shanghai Kanda Biotechnology Co, Ltd., Shanghai (CN)

( * ) Notice: Subject to any disclaimer, the term of this patent is extended or adjusted under 35 U.S.C. 154(b) by 23 days.

This patent is subject to a terminal disclaimer.

(21) Appl. No.: 15/777,369

(22) PCT Filed: Nov. 19, 2015

(86) PCT No.: PCT/CN2015/095072
§ 371 (c)(1),
(2) Date: May 18, 2018

(87) PCT Pub. No.: WO2017/084078
PCT Pub. Date: May 26, 2017

(65) Prior Publication Data
US 2020/0262921 A1 Aug. 20, 2020

(51) Int. Cl.
| | | |
|---|---|---|
| *C07K 16/28* | (2006.01) | |
| *A61K 39/00* | (2006.01) | |
| *A61K 39/29* | (2006.01) | |
| *A61K 39/395* | (2006.01) | |

(52) U.S. Cl.
CPC .. *C07K 16/2818* (2013.01); *A61K 39/001139* (2018.08); *A61K 39/292* (2013.01); *A61K 39/3955* (2013.01); *C07K 2317/565* (2013.01); *C07K 2317/622* (2013.01); *C07K 2317/76* (2013.01); *C07K 2317/92* (2013.01)

(58) Field of Classification Search
CPC ................................................ C07K 16/2818
See application file for complete search history.

(56) References Cited

U.S. PATENT DOCUMENTS

| | | | |
|---|---|---|---|
| 6,984,720 B1 * | 1/2006 | Korman | A61P 31/10 530/388.22 |
| 11,021,538 B2 * | 6/2021 | Cai | C07K 16/3069 |
| 2019/0048080 A1 * | 2/2019 | Cai | C12N 15/85 |

FOREIGN PATENT DOCUMENTS

| | | |
|---|---|---|
| CN | 104292334 A | 1/2015 |
| WO | 2012/120125 | 9/2012 |

OTHER PUBLICATIONS

Chin et al., Chang Gung Med J 2008; 31:1-15 (Year: 2008).*
Blank & Enk, Int'l Immunol (2014) 27:3-10 (Year: 2014).*
Bartolazzi et al., The Lancet 2008; 9:543-49 (Year: 2008).*
Written Opinion for Application No. PCT/CN2015/095072, dated Aug. 2, 2016.
International Preliminary Report on Patentability for Application No. PCT/CN2015/095072, dated May 31, 2018.
Pistillo et al., Molecular characterization and applications of recombinant scFv antibodies to CD152 co-stimulatory molecule. Tissue Antigens. Mar. 2000;55(3):229-38.
GenBank: X62959.1. Database NCBI. Jun. 2, 1992. Raaphorst, F.M. et.al.
GenBank: L25295.1. Database NCBI. May 4, 2000. Harindranath, N. et.al.
GenBank: AF062193.1. Database NCBI May 8, 2001. Wang, X. et.al.
GenBank: AB063931.1. Database NCBI Jul. 2, 2002. Akahori, Y. et.al.
GenBank: Z47230.1. Database NCBI Sep. 9, 2004. Demaison, C. et.al.
GenBank: AAX56332.1. Database NCBI Feb. 13, 2008. Chin, L.T. et.al.
GenBank: AAX56333.1. Database NCBI Feb. 13, 2008. Chin, L.T. et.al.

* cited by examiner

*Primary Examiner* — Jessica H Roark
(74) *Attorney, Agent, or Firm* — Wolf, Greenfield & Sacks, P.C.

(57) ABSTRACT

Human antibodies which specifically bind to human CTLA-4, and related antibody-based compositions and molecules, are disclosed. Also disclosed are pharmaceutical compositions comprising the human antibodies, and therapeutic and diagnostic methods for using the human antibodies.

20 Claims, 24 Drawing Sheets

Specification includes a Sequence Listing.

FIG. 2A

```
              10         20         30         40         50         60
C2    CAGGTCCAGCTGGTGCAGTCTGGGGGAGGCGTGGTCCAGCCTGGGAGGTCCCTGAGACTC
C4    CAGGTCCAGCTGGTGCAGTCTGGGGGAGGCGTGGTCCAGCCTGGGAGGTCCCTGAGACTC
C10   CAGGTCCAGCTGGTGCAGTCTGGGGGAGGCGTGGTCCAGCCTGGGAGGTCCCTGAGACTC
C11   CAGGTCCAGCTGGTGCAGTCTGGGGGAGGCGTGGTCCAGCCTGGGAGGTCCCTGAGACTC
C12   CAGGTCCAGCTGGTGCAGTCTGGGGGAGGCGTGGTCCAGCCTGGGAGGTCCCTGAGACTC
C13   CAGGTCCAGCTGGTGCAGTCTGGGGGAGGCGTGGTCCAGCCTGGGAGGTCCCTGAGACTC
      ************************************************************
              70         80         90        100        110        120
C2    TCCTGTGCAGCGTCTGGATTCACCTTCAGTAGCTATGGCATGCACTGGGTCCGCCAGGCT
C4    TCCTGTGCAGCGTCTGGATTCACCTTCAGTAGCTATGGCATGCACTGGGTCCGCCAGGCT
C10   TCCTGTGCAGCGTCTGGATTCACCTTCAGTAGCTATGGCATGCACTGGGTCCGCCAGGCT
C10   TCCTGTGCAGCGTCTGGATTCACCTTCAGTAGCTATGGCATGCACTGGGTCCGCCAGGCT
C12   TCCTGTGCAGCGTCTGGATTCACCTTCAGTAGCTATGGCATGCACTGGGTCCGCCAGGCT
C13   TCCTGTGCAGCGTCTGGATTCACCTTCAGTAGCTATGGCATGCACTGGGTCCGCCAGGCT
      ************************************************************
             130        140        150        160        170        180
C2    CCAGGCAAGGGGCTGGAGTGGGTGGCAGTTATATGGTATGATGGAAGTAGGCAATATTAT
C4    CCAGGCAAGGGGCTGGAGTGGGTGGCAGTTATATGGTATGATGGAAGTAGGCAATATTAT
C10   CCAGGCAAGGGGCTGGAGTGGGTGGCAGTTATATGGTATGATGGAAGTAGGCAATATTAT
C11   CCAGGCAAGGGGCTGGAGTGGGTGGCAGTTATATGGTATGATGGAAGTAGGCAATATTAT
C12   CCAGGCAAGGGGCTGGAGTGGGTGGCAGTTATATGGTATGATGGAAGTAGGCAATATTAT
C13   CCAGGCAAGGGGCTGGAGTGGGTGGCAGTTATATGGTATGATGGAAGTAGGCAATATTAT
      ************************************************************
             190        200        210        220        230        240
C2    GCTGACTCCGTGAAGGGCCGATTCACCATCTCCAGAGACGATTCCAAGAACACGATGTAT
C4    GCTGACTCCGTGAAGGGCCGATTCACCATCTCCAGAGACGATTCCAAGAACACGATGTAT
C10   GCTGACTCCGTGAAGGGCCGATTCACCATCTCCAGAGACGATTCCAAGAACACGATGTAT
C11   GCTGACTCCGTGAAGGGCCGATTCACCATCTCCAGAGACGATTCCAAGAACACGATGTAT
C12   GCTGACTCCGTGAAGGGCCGATTCACCATCTCCAGAGACGATTCCAAGAACACGATGTAT
C13   GCTGACTCCGTGAAGGGCCGATTCACCATCTCCAGAGACGATTCCAAGAACACGATGTAT
      ************************************************************
             250        260        270        280        290        300
C2    CTGCAAATGAACAGCCTGAGAGCCGAAGACACGGCTGTTTATTACTGTGCGAGAGGGGGA
C4    CTGCAAATGAACAGCCTGAGAGCCGAAGACACGGCTGTTTATTACTGTGCGAGAGGGGGA
C10   CTGCAAATGAACAGCCTGAGAGCCGAAGACACGGCTGTTTATTACTGTGCGAGAGGGGGA
C11   CTGCAAATGAACAGCCTGAGAGCCGAAGACACGGCTGTTTATTACTGTGCGAGAGGGGGA
C12   CTGCAAATGAACAGCCTGAGAGCCGAAGACACGGCTGTTTATTACTGTGCGAGAGGGGGA
C13   CTGCAAATGAACAGCCTGAGAGCCGAAGACACGGCTGTTTATTACTGTGCGAGAGGGGGA
      ************************************************************
             310        320        330        340        350
C2    TTTTGGGGGGCTTTTGATATCTGGGGCCAAGGGACAATGGTCACCGTCTCCTCA
C4    TTTTGGGGGGCTTTTGATATCTGGGGCCAAGGGACAATGGTCACCGTCTCCTCA
C10   TTTTGGGGGGCTTTTGATATCTGGGGCCAAGGGACAATGGTCACCGTCTCCTCA
C11   TTTTGGGGGGCTTTTGATATCTGGGGCCAAGGGACAATGGTCACCGTCTCCTCA
C12   TTTTGGGGGGCTTTTGATATCTGGGGCCAAGGGACAATGGTCACCGTCTCCTCA
C13   TTTTGGGGGGCTTTTGATATCTGGGGCCAAGGGACAATGGTCACCGTCTCCTCA
      ******************************************************
```

FIG.2B

```
              10        20        30        40        50        60
C2    GATGTTGTGATGACTCAGTCTCCAGGCACCCTGTCTTTGTCTCCAGGGGAAGGAGCCACA
C4    GATGTTGTGATGACTCAGTCTCCAGGCACCCTGTCTTTGTCTCCAGGGGAAGGAGCCACA
C10   GATGTTGTGATGACTCAGTCTCCAGGCACCCTGTCTTTGTCTCCAGGGGAAGGAGCCACA
C11   GATGTTGTGATGACTCAGTCTCCAGGCACCCTGTCTTTGTCTCCAGGGGAAGGAGCCACA
C12   GATGTTGTGATGACTCAGTCTCCAGGCACCCTGTCTTTGTCTCCAGGGGAAGGAGCCACA
C13   GATGTTGTGATGACTCAGTCTCCAGGCACCCTGTCTTTGTCTCCAGGGGAAGGAGCCACA
      ************************************************************
              70        80        90       100       110       120
C2    CTCTCCTGCAGGGCCAGTCAACATGTTATCAGCAGCTACTTAGCCTGGTATCAGCAAAAA
C4    CTCTCCTGCAGGGCCAGTCAACATGTTATCAGCAGCTACTTAGCCTGGTATCAGCAAAAA
C10   CTCTCCTGCAGGGCCAGTCAACATGTTATCAGCAGCTACTTAGCCTGGTATCAGCAAAAA
C11   CTCTCCTGCAGGGCCAGTCAACATGTTATCAGCAGCTACTTAGCCTGGTATCAGCAAAAA
C12   CTCTCCTGCAGGGCCAGTCAACATGTTATCAGCAGCTACTTAGCCTGGTATCAGCAAAAA
C13   CTCTCCTGCAGGGCCAGTCAACATGTTATCAGCAGCTACTTAGCCTGGTATCAGCAAAAA
      ************************************************************
             130       140       150       160       170       180
C2    CCTGGCCAGGCTCCCAGGCTCCTCGTCTACGGTGCATCCAGTAGGGACACTGGCGTCTCA
C4    CCTGGCCAGGCTCCCAGGCTCCTCGTCTACGGTGCATCCAGTAGGGACACTGGCGTCTCA
C10   CCTGGCCAGGCTCCCAGGCTCCTCGTCTACGGTGCATCCAGTAGGGACACTGGCGTCTCA
C11   CCTGGCCAGGCTCCCAGGCTCCTCGTCTACGGTGCATCCAGTAGGGACACTGGCGTCTCA
C12   CCTGGCCAGGCTCCCAGGCTCCTCGTCTACGGTGCATCCAGTAGGGACACTGGCGTCTCA
C13   CCTGGCCAGGCTCCCAGGCTCCTCGTCTACGGTGCATCCAGTAGGGACACTGGCGTCTCA
      ************************************************************
             190       200       210       220       230       240
C2    GACAGGTTCACTGGCAGTGGGTCTGGGACAGACTTCACTCTCACCATCAGCAGACTGGAG
C4    GACAGGTTCACTGGCAGTGGGTCTGGGACAGACTTCACTCTCACCATCAGCAGACTGGAG
C10   GACAGGTTCACTGGCAGTGGGTCTGGGACAGACTTCACTCTCACCATCAGCAGACTGGAG
C11   GACAGGTTCACTGGCAGTGGGTCTGGGACAGACTTCACTCTCACCATCAGCAGACTGGAG
C12   GACAGGTTCACTGGCAGTGGGTCTGGGACAGACTTCACTCTCACCATCAGCAGACTGGAG
C13   GACAGGTTCACTGGCAGTGGGTCTGGGACAGACTTCACTCTCACCATCAGCAGACTGGAG
      ************************************************************
             250       260       270       280       290       300
C2    CCTGAAGATTCTGCGGTGTATTTCTGTCAGCAGTATGGTACATCACCGTGGACGTTCGGC
C4    CCTGAAGATTCTGCGGTGTATTTCTGTCAGCAGTATGGTACATCACCGTGGACGTTCGGC
C10   CCTGAAGATTCTGCGGTGTATTTCTGTCAGCAGTATGGTACATCACCGTGGACGTTCGGC
C11   CCTGAAGATTCTGCGGTGTATTTCTGTCAGCAGTATGGTACATCACCGTGGACGTTCGGC
C12   CCTGAAGATTCTGCGGTGTATTTCTGTCAGCAGTATGGTACATCACCGTGGACGTTCGGC
C13   CCTGAAGATTCTGCGGTGTATTTCTGTCAGCAGTATGGTACATCACCGTGGACGTTCGGC
      ************************************************************
             310       320
C2    CAAGGGACCAAGCTGGAGATCAAACGT
C4    CAAGGGACCAAGCTGGAGATCAAACGT
C10   CAAGGGACCAAGCTGGAGATCAAACGT
C11   CAAGGGACCAAGCTGGAGATCAAACGT
C12   CAAGGGACCAAGCTGGAGATCAAACGT
C13   CAAGGGACCAAGCTGGAGATCAAACGT
      ***************************
```

FIG. 3A

```
              10         20         30         40         50         60
C6    CAGGTGCAGCTGGTGCAGTCCGGGGCTGAGGTGAAGAAGCCTGGGTCCTCGGTGAAGGTC
C7    CAGGTGCAGCTGGTGCAGTCCGGGGCTGAGGTGAAGAAGCCTGGGTCCTCGGTGAAGGTC
C15   CAGGTGCAGCTGGTGCAGTCCGGGGCTGAGGTGAAGAAGCCTGGGTCCTCGGTGAAGGTC
      ************************************************************
              70         80         90        100        110        120
C6    TCCTGCAAGGCTTCTGGAGGCACCTTCAGCAGCTATGCTATCAGCTGGGTGCGACAGGCC
C7    TCCTGCAAGGCTTCTGGAGGCACCTTCAGCAGCTATGCTATCAGCTGGGTGCGACAGGCC
C15   TCCTGCAAGGCTTCTGGAGGCACCTTCAGCAGCTATGCTATCAGCTGGGTGCGACAGGCC
      ************************************************************
             130        140        150        160        170        180
C6    CCTGGACAAGGGCTTGAGTGGATGGGAGGGATCATCCCTATCTTTGGTACAGCAAACTAC
C7    CCTGGACAAGGGCTTGAGTGGATGGGAGGGATCATCCCTATCTTTGGTACAGCAAACTAC
C15   CCTGGACAAGGGCTTGAGTGGATGGGAGGGATCATCCCTATCTTTGGTACAGCAAACTAC
      ************************************************************
             190        200        210        220        230        240
C6    GCACAGAAGTTCCAGGGCAGAGTCACGATTACCGCGGACGAATCCACGAGCACAGCCTAC
C7    GCACAGAAGTTCCAGGGCAGAGTCACGATTACCGCGGACGAATCCACGAGCACAGCCTAC
C15   GCACAGAAGTTCCAGGGCAGAGTCACGATTACCGCGGACGAATCCACGAGCACAGCCTAC
      ************************************************************
             250        260        270        280        290        300
C6    ATGGAGCTGAGCAGCCTGAGATCTGAGGACACGGCCGTGTATTACTGTGCGAGAGATACT
C7    ATGGAGCTGAGCAGCCTGAGATCTGAGGACACGGCCGTGTATTACTGTGCGAGAGATACT
C15   ATGGAGCTGAGCAGCCTGAGATCTGAGGACACGGCCGTGTATTACTGTGCGAGAGATACT
      ************************************************************
             310        320        330        340        350        360
C6    GCTATGGCACTATTCTACTACTACTACGGTATGGACGTCTGGGGCCAAGGCACCCTGGTC
C7    GCTATGGCACTATTCTACTACTACTACGGTATGGACGTCTGGGGCCAAGGCACCCTGGTC
C15   GCTATGGCACTATTCTACTACTACTACGGTATGGACGTCTGGGGCCAAGGCACCCTGGTC
      ************************************************************
             370
C6    ACCGTCTCCTCA
C7    ACCGTCTCCTCA
C15   ACCGTCTCCTCA
      ************
```

FIG.3B

```
             10         20         30         40         50         60
C6   CAGTCTGCCCTGACTCAGCCTGCCTCCGTGTCTGGGTCTCCTGGACAGTCGACCACCATC
C7   CAGTCTGCCCTGACTCAGCCTGCCTCCGTGTCTGGGTCTCCTGGACAGTCGACCACCATC
C15  CAGTCTGCCCTGACTCAGCCTGCCTCCGTGTCTGGGTCTCCTGGACAGTCGACCACCATC
     ************************************************************
             70         80         90        100        110        120
C6   TCCTGCACTGGAACCAGCAGTGACGTTGGTGGTTATAACTATGTCTCCTGGTACCAACAG
C7   TCCTGCACTGGAACCAGCAGTGACGTTGGTGGTTATAACTATGTCTCCTGGTACCAACAG
C15  TCCTGCACTGGAACCAGCAGTGACGTTGGTGGTTATAACTATGTCTCCTGGTACCAACAG
     ************************************************************
            130        140        150        160        170        180
C6   CACCCAGGCAAAGCCCCCAAACTCATGATTTATGAGGTCAGTAATCGGCCCTCAGGGGTT
C7   CACCCAGGCAAAGCCCCCAAACTCATGATTTATGAGGTCAGTAATCGGCCCTCAGGGGTT
C15  CACCCAGGCAAAGCCCCCAAACTCATGATTTATGAGGTCAGTAATCGGCCCTCAGGGGTT
     ************************************************************
            190        200        210        220        230        240
C6   TCTAATCGCTTCTCTGGCTCCAAGTCTGGCAACACGGCCTCCCTGACCATCTCTGGGCTC
C7   TCTAATCGCTTCTCTGGCTCCAAGTCTGGCAACACGGCCTCCCTGACCATCTCTGGGCTC
C15  TCTAATCGCTTCTCTGGCTCCAAGTCTGGCAACACGGCCTCCCTGACCATCTCTGGGCTC
     ************************************************************
            250        260        270        280        290        300
C6   CAGGCTGAGGACGAGGCTGATTATTACTGCAGCTCATATAGAAGCAGCGGCACTCCTTAT
C7   CAGGCTGAGGACGAGGCTGATTATTACTGCAGCTCATATAGAAGCAGCGGCACTCCTTAT
C15  CAGGCTGAGGACGAGGCTGATTATTACTGCAGCTCATATAGAAGCAGCGGCACTCCTTAT
     ************************************************************
            310        320        330
C6   GTCTTCGGAACTGGGACCAAGCTGACCGTCCTAGGT
C7   GTCTTCGGAACTGGGACCAAGCTGACCGTCCTAGGT
C15  GTCTTCGGAACTGGGACCAAGCTGACCGTCCTAGGT
     ************************************
```

FIG. 4A

SEQ ID NO: 7 AND 72 (respectively)

HV3-33

```
Germline   CAG GTGCAG CTG GTG GAG TCT GGG GGA GGC GTG GTC CAG CCT GGG AGG TCC CTG AGA CTC TCC TGT GCA GCG
C2         --- ---C-- --- --- --- --- --- --- --- --- --- --- --- --- --- --- --- --- --- --- --- ---

CDR1
Germline   TCT GGA TTC ACC TTC AGT AGC TAT GGC ATG CAC TGG GTC CGC CAG GCT CCA GGC AAG GGG CTG GAG TGG GTG
C2         --- --- --- --- --- --- --- --- --- --- --- --- --- --- --- --- --- --- --- --- --- --- ---

CDR2
Germline   GCA GTT ATA TGG TAT GAT GGA AGT AAT AAA TAC TAT GCA GAC TCC GTG AAG GGC CGA TTC ACC ATC TCC AGA
C2         --- --- --- --- --- --- --- --- -GGC --- --- --T --- --- --- --- --- --- --- --- --- --- ---

Germline   GAC AAT TCC AAG AAC ACG CTG TAT CTG CAA ATG AAC AGC CTG AGA GCC GAG GAC ACG GCT GTG TAT TAC TGT
C2         --- G--- --- --- --- --- --- --- --- A-- --- --- --- --- --- ---A --- --- --- --- ---T --- ---

CDR3
           Jh3
Germline   GCG AGA
D3-16
C2         --- --- GGG GGA TTT TGG GGG GCT TTT GAT ATC TGG GGC CAA GGG ACA ATG GTC ACC GTC TCC TCA
```

FIG. 4B

SEQ ID NO: 9 AND 14 (respectively)

HV1-46

```
              CDR1
Germline  CAG GTG CAG CTG GTG CAG TCT GGG GCT GAG GTG AAG AAG CCT GGG TCA GTG AAG GTT TCC TGC AAG GCA TCT
C2        --- --- --- --- --- --A --- --- --- --- --- --- --- --- --- --- --- --- --- --- --- --- --- ---

CDR2
Germline  GGA TAC ACC TTC ACC AGC TAC TAT ATG CAC TGG GTG CGA CAG GCC CCT GGA CAA GGG CTT GAG TGG ATG GGA ATA
C2        --- -T- -GT --- --- -A- --- --C --- --- --- --- --- --- --- --- --- --- --- --- --- --- --- --- ---

Germline  ATA ATC AAC CCT AGT GGT GGT AGC ACA AGC TAC GCA CAG AAG TTC CAG GGC AGA GTC ACG ATG ACC AGG GAC ACG TCC
C2        --- -G- --- -CC --- --- --- --- -G- --- --- --- --- --- --- --- --- --- --- --- -A- --- --- --- ---

CDR3
Germline  ACG AGC ACA GTC TAC ATG GAG CTG AGC AGC CTG AGA TCT GAG GAC ACG GCC GTG TAT TAC TGT GCG AGA
C2        --- --- --- --- --- --T --- --- --- --- --- --- --- --- --- --- --- -C- --- --- --- --- ---

D1-1          J6
Germline  TAC AAC TGG AAC GGA GTT TGG GGT TAC GGT ATG GAC GTC TGG GGC CAA GGA ACC CTG GTC ACC GTC TCC TCA
C2
```

FIG. 4C

SEQ ID NO 11 AND 16 (respectively)

SEQ ID NO: 1 AND 13 (respectively)

VK3-20

```
              CDR1
Germline  GAA ATT GTG TTG ACG CAG TCT CCA GGC ACC CTG TCT TTG TCT CCA GGG GAA AGA GCC ACC CTC TCC TGC
C2        --T G-- --- A-- --T --- --- --- --- --- --- --- --- --- --- --- --- G-- --- --A --- ---

Germline  AGG GCC AGT CAG AGT GTT AGT AGC AGC TAC TTA GCC TGG TAC CAG CAG AAA CCT GGC CAG GCT CCC AGG
C2        --A CA- --- --- --- --- -T- --- --- --- --- --- --- --- --- --A --- --- --- --- --- ---
                                        CDR2
Germline  CTC CTC ATC TAT GGT GCA TCC AGC AGG GCC ACT GGC ATC CCA ... GAC AGG TTC AGT GGC
C2        --- --- --- G-- --C --- --- -T- --- --- --- G-- T-- ... --C --- --- --- ---

Germline  AGT GGG TCT GGG ACA GAC TTC ACT CTC ACC ATC AGC AGA CTG GAG CCT GAA GAT TTT GCA GTG TAT TAC TGT
C2        --- --- --- --- --- --- --- --- --- --- --- --- --- --- --- --- -C- --G --- --- -T- ---
                 CDR3          Jk1
Germline  CAG CAG TAT GGT AGC TCA CCG TGG ACG TTC GGC CAA GGG ACC AAG CTG GAG ATC AAA CGT
C2        --- --- --- --- --- -CA --- --- --- --- --- --- --- --- --- --- --- --- --- ---
```

FIG. 5B

SEQ ID NO. 3 AND 15 (respectively)

VL2-23

```
              CAG TCT GCC CTG ACT CAG CCT GCC TCC GTG TCT GGG TCT CCT GGA CAG TCG ATC ACC ATC TCC TGC ACT GGA ACC
Germline      --- --- --- --- --- --- T-- --- --- --- --- --- --- --- --- --- --- --- --- --- --- --- --- --- ---
C2            --- --- --- --- --- --- --- --- --- --- --- --- --- --- --- --- --- --- --- --- --- --- --- --- ---

CDR1
              AAC AGT GAT GTT GGG AGT TAT AAC CTT GTC TCC TGG TAC CAA CAG CAC CCA AAA GGC AAA GCC CTC ATG ATT
Germline      -G- --- --- --- -A- GG- --- --- --- -C- --- --- G-- --- --- -A- --- --- -A- -G T-- --- --- G-- -T- C-A
C2            --- --- --- --- --- --- --- --- --- --- --- --- --- --- --- --- --- --- --- --- --- --- --- --- ---

CDR2
              TAT GAG GGT AGT AAG CGG TCA GGG GTT TCT AAT CGC TTC TCT GGC TCC AAG TCT GGC AAC ACG GGC TCC CTG
Germline      --- --- -C AA- TA- --- --- -A --- --- G-- --- --- --- --- -C- --- -T- --- -A --- --- --- --- ---
C2            --- --- --- --- --- --- --- --- --- --- --- --- --- --- --- --- --- --- --- --- --- --- --- --- ---

CDR3
                                                                                                      J-2
              ACA ATC TCT GGG CTC CAG GCT GAG GAC GAG GCT GAT TAT TAC TGC TCA TGG TCA TAT AGT AGC TCT ACC TGG ATC
Germline      --C --T --- --- -C --- --- --- --- -A --- --- --- T-- --- --- --- --- --- --- -T- TC- ACC TGG ATC
C2            --- --- --- --- --- --- --- --- --- --- --- --- --- --- --- --- --- --- --- --- --- --- --- --- ---

Germline
C2            TTC GGC GGA GGG ACC CAG CTC ACC GTT TTA GGT
```

FIG. 5C

SEQ ID NO: 5 AND 17 (respectively)

VL2-14

```
                 CAG TCT GTC CTG ACT CAG CCT GCC TCC GTG TCT GGG TCT CCT GGA CAG TCG ATC ACC ATC TCC TGC ACT GGA ACC
Germline
C2               --- --- --- --- --- --- --- --- --- --- --- --- --- --- --- --- --- -T- --- --- --- --- --- --- ---

CDR1
                 AGC AGT GAC GTT GGT TAT AAC TAT GTC TGG TAC CAA CAG CAC CCA GGC AAA GCC CCC AAA CTC ATG
Germline
C2               --- --- --- --- --- --- --- --- --- --- --- --- --- --- --- --- --- --- --- --- --- --- ---

CDR2
                 TAT GAG GTC AGT AAT CGG CCC TCA GGG GTT TCT AAT CGC TTC TCT GGC TCC AAG TCT GGC AAC ACG GCC TCC CTG
Germline
C2               --- --- --- --- --- --- --- --- --- --- --- --- --- --- --- --- --- --- --- --- --- --- --- --- ---

ACC ATC TCT GGG CTC CAG GCT GAG GAC GAG GCT GAT TAT TAC TGC AGT TCA TAT ACA AGC AGC AGC
                                                                           CDR3
                                                                             L_1
Germline
C2               --- --- --- --- --- --- --- --- --- --- --- --- --- --- -C- G-- G-- A-T CCT TNT GTC TTC GGA ACT GGG ACC AAG CTG ACC GTC CTA GGT
Germline
C2
```

Figure 6

SEQ ID NO: 8 AND 18 (respectively)

```
                                           CDR1                          CDR2
HV3-33
Germline      QVQLVESGGGVVQPGRSLRLSCAASGFTFSSYGMHWVRQAPGKGLEWVAVIWYDGSNKYYADSVKGR
C2            ---------Q--------------------------------------------------RQ---------

CDR3
Germline      FTISRDNSKNTLYLQMNSLRAEDTAVYYCAR
C2            ------D----M------------------GGFWGAFDIWGQGTMVTVSS
```

SEQ ID NO: 10 AND 20 (respectively)

```
                                           CDR1                          CDR2
HV1-46
Germline      QVQLVGSGAEVKKPGASVKVSCKASGYTFTSYYMHWVRQAPGQGLEWMGIINPSGGSTSYAQKFQGR
C5            ---------Q----------------------FS--PN--------------------S--T----RT---------

CDR3
Germline      VTMTRDTSTSTVYMELSSLRSEDTAVYYCAR
C5            --I---------------------------EMYNWNGGWDYGMDVWGQGTLVTVSS
```

SEQ ID NO: 12 AND 22 (respectively)

```
                                           CDR1                          CDR2
HV1-69
Germline      QVQLVQSGAEVKKPGSSVKVSCKASGGTFSSYAISWVRQAPGQGLEWMGGIIPIFGTANYAQKFQGR
C15           ------------------------------------------------------------------

CDR3
Germline      VTITADESTSTAYMELSSLRSEDTAVYYCAR
C5            ------------------------------DTAMALFYYYGMDVWGQGTLVTVSS
```

Figure 7

SEQ ID NO: 2 AND 19 (respectively)

```
                                    CDR1                        CDR2
KV3-20
Germline      EIVLTQSPGTLSLSPGERATLSCRASQSVSSSYLAWYQQKPGQAPRLLIYGASSRATGIPDRFSGSG
C2            DV-M---------------G-----------H-I--------------------V------D---VS---T---

CDR3
Germline      SGTDFTLTISRLEPEDFAVYYCQQYGSS
C2            ------------------S---F------T-PWTFGQGTKLEIK
```

SEQ ID NO: 4 AND 21 (respectively)

```
                                    CDR1                        CDR2
LV2-23
Germline      QSALTQPASVSGSPGQSITISCTGTSSDVGSYNLVSWYQQHPGKAPKLMIYEGSKRPSGVSNRFSGS
C5            ------S------F--------V--V--N----EA-D-----R----D-S-N-L--DNY--------D---AF CDR3
Germline      KSGNTASLTISGLQAEDEADYYCCSYAGSS
C5            ----------------------Y-------F-TWIFGAGTQLTVLG
```

SEQ ID NO: 6 AND 23 (respectively)

```
                                    CDR1                        CDR2
LV2-14
Germline      QSALTQPASVSGSPGQSITISCTGTSSDVGGYNYVSWYQQHPGKAPKLMIYEVSNRPSGVSNRFSGS
C15           ------------------T----------------------------------------------

CDR3
Germline      KSGNTASLTISGLQAEDEADYYCSSYTSSS
C15           ----------------------------R---GTPYVFGTGTKLTVLG
```

FIG. 8A

```
   1  ATGGGCTGGT CCTGCATCAT CCTGTTCCTG GTGGCCACCG CCACCGGCCA
  51  GGTCCAGCTG GTGCAGTCTG GGGGAGGCGT GGTCCAGCCT GGGAGGTCCC
 101  TGAGACTCTC CTGTGCAGCG TCTGGATTCA CCTTCAGTAG CTATGGCATG
 151  CACTGGGTCC GCCAGGCTCC AGGCAAGGGG CTGGAGTGGG TGGCAGTTAT
 201  ATGGTATGAT GGAAGTAGGC AATATTATGC TGACTCCGTG AAGGGCCGAT
 251  TCACCATCTC CAGAGACGAT TCCAAGAACA CGATGTATCT GCAAATGAAC
 301  AGCCTGAGAG CCGAAGACAC GGCTGTTTAT TACTGTGCGA GAGGGGGATT
 351  TTGGGGGGCT TTTGATATCT GGGGCCAAGG GACAATGGTC ACCGTCTCCT
 401  CAGCATCAAC AAAGGGGCCT AGCGTGTTTC CACTGGCCCC CTCTAGTAAA
 451  TCCACCTCTG GCGGAACAGC AGCCCTGGGT TGTCTGGTGA AGGACTACTT
 501  CCCAGAGCCC GTCACTGTGA GCTGGAACTC CGGCGCCCTG ACAAGCGGAG
 551  TCCATACTTT TCCTGCTGTG CTGCAGTCAA GCGGGCTGTA CTCCCTGTCC
 601  TCTGTGGTCA CTGTCCCAAG TTCAAGCCTG GTACTCAGA CCTATATCTG
 651  CAACGTGAAT CACAAGCCAA GCAATACCAA AGTCGACAAG AAAGTGGAGC
 701  CCAAGTCCTG TGATAAAACA CATACTTGCC CCCCTTGTCC TGCACCAGAA
 751  CTGCTGGGAG GTCCATCCGT GTTCCTGTTT CCACCCAAGC CTAAAGACAC
 801  CCTGATGATT CTCGGACTC CAGAGGTCAC CTGCGTGGTC GTGGACGTGA
 851  GCCACGAGGA TCCCGAAGTC AAGTTCAACT GGTACGTGGA TGGCGTCGAA
 901  GTGCATAATG CTAAGACAAA ACCACGGGAG GAACAGTACA ACTCCACTTA
 951  TCGCGTCGTG TCTGTCCTGA CCGTGCTGCA CCAGGATTGG CTGAACGGCA
1001  AGGAGTATAA GTGCAAAGTG TCCAATAAGG CTCTGCCCGC ACCTATCGAG
1051  AAAACAATTT CTAAGGCTAA AGGACAGCCT AGAGAACCAC AGGTGTACAC
1101  TCTGCCTCCA TCTCGGGAGG AAATGACCAA GAACCAGGTC AGTCTGACAT
1151  GTCTGGTGAA AGGCTTCTAT CCCAGCGACA TCGCAGTGGA GTGGGAATCC
1201  AATGGACAGC CTGAGAACAA TTACAAGACC ACACCCCTG TGCTGGACTC
1251  TGATGGCAGT TTCTTTCTGT ATAGTAAGCT GACCGTGGAT AAATCAAGGT
1301  GGCAGCAGGG AAACGTCTTT AGTTGTTCAG TGATGCACGA AGCACTGCAT
1351  AATCACTACA CCCAGAAGTC ACTGTCACTG TCCCCAGGAT GA
(SEQ ID: 60)
```

```
MGWSCIILFL VATATGQVQL VQSGGGVVQP GRSLRLSCAA SGFTFSSYGM HWVRQAPGKG  60
LEWVAVIWYD GSRQYYADSV KGRFTISRDD SKNTMYLQMN SLRAEDTAVY YCARGGFWGA 120
FDIWGQGTMV TVSSASTKGP SVFPLAPSSK STSGGTAALG CLVKDYFPEP VTVSWNSGAL 180
TSGVHTFPAV LQSSGLYSLS SVVTVPSSSL GTQTYICNVN HKPSNTKVDK KVEPKSCDKT 240
HTCPPCPAPE LLGGPSVFLF PPKPKDTLMI SRTPEVTCVV VDVSHEDPEV KFNWYVDGVE 300
VHNAKTKPRE EQYNSTYRVV SVLTVLHQDW LNGKEYKCKV SNKALPAPIE KTISKAKGQP 360
REPQVYTLPP SREEMTKNQV SLTCLVKGFY PSDIAVEWES NGQPENNYKT TPPVLDSDGS 420
FFLYSKLTVD KSRWQQGNVF SCSVMHEALH NHYTQKSLSL SPG                 463
(SEQ ID: 61)
```

FIG. 8B

```
  1 ATGGGCTGGT CCTGCATCAT CCTGTTCCTG GTGGCCACCG CCACCGGCGA
 51 TGTTGTGATG ACTCAGTCTC CAGGCACCCT GTCTTTGTCT CCAGGGGAAG
101 GAGCCACACT CTCCTGCAGG GCCAGTCAAC ATGTTATCAG CAGCTACTTA
151 GCCTGGTATC AGCAAAAACC TGGCCAGGCT CCCAGGCTCC TCGTCTACGG
201 TGCATCCAGT AGGGACACTG GCGTCTCAGA CAGGTTCACT GGCAGTGGGT
251 CTGGGACAGA CTTCACTCTC ACCATCAGCA GACTGGAGCC TGAAGATTCT
301 GCGGTGTATT TCTGTCAGCA GTATGGTACA TCACCGTGGA CGTTCGGCCA
351 AGGGACCAAG CTGGAGATCA AACGTACTGT GGCCGCTCCA TCTGTCTTCA
401 TTTTTCCACC CAGTGACGAA CAGCTGAAGT CCGGGACAGC TAGCGTGGTC
451 TGTCTGCTGA ACAATTTTTA CCCCAGGGAA GCCAAAGTGC AGTGGAAGGT
501 CGATAACGCT CTGCAGTCTG GAAATAGTCA GGAGTCAGTG ACAGAACAGG
551 ACTCCAAAGA TAGCACTTAT TCTCTGTCTA GTACCCTGAC ACTGAGCAAG
601 GCAGACTACG AGAAGCATAA AGTGTATGCC TGTGAAGTCA CTCATCAGGG
651 GCTGTCCAGT CCCGTCACAA AATCCTTTAA TCGTGGCGAA TGTTGA
(SEQ ID: 62)
```

```
MGWSCIILFL VATATGDVVM TQSPGTLSLS PGEGATLSCR ASQHVISSYL AWYQQKPGQA  60
PRLLVYGASS RDTGVSDRFT GSGSGTDFTL TISRLEPEDS AVYFCQQYGT SPWTFGQGTK 120
LEIKRTVAAP SVFIFPPSDE QLKSGTASVV CLLNNFYPRE AKVQWKVDNA LQSGNSQESV 180
TEQDSKDSTY SLSSTLTLSK ADYEKHKVYA CEVTHQGLSS PVTKSFNRGE C          231
(SEQ ID: 63)
```

FIG. 9A

```
   1  ATGGGCTGGT CCTGCATCAT CCTGTTCCTG GTGGCCACCG CCACCGGCCA
  51  GGTGCAGCTG GTGCAATCTG GGGCTGAGGT GAAGAAGCCT GGGGCCTCAG
 101  TGAAGGTTTC CTGCAAGGCA TCTGGATTCA GTTTCCCCAA CTACTACATG
 151  CACTGGGTGC GACAGGCCCC TGGACAAGGG CTTGAGTGGA TGGGAATAAT
 201  CAGCCCTACC GGTGGTAGCA GAACGTACGC ACAGAAGTTC CAGGGCAGAG
 251  TCACCATAAC CAGGGACACG TCCACGAGCA CAGTCTATAT GGAGTTGAGC
 301  AGCCTGAGAT CTGAGGACAC GGCCGTCTAT TACTGTGCGA GAGAAATGTA
 351  CAACTGGAAC GGAGGTTGGG ACTACGGTAT GGACGTCTGG GGCCAAGGAA
 401  CCCTGGTCAC CGTCTCCTCA GCATCAACAA AGGGGCCTTC CGTGTTTCCA
 451  CTGGCCCCCT CTAGTAAAAG CACCTCTGGC GGAACAGCAG CCCTGGGTTG
 501  TCTGGTGAAG GACTACTTCC CAGAGCCAGT CACCGTGTCC TGGAACAGCG
 551  GCGCCCTGAC ATCCGGAGTC CATACTTTTC CTGCTGTGCT GCAGTCATCC
 601  GGGCTGTACA GCCTGAGCTC TGTGGTCACT GTCCAAGTT CATCCCTGGG
 651  TACTCAGACC TATATCTGCA ACGTGAATCA CAAGCCATCC AATACCAAAG
 701  TGGACAAGAA AGTGGAGCCC AAGAGCTGTG ATAAAACACA TACTTGCCCC
 751  CCTTGTCCTG CACCAGAACT GCTGGGAGGT CCATCCGTGT TCCTGTTTCC
 801  ACCCAAGCCT AAAGACACCC TGATGATTTC TCGAACTCCA GAGGTCACCT
 851  GCGTGGTCGT GGACGTGTCC CACGAGGACC CCGAAGTCAA GTTCAACTGG
 901  TACGTGGATG GCGTCGAAGT GCATAATGCT AAGACAAAAC CAAGAGAGGA
 951  ACAGTACAAC AGCACTTATC GCGTCGTGTC TGTCCTGACC GTGCTGCACC
1001  AGGATTGGCT GAACGGCAAG GAGTATAAGT GCAAAGTGAG CAATAAGGCT
1051  CTGCCCGCAC CTATCGAGAA AACAATTTCT AAGGCTAAAG GACAGCCTAG
1101  GGAACCACAG GTGTACACTC TGCCTCCATC TCGGGAGGAA ATGACCAAGA
1151  ACCAGGTCAG TCTGACATGT CTGGTGAAAG GCTTCTATCC CTCCGACATC
1201  GCAGTGGAGT GGGAAAGCAA TGGACAGCCT GAGAACAATT ACAAGACCAC
1251  ACCCCCTGTG CTGGACTCTG ATGGCAGTTT CTTTCTGTAT AGTAAGCTGA
1301  CCGTGGATAA ATCACGGTGG CAGCAGGGAA ATGTCTTTAG TTGTTCAGTG
1351  ATGCACGAAG CACTGCACAA TCACTACACT CAGAAATCAC TGTCACTGTC
1401  CCCAGGGTAA
```

(SEQ ID: 64)

```
MGWSCIILFL VATATGQVQL VQSGAEVKKP GASVKVSCKA SGFSFPNYYM HWVRQAPGQG  60
LEWMGIISPT GGSRTYAQKF QGRVTITRDT STSTVYMELS SLRSEDTAVY YCAREMYNWN 120
GGWDYGMDVW GQGTLVTVSS ASTKGPSVFP LAPSSKSTSG GTAALGCLVK DYFPEPVTVS 180
WNSGALTSGV HTFPAVLQSS GLYSLSSVVT VPSSSLGTQT YICNVNHKPS NTKVDKKVEP 240
KSCDKTHTCP PCPAPELLGG PSVFLFPPKP KDTLMISRTP EVTCVVVDVS HEDPEVKFNW 300
YVDGVEVHNA KTKPREEQYN STYRVVSVLT VLHQDWLNGK EYKCKVSNKA LPAPIEKTIS 360
KAKGQPREPQ VYTLPPSREE MTKNQVSLTC LVKGFYPSDI AVEWESNGQP ENNYKTTPPV 420
LDSDGSFFLY SKLTVDKSRW QQGNVFSCSV MHEALHNHYT QKSLSLSPG             468
```

(SEQ ID: 65)

FIG. 9B

```
  1 ATGGGCTGGT CCTGCATCAT CCTGTTCCTG GTGGCCACCG CCACCGGCCA
 51 GTCTGCCCTG ACTCAGTCTG CCTCCGTGTC TGGATTTCCT GGACAGTCGA
101 TCACCGTCTC CTGCGTTGGA ACCAACAGTG ATGTTGAGGC TTATGACCTC
151 GTCTCCTGGT ACCGACAACA CCCAGACAAG TCCCCCAACC TCCTAATTTA
201 TGACAACTAT AAGCGACCCT CAGGGGTTTC TGATCGCTTC TCTGCCTTCA
251 AATCTGGAAA CACGGCCTCC CTGACCATTT CTGGCCTCCA GGCTGAAGAC
301 GAGGCTTATT ATTACTGCTG CTCTTATGCA GGTTTTCCA CCTGGATCTT
351 CGGCGCGGGG ACCCAGCTCA CCGTTTTAGG TCAGCCCAAG GCCAACCCCA
401 CCGTGACCCT GTTCCCCCCT TCCTCGAGG AGCTGCAGGC CAACAAGGCC
451 ACCCTGGTGT GCCTGATCTC CGACTTCTAC CCCGGCGCTG TGACCGTCGC
501 TTGGAAAGCC GATGGCTCCC CCGTGAAGGC TGGAGTGGAG ACCACCAAGC
551 CCTCCAAGCA GTCCAACAAC AAGTACGCCG CTAGCTCCTA CCTGAGCCTG
601 ACCCCCGAGC AGTGGAAGTC CCACAGGTCC TACTCCTGCC AGGTGACCCA
651 CGAGGGCTCC ACCGTGGAGA AGACCGTGGC TCCCACCGAG TGCAGCTAA
```

(SEQ ID: 66)

```
MGWSCIILFL VATATGQSAL TQSASVSGFP GQSITVSCVG TNSDVEAYDL VSWYRQHPDK  60
SPNLLIYDNY KRPSGVSDRF SAFKSGNTAS LTISGLQAED EAYYYCCSYA GFSTWIFGAG 120
TQLTVLGQPK ANPTVTLFPP SSEELQANKA TLVCLISDFY PGAVTVAWKA DGSPVKAGVE 180
TTKPSKQSNN KYAASSYLSL TPEQWKSHRS YSCQVTHEGS TVEKTVAPTE CS         232
```

(SEQ ID: 67)

FIG. 10A

```
   1  ATGGGCTGGT CCTGCATCAT CCTGTTCCTG GTGGCCACCG CCACCGGCCA
  51  GGTGCAGCTG GTGCAGTCCG GGCTGAGGT GAAGAAGCCT GGGTCCTCGG
 101  TGAAGGTCTC CTGCAAGGCT TCTGGAGGCA CCTTCAGCAG CTATGCTATC
 151  AGCTGGGTGC GACAGGCCCC TGGACAAGGG CTTGAGTGGA TGGGAGGGAT
 201  CATCCCTATC TTTGGTACAG CAAACTACGC ACAGAAGTTC CAGGGCAGAG
 251  TCACGATTAC CGCGGACGAA TCCACGAGCA CAGCCTACAT GGAGCTGAGC
 301  AGCCTGAGAT CTGAGGACAC GGCCGTGTAT TACTGTGCGA GAGATACTGC
 351  TATGGCACTA TTCTACTACT ACTACGGTAT GGACGTCTGG GGCCAAGGCA
 401  CCCTGGTCAC CGTCTCCTCA GCATCAACAA AGGGGCCTAG CGTGTTTCCA
 451  CTGGCCCCCT CTAGTAAATC CACCTCTGGC GGAACAGCAG CCCTGGGTTG
 501  TCTGGTGAAG GACTACTTCC CAGAGCCCGT CACTGTGAGC TGGAACTCCG
 551  GCGCCCTGAC AAGCGGAGTC CATACTTTTC CTGCTGTGCT GCAGTCAAGC
 601  GGGCTGTACT CCCTGTCCTC TGTGGTCACT GTCCCAAGTT CAAGCCTGGG
 651  TACTCAGACC TATATCTGCA ACGTGAATCA CAAGCCAAGC AATACCAAAG
 701  TCGACAAGAA AGTGGAGCCC AAGTCCTGTG ATAAAACACA TACTTGCCCC
 751  CCTTGTCCTG CACCAGAACT GCTGGGAGGT CCATCCGTGT TCCTGTTTCC
 801  ACCCAAGCCT AAAGACACCC TGATGATTTC TCGGACTCCA GAGGTCACCT
 851  GCGTGGTCGT GGACGTGAGC CACGAGGATC CCGAAGTCAA GTTCAACTGG
 901  TACGTGGATG GCGTCGAAGT GCATAATGCT AAGACAAAAC CACGGGAGGA
 951  ACAGTACAAC TCCACTTATC GCGTCGTGTC TGTCCTGACC GTGCTGCACC
1001  AGGATTGGCT GAACGGCAAG GAGTATAAGT GCAAAGTGTC CAATAAGGCT
1051  CTGCCCGCAC CTATCGAGAA AACAATTTCT AAGGCTAAAG GACAGCCTAG
1101  AGAACCACAG GTGTACACTC TGCCTCCATC TCGGGAGGAA ATGACCAAGA
1151  ACCAGGTCAG TCTGACATGT CTGGTGAAAG GCTTCTATCC AGCGACATC
1201  GCAGTGGAGT GGGAATCCAA TGGACAGCCT GAGAACAATT ACAAGACCAC
1251  ACCCCCTGTG CTGGACTCTG ATGGCAGTTT CTTTCTGTAT AGTAAGCTGA
1301  CCGTGGATAA ATCAAGGTGG CAGCAGGGAA ACGTCTTTAG TTGTTCAGTG
1351  ATGCACGAAG CACTGCATAA TCACTACACC CAGAAGTCAC TGTCACTGTC
1401  CCCAGGATGA
```

(SEQ ID: 68)

```
MGWSCIILFL VATATGQVQL VQSGAEVKKP GSSVKVSCKA SGGTFSSYAI SWVRQAPGQG  60
LEWMGGIIPI FGTANYAQKF QGRVTITADE STSTAYMELS SLRSEDTAVY YCARDTAMAL 120
FYYYYGMDVW GQGTLVTVSS ASTKGPSVFP LAPSSKSTSG GTAALGCLVK DYFPEPVTVS 180
WNSGALTSGV HTFPAVLQSS GLYSLSSVVT VPSSSLGTQT YICNVNHKPS NTKVDKKVEP 240
KSCDKTHTCP PCPAPELLGG PSVFLFPPKP KDTLMISRTP EVTCVVVDVS HEDPEVKFNW 300
YVDGVEVHNA KTKPREEQYN STYRVVSVLT VLHQDWLNGK EYKCKVSNKA LPAPIEKTIS 360
KAKGQPREPQ VYTLPPSREE MTKNQVSLTC LVKGFYPSDI AVEWESNGQP ENNYKTTPPV 420
LDSDGSFFLY SKLTVDKSRW QQGNVFSCSV MHEALHNHYT QKSLSLSPG            469
```
(SEQ ID: 69)

FIG. 10B

```
  1  ATGGGCTGGT CCTGCATCAT CCTGTTCCTG GTGGCCACCG CCACCGGCCA
 51  GTCTGCCCTG ACTCAGCCTG CCTCCGTGTC TGGGTCTCCT GGACAGTCGA
101  CCACCATCTC CTGCACTGGA ACCAGCAGTG ACGTTGGTGG TTATAACTAT
151  GTCTCCTGGT ACCAACAGCA CCCAGGCAAA GCCCCCAAAC TCATGATTTA
201  TGAGGTCAGT AATCGGCCCT CAGGGGTTTC TAATCGCTTC TCTGGCTCCA
251  AGTCTGGCAA CACGGCCTCC CTGACCATCT CTGGGCTCCA GGCTGAGGAC
301  GAGGCTGATT ATTACTGCAG CTCATATAGA AGCAGCGGCA CTCCTTATGT
351  CTTCGGAACT GGGACCAAGC TGACCGTCCT AGGTCAGCCC AAGGCCAACC
401  CCACCGTGAC CCTGTTCCCC CCTTCCTCCG AGGAGCTGCA GGCCAACAAG
451  GCCACCCTGG TGTGCCTGAT CTCCGACTTC TACCCCGGCG CTGTGACCGT
501  CGCTTGGAAA GCCGATGGCT CCCCCGTGAA GGCTGGAGTG GAGACCACCA
551  AGCCCTCCAA GCAGTCCAAC AACAAGTACG CCGCTAGCTC CTACCTGAGC
601  CTGACCCCCG AGCAGTGGAA GTCCCACAGG TCCTACTCCT GCCAGGTGAC
651  CCACGAGGGC TCCACCGTGG AGAAGACCGT GGCTCCCACC GAGTGCAGCT
701  AA
```

(SEQ ID: 70)

```
MGWSCIILFL VATATGQSAL TQPASVSGSP GQSTTISCTG TSSDVGGYNY VSWYQQHPGK  60
APKLMIYEVS NRPSGVSNRF SGSKSGNTAS LTISGLQAED EADYYCSSYR SSGTPYVFGT 120
GTKLTVLGQP KANPTVTLFP PSSEELQANK ATLVCLISDF YPGAVTVAWK ADGSPVKAGV 180
ETTKPSKQSN NKYAASSYLS LTPEQWKSHR SYSCQVTHEG STVEKTVAPT ECS        233
```

(SEQ ID: 71)

Figure 15

Human IGHV3-33

CAGGTGCAGCTGGTGGAGTCTGGGGGAGGCGTGGTCCAGCCTGGGAGGTCCCTGAGACTCTCCTGTGCAGCGTCTGGATTCACCTTCAGTAGC
TATGGCATGCACTGGGTCCGCCAGGCTCCAGGCAAGGGGCTGGAGTGGGTGGCAGTTATATGGTATGATGGAAGTAATAAATACTATGCAGAC
TCCGTGAAGGGCCGATTCACCATCTCCAGAGACAATTCCAAGAACACGCTGTATCTGCAAATGAACAGCCTGAGAGCCGAGGACACGGCTGTG
TATTACTGTGCGAGA (SEQ ID NO: 72)

Human IGKV3-20

GAAATTGTGTTGACGCAGTCTCCAGGCACCCTGTCTTTGTCTCCAGGGGAAAGAGCCACCCTCTCCTGCAGGGCCAGTCAGAGTGTTAGCAGC
AGCTACTTAGCCTGGTACCAGCAGAAACCTGGCCAGGCTCCCAGGCTCCTCATCTATGGTGCATCCAGCAGGGCCACTGGCATCCCAGACAGG
TTCAGTGGCAGTGGGTCTGGGACAGACTTCACTCTCACCATCAGCAGACTGGAGCCTGAAGATTTTGCAGTGTATTACTGTCAGCAGTATGGT
AGCTCA (SEQ ID NO: 13)

Human IGHV1-46

CAGGTGCAGCTGGTGCAGTCTGGGGCTGAGGTGAAGAAGCCTGGGGCCTCAGTGAAGGTTTCCTGCAAGGCATCTGGATACACCTTCACCAGCTACTATATGCACTGGGTGC
GACAGGCCCCTGGACAAGGGCTTGAGTGGATGGGAATAATCAACCCTAGTGGTGGTAGCACAAGCTACGCACAGAAGTTCCAGGGCAGAGTCACCATGACCAGGGACACGTC
CACGAGCACAGTCTACATGGAGCTGAGCAGCCTGAGATCTGAGGACACGGCCGTGTATTACTGTGCGAGA (SEQ ID NO: 14)

Human IGLV2-23

CAGTCTGCCCTGACTCAGCCTGCCTCCGTGTCTGGGTCTCCTGGACAGTCGATCACCATCTCCTGCACTGGAACCAACAGTGATGTTGGGAGT
TATAACCTTGTCTCCTGGTACCAACAGCACCCAGGCAAAGCCCCCAAACTCATGATTTATGAGGGCAGTAAGCGGCCCTCAGGGGTTTCTAAT
CGCTTCTCTGGCTCCAAGTCTGGCAACACGGCCTCCCTGACAATCTCTGGGCTCCAGGCTGAGGACGAGGCTGATTATTACTGCTGCTCATAT
GCAGGTAGTAGC (SEQ ID NO: 15)

Human IGHV1-69

CAGGTGCAGCTGGTGCAGTCTGGGGCTGAGGTGAAGAAGCCTGGGTCCTCGGTGAAGGTCTCCTGCAAGGCTTCTGGAGGCACCTTCAGCAGC
TATGCTATCAGCTGGGTGCGACAGGCCCCTGGACAAGGGCTTGAGTGGATGGGAGGGATCATCCCTATCTTTGGTACAGCAAACTACGCACAG
AAGTTCCAGGGCAGAGTCACGATTACCGCGGACGAATCCACGAGCACAGCCTACATGGAGCTGAGCAGCCTGAGATCTGAGGACACGGCCGTG
TATTACTGTGCGAGA (SEQ ID NO: 16)

Human IGLV2-14

CAGTCTGCCCTGACTCAGCCTGCCTCCGTGTCTGGGTCTCCTGGACAGTCGATCACCATCTCCTGCACTGGAACCAGCAGTGACGTTGGTGGT
TATAACTATGTCTCCTGGTACCAACAGCACCCAGGCAAAGCCCCCAAACTCATGATTTATGAGGTCAGTAATCGGCCCTCAGGGGTTTCTAAT
CGCTTCTCTGGCTCCAAGTCTGGCAACACGGCCTCCCTGACCATCTCTGGGCTCCAGGCTGAGGACGAGGCTGATTATTACTGCAGCTCATAT
AGAAGCAGCAGC (SEQ ID NO: 17)

SEQUENCE LISTING

```
<160> NUMBER OF SEQ ID NOS: 73

<210> SEQ ID NO 1
<211> LENGTH: 327
<212> TYPE: DNA
<213> ORGANISM: Homo sapiens

<400> SEQUENCE: 1
gatgttgtga tgactcagtc tccaggcacc ctgtctttgt ctccagggga aggagccaca      60
ctctcctgca gggccagtca acatgttatc agcagctact tagcctggta tcagcaaaaa     120
cctggccagg ctcccaggct cctcgtctac ggtgcatcca gtagggacac tggcgtctca     180
gacaggttca ctggcagtgg gtctgggaca gacttcactc tcaccatcag cagactggag     240
cctgaagatt ctgcggtgta tttctgtcag cagtatggta catcaccgtg gacgttcggc     300
```

```
caagggacca agctggagat caaacgt                                         327
```

<210> SEQ ID NO 2
<211> LENGTH: 109
<212> TYPE: PRT
<213> ORGANISM: Homo sapiens

<400> SEQUENCE: 2

```
Asp Val Val Met Thr Gln Ser Pro Gly Thr Leu Ser Leu Ser Pro Gly
1               5                   10                  15

Glu Gly Ala Thr Leu Ser Cys Arg Ala Ser Gln His Val Ile Ser Ser
            20                  25                  30

Tyr Leu Ala Trp Tyr Gln Gln Lys Pro Gly Gln Ala Pro Arg Leu Leu
        35                  40                  45

Val Tyr Gly Ala Ser Ser Arg Asp Thr Gly Val Ser Asp Arg Phe Thr
    50                  55                  60

Gly Ser Gly Ser Gly Thr Asp Phe Thr Leu Thr Ile Ser Arg Leu Glu
65                  70                  75                  80

Pro Glu Asp Ser Ala Val Tyr Phe Cys Gln Gln Tyr Gly Thr Ser Pro
                85                  90                  95

Trp Thr Phe Gly Gln Gly Thr Lys Leu Glu Ile Lys Arg
            100                 105
```

<210> SEQ ID NO 3
<211> LENGTH: 333
<212> TYPE: DNA
<213> ORGANISM: Homo sapiens

<400> SEQUENCE: 3

```
cagtctgccc tgactcagtc tgcctccgtg tctggatttc ctggacagtc gatcaccgtc    60
tcctgcgttg gaaccaacag tgatgttgag gcttatgacc tcgtctcctg gtaccgacaa   120
cacccagaca gtcccccaa cctcctaatt tatgacaact ataagcgacc ctcaggggtt    180
tctgatcgct tctctgcctt caaatctgga aacacggcct ccctgaccat ttctggcctc   240
caggctgaag acgaggctta ttattactgc tgctcttatg caggtttttc cacctggatc   300
ttcggcgcgg ggacccagct caccgtttta ggt                                333
```

<210> SEQ ID NO 4
<211> LENGTH: 111
<212> TYPE: PRT
<213> ORGANISM: Homo sapiens

<400> SEQUENCE: 4

```
Gln Ser Ala Leu Thr Gln Ser Ala Ser Val Ser Gly Phe Pro Gly Gln
1               5                   10                  15

Ser Ile Thr Val Ser Cys Val Gly Thr Asn Ser Asp Val Glu Ala Tyr
            20                  25                  30

Asp Leu Val Ser Trp Tyr Arg Gln His Pro Asp Ser Pro Lys Pro Asn Leu
        35                  40                  45

Leu Ile Tyr Asp Asn Tyr Lys Arg Pro Ser Gly Val Ser Asp Arg Phe
    50                  55                  60

Ser Ala Phe Lys Ser Gly Asn Thr Ala Ser Leu Thr Ile Ser Gly Leu
65                  70                  75                  80

Gln Ala Glu Asp Glu Ala Tyr Tyr Tyr Cys Cys Ser Tyr Ala Gly Phe
                85                  90                  95

Ser Thr Trp Ile Phe Gly Ala Gly Thr Gln Leu Thr Val Leu Gly
```

<210> SEQ ID NO 5
<211> LENGTH: 336
<212> TYPE: DNA
<213> ORGANISM: Homo sapiens

<400> SEQUENCE: 5

```
cagtctgccc tgactcagcc tgcctccgtg tctgggtctc ctggacagtc gaccaccatc    60
tcctgcactg gaaccagcag tgacgttggt ggttataact atgtctcctg gtaccaacag   120
cacccaggca aagcccccaa actcatgatt tatgaggtca gtaatcggcc ctcagggggtt  180 tctaatcgct ctctctggctc caagtctggc aacacggcct ccctgaccat ctctgggctc   240
caggctgagg acgaggctga ttattactgc agctcatata aagcagcgg cactccttat    300 gtcttcggaa ctgggaccaa gctgaccgtc ctaggt                             336
```

<210> SEQ ID NO 6
<211> LENGTH: 112
<212> TYPE: PRT
<213> ORGANISM: Homo sapiens

<400> SEQUENCE: 6

```
Gln Ser Ala Leu Thr Gln Pro Ala Ser Val Ser Gly Ser Pro Gly Gln
1               5                   10                  15

Ser Thr Thr Ile Ser Cys Thr Gly Thr Ser Ser Asp Val Gly Gly Tyr
                20                  25                  30

Asn Tyr Val Ser Trp Tyr Gln Gln His Pro Gly Lys Ala Pro Lys Leu
            35                  40                  45

Met Ile Tyr Glu Val Ser Asn Arg Pro Ser Gly Val Ser Asn Arg Phe
        50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Ser Ser Tyr Arg Ser Ser
                85                  90                  95

Gly Thr Pro Tyr Val Phe Gly Thr Gly Thr Lys Leu Thr Val Leu Gly
            100                 105                 110
```

<210> SEQ ID NO 7
<211> LENGTH: 354
<212> TYPE: DNA
<213> ORGANISM: Homo sapiens

<400> SEQUENCE: 7

```
caggtccagc tggtgcagtc tgggggaggc gtggtccagc ctgggaggtc cctgagactc    60
tcctgtgcag cgtctggatt caccttcagt agctatggca tgcactgggt ccgccaggct   120
ccaggcaagg ggctggagtg ggtggcagtt atatggtatg atggaagtag caatattat    180 gctgactccg tgaagggccg attcaccatc tccagagacg attccaagaa cacgatgtat   240
ctgcaaatga acagcctgag agccgaagac acggctgttt attactgtgc gagagggga    300 ttttgggggg cttttgatat ctggggccaa gggacaatgg tcaccgtctc ctca          354
```

<210> SEQ ID NO 8
<211> LENGTH: 118
<212> TYPE: PRT
<213> ORGANISM: Homo sapiens

<400> SEQUENCE: 8

```
Gln Val Gln Leu Val Gln Ser Gly Gly Val Val Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
            35                  40                  45

Ala Val Ile Trp Tyr Asp Gly Ser Arg Gln Tyr Tyr Ala Asp Ser Val
        50                  55                  60

Lys Gly Arg Phe Thr Ile Ser Arg Asp Asp Ser Lys Asn Thr Met Tyr
65                  70                  75                  80

Leu Gln Met Asn Ser Leu Arg Ala Glu Asp Thr Ala Val Tyr Tyr Cys
                85                  90                  95

Ala Arg Gly Gly Phe Trp Gly Ala Phe Asp Ile Trp Gly Gln Gly Thr
            100                 105                 110

Met Val Thr Val Ser Ser
            115
```

<210> SEQ ID NO 9
<211> LENGTH: 372
<212> TYPE: DNA
<213> ORGANISM: Homo sapiens

<400> SEQUENCE: 9

```
caggtgcagc tggtgcaatc tggggctgag gtgaagaagc ctggggcctc agtgaaggtt      60
tcctgcaagg catctggatt cagtttcccc aactactaca tgcactgggt gcgacaggcc     120
cctggacaag gcttgagtg gatgggaata atcagcccta ccggtggtag cagaacgtac     180
gcacagaagt tccagggcag agtcaccata accagggaca cgtccacgag cacagtctat     240
atggagttga gcagcctgag atctgaggac acggccgtct attactgtgc gagagaaatg     300
tacaactgga acggaggttg ggactacggt atggacgtct ggggccaagg aaccctggtc     360
accgtctcct ca                                                         372
```

<210> SEQ ID NO 10
<211> LENGTH: 124
<212> TYPE: PRT
<213> ORGANISM: Homo sapiens

<400> SEQUENCE: 10

```
Gln Val Gln Leu Val Gln Ser Gly Ala Glu Val Lys Lys Pro Gly Ala
1               5                   10                  15

Ser Val Lys Val Ser Cys Lys Ala Ser Gly Phe Ser Phe Pro Asn Tyr
            20                  25                  30

Tyr Met His Trp Val Arg Gln Ala Pro Gly Gln Gly Leu Glu Trp Met
            35                  40                  45

Gly Ile Ile Ser Pro Thr Gly Gly Ser Arg Thr Tyr Ala Gln Lys Phe
        50                  55                  60

Gln Gly Arg Val Thr Ile Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Glu Met Tyr Asn Trp Asn Gly Gly Trp Asp Tyr Gly Met Asp
            100                 105                 110

Val Trp Gly Gln Gly Thr Leu Val Thr Val Ser Ser
            115                 120
```

<210> SEQ ID NO 11
<211> LENGTH: 372
<212> TYPE: DNA
<213> ORGANISM: Homo sapiens

<400> SEQUENCE: 11

```
caggtgcagc tggtgcagtc cggggctgag gtgaagaagc ctgggtcctc ggtgaaggtc      60
tcctgcaagg cttctggagg caccttcagc agctatgcta tcagctgggt gcgacaggcc     120
cctggacaag ggcttgagtg gatgggaggg atcatcccta tctttggtac agcaaactac     180
gcacagaagt tccagggcag agtcacgatt accgcggacg aatccacgag cacagcctac     240
atggagctga gcagcctgag atctgaggac acggccgtgt attactgtgc gagagatact     300
gctatggcac tattctacta ctactacggt atggacgtct ggggccaagg caccctggtc     360
accgtctcct ca                                                         372
```

<210> SEQ ID NO 12
<211> LENGTH: 124
<212> TYPE: PRT
<213> ORGANISM: Homo sapiens

<400> SEQUENCE: 12

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asp Thr Ala Met Ala Leu Phe Tyr Tyr Tyr Gly Met Asp
            100                 105                 110

Val Trp Gly Gln Gly Thr Leu Val Thr Val Ser Ser
        115                 120

<210> SEQ ID NO 13
<211> LENGTH: 285
<212> TYPE: DNA
<213> ORGANISM: Homo sapiens

<400> SEQUENCE: 13

```
gaaattgtgt tgacgcagtc tccaggcacc ctgtctttgt ctccagggga aagagccacc      60
ctctcctgca gggccagtca gagtgttagc agcagctact tagcctggta ccagcagaaa     120
cctggccagg ctcccaggct cctcatctat ggtgcatcca gcagggccac tggcatccca     180
gacaggttca gtggcagtgg gtctgggaca gacttcactc tcaccatcag cagactggag     240
cctgaagatt ttgcagtgta ttactgtcag cagtatggta gctca                     285
```

<210> SEQ ID NO 14
<211> LENGTH: 294
<212> TYPE: DNA
<213> ORGANISM: Homo sapiens

<400> SEQUENCE: 14

```
caggtgcagc tggtgcagtc tggggctgag gtgaagaagc ctggggcctc agtgaaggtt      60
tcctgcaagg catctggata caccttcacc agctactata tgcactgggt gcgacaggcc     120
cctggacaag ggcttgagtg gatgggaata atcaaccota gtggtggtag cacaagctac     180
gcacagaagt tccagggcag agtcaccatg accaggggaca cgtccacgag cacagtctac    240
atggagctga gcagcctgag atctgaggac acggccgtgt attactgtgc gaga           294
```

<210> SEQ ID NO 15
<211> LENGTH: 291
<212> TYPE: DNA
<213> ORGANISM: Homo sapiens

<400> SEQUENCE: 15

```
cagtctgccc tgactcagcc tgcctccgtg tctgggtctc ctggacagtc gatcaccatc      60
tcctgcactg gaaccaacag tgatgttggg agttataacc ttgtctcctg gtaccaacag     120
cacccaggca agcccccaa actcatgatt tatgagggca gtaagcggcc ctcagggtt       180 tctaatcgct tctctggctc caagtctggc aacacgcc cctgacaat ctctgggctc         240 caggctgagg acgaggctga ttattactgc tgctcatatg caggtagtag c              291
```

<210> SEQ ID NO 16
<211> LENGTH: 294
<212> TYPE: DNA
<213> ORGANISM: Homo sapiens

<400> SEQUENCE: 16

```
caggtgcagc tggtgcagtc tggggctgag gtgaagaagc ctgggtcctc ggtgaaggtc      60
tcctgcaagg cttctggagg caccttcagc agctatgcta tcagctgggt gcgacaggcc     120
cctggacaag ggcttgagtg gatgggaggg atcatcccta tctttggtac agcaaactac     180
gcacagaagt tccagggcag agtcacgatt accgcggacg aatccacgag cacagcctac    240
atggagctga gcagcctgag atctgaggac acggccgtgt attactgtgc gaga           294
```

<210> SEQ ID NO 17
<211> LENGTH: 291
<212> TYPE: DNA
<213> ORGANISM: Homo sapiens

<400> SEQUENCE: 17

```
cagtctgccc tgactcagcc tgcctccgtg tctgggtctc ctggacagtc gatcaccatc      60
tcctgcactg gaaccagcag tgacgttggt ggttataact atgtctcctg gtaccaacag     120
cacccaggca agcccccaa actcatgatt tatgaggtca gtaatcggcc ctcagggtt       180 tctaatcgct tctctggctc caagtctggc aacacggcct ccctgaccat ctctgggctc     240
caggctgagg acgaggctga ttattactgc agctcatata gaagcagcag c              291
```

<210> SEQ ID NO 18
<211> LENGTH: 98
<212> TYPE: PRT
<213> ORGANISM: Homo sapiens

<400> SEQUENCE: 18

```
Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
```

```
              35                  40                  45
Ala Val Ile Trp Tyr Asp Gly Ser Asn Lys Tyr Tyr Ala Asp Ser Val
 50                  55                  60
Lys Gly Arg Phe Thr Ile Ser Arg Asp Asn Ser Lys Asn Thr Leu Tyr
 65                  70                  75                  80
Leu Gln Met Asn Ser Leu Arg Ala Glu Asp Thr Ala Val Tyr Tyr Cys
                 85                  90                  95
Ala Arg

<210> SEQ ID NO 19
<211> LENGTH: 95
<212> TYPE: PRT
<213> ORGANISM: Homo sapiens

<400> SEQUENCE: 19

Glu Ile Val Leu Thr Gln Ser Pro Gly Thr Leu Ser Leu Ser Pro Gly
 1               5                  10                  15
Glu Arg Ala Thr Leu Ser Cys Arg Ala Ser Gln Ser Val Ser Ser Ser
                 20                  25                  30
Tyr Leu Ala Trp Tyr Gln Gln Lys Pro Gly Gln Ala Pro Arg Leu Leu
             35                  40                  45
Ile Tyr Gly Ala Ser Ser Arg Ala Thr Gly Ile Pro Asp Arg Phe Ser
 50                  55                  60
Gly Ser Gly Ser Gly Thr Asp Phe Thr Leu Thr Ile Ser Arg Leu Glu
 65                  70                  75                  80
Pro Glu Asp Phe Ala Val Tyr Tyr Cys Gln Gln Tyr Gly Ser Ser
                 85                  90                  95

<210> SEQ ID NO 20
<211> LENGTH: 98
<212> TYPE: PRT
<213> ORGANISM: Homo sapiens

<400> SEQUENCE: 20

Gln Val Gln Leu Val Gly Ser Gly Ala Glu Val Lys Lys Pro Gly Ala
 1               5                  10                  15
Ser Val Lys Val Ser Cys Lys Ala Ser Gly Tyr Thr Phe Thr Ser Tyr
                 20                  25                  30
Tyr Met His Trp Val Arg Gln Ala Pro Gly Gln Gly Leu Glu Trp Met
             35                  40                  45
Gly Ile Ile Asn Pro Ser Gly Gly Ser Thr Ser Tyr Ala Gln Lys Phe
 50                  55                  60
Gln Gly Arg Val Thr Met Thr Arg Asp Thr Ser Thr Ser Thr Val Tyr
 65                  70                  75                  80
Met Glu Leu Ser Ser Leu Arg Ser Glu Asp Thr Ala Val Tyr Tyr Cys
                 85                  90                  95
Ala Arg

<210> SEQ ID NO 21
<211> LENGTH: 97
<212> TYPE: PRT
<213> ORGANISM: Homo sapiens

<400> SEQUENCE: 21

Gln Ser Ala Leu Thr Gln Pro Ala Ser Val Ser Gly Ser Pro Gly Gln
 1               5                  10                  15
Ser Ile Thr Ile Ser Cys Thr Gly Thr Ser Ser Asp Val Gly Ser Tyr
```

```
                    20                  25                  30

Asn Leu Val Ser Trp Tyr Gln Gln His Pro Gly Lys Ala Pro Lys Leu
            35                  40                  45

Met Ile Tyr Glu Gly Ser Lys Arg Pro Ser Gly Val Ser Asn Arg Phe
        50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Cys Ser Tyr Ala Gly Ser
                85                  90                  95

Ser

<210> SEQ ID NO 22
<211> LENGTH: 98
<212> TYPE: PRT
<213> ORGANISM: Homo sapiens

<400> SEQUENCE: 22

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg

<210> SEQ ID NO 23
<211> LENGTH: 97
<212> TYPE: PRT
<213> ORGANISM: Homo sapiens

<400> SEQUENCE: 23

Gln Ser Ala Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Gly Tyr
            20                  25                  30

Asn Tyr Val Ser Trp Tyr Gln Gln His Pro Gly Lys Ala Pro Lys Leu
        35                  40                  45

Met Ile Tyr Glu Val Ser Asn Arg Pro Ser Gly Val Ser Asn Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Ser Ser Tyr Thr Ser Ser
                85                  90                  95

Ser

<210> SEQ ID NO 24
<211> LENGTH: 21
<212> TYPE: DNA
<213> ORGANISM: Artificial Sequence
<220> FEATURE:
<223> OTHER INFORMATION: Synthetic Polynucleotide
```

<400> SEQUENCE: 24
actgtggccg ctccatctgt c                                                    21

<210> SEQ ID NO 25
<211> LENGTH: 12
<212> TYPE: PRT
<213> ORGANISM: Homo sapiens

<400> SEQUENCE: 25

Arg Ala Ser Gln His Val Ile Ser Ser Tyr Leu Ala
1               5                   10

<210> SEQ ID NO 26
<211> LENGTH: 7
<212> TYPE: PRT
<213> ORGANISM: Homo sapiens

<400> SEQUENCE: 26

Gly Ala Ser Ser Arg Asp Thr
1               5

<210> SEQ ID NO 27
<211> LENGTH: 10
<212> TYPE: PRT
<213> ORGANISM: Homo sapiens

<400> SEQUENCE: 27

Gln Gln Tyr Gly Thr Ser Pro Trp Thr Phe
1               5                   10

<210> SEQ ID NO 28
<211> LENGTH: 14
<212> TYPE: PRT
<213> ORGANISM: Homo sapiens

<400> SEQUENCE: 28

Val Gly Thr Asn Ser Asp Val Glu Ala Tyr Asp Leu Val Ser
1               5                   10

<210> SEQ ID NO 29
<211> LENGTH: 7
<212> TYPE: PRT
<213> ORGANISM: Homo sapiens

<400> SEQUENCE: 29

Asp Asn Tyr Lys Arg Pro Ser
1               5

<210> SEQ ID NO 30
<211> LENGTH: 11
<212> TYPE: PRT
<213> ORGANISM: Homo sapiens

<400> SEQUENCE: 30

Cys Ser Tyr Ala Gly Phe Ser Thr Trp Ile Phe
1               5                   10

<210> SEQ ID NO 31
<211> LENGTH: 14
<212> TYPE: PRT
<213> ORGANISM: Homo sapiens

<400> SEQUENCE: 31

```
Thr Gly Thr Ser Ser Asp Val Gly Gly Tyr Asn Tyr Val Ser
1               5                   10
```

<210> SEQ ID NO 32
<211> LENGTH: 7
<212> TYPE: PRT
<213> ORGANISM: Homo sapiens

<400> SEQUENCE: 32

```
Glu Val Ser Asn Arg Pro Ser
1               5
```

<210> SEQ ID NO 33
<211> LENGTH: 12
<212> TYPE: PRT
<213> ORGANISM: Homo sapiens

<400> SEQUENCE: 33

```
Ser Ser Tyr Arg Ser Ser Gly Thr Pro Tyr Val Phe
1               5                   10
```

<210> SEQ ID NO 34
<211> LENGTH: 5
<212> TYPE: PRT
<213> ORGANISM: Homo sapiens

<400> SEQUENCE: 34

```
Ser Tyr Gly Met His
1               5
```

<210> SEQ ID NO 35
<211> LENGTH: 14
<212> TYPE: PRT
<213> ORGANISM: Homo sapiens

<400> SEQUENCE: 35

```
Val Ile Trp Tyr Asp Gly Ser Arg Gln Tyr Tyr Ala Asp Ser
1               5                   10
```

<210> SEQ ID NO 36
<211> LENGTH: 9
<212> TYPE: PRT
<213> ORGANISM: Homo sapiens

<400> SEQUENCE: 36

```
Gly Gly Phe Trp Gly Ala Phe Asp Ile
1               5
```

<210> SEQ ID NO 37
<211> LENGTH: 5
<212> TYPE: PRT
<213> ORGANISM: Homo sapiens

<400> SEQUENCE: 37

```
Asn Tyr Tyr Met His
1               5
```

<210> SEQ ID NO 38
<211> LENGTH: 14
<212> TYPE: PRT
<213> ORGANISM: Homo sapiens

<400> SEQUENCE: 38

```
Ile Ile Ser Pro Thr Gly Gly Ser Arg Thr Tyr Ala Gln Lys
1               5                   10
```

<210> SEQ ID NO 39
<211> LENGTH: 15
<212> TYPE: PRT
<213> ORGANISM: Homo sapiens

<400> SEQUENCE: 39

Glu Met Tyr Asn Trp Asn Gly Gly Trp Asp Tyr Gly Met Asp Val
1               5                   10                  15

<210> SEQ ID NO 40
<211> LENGTH: 5
<212> TYPE: PRT
<213> ORGANISM: Homo sapiens

<400> SEQUENCE: 40

Ser Tyr Ala Ile Ser
1               5

<210> SEQ ID NO 41
<211> LENGTH: 14
<212> TYPE: PRT
<213> ORGANISM: Homo sapiens

<400> SEQUENCE: 41

Gly Ile Ile Pro Ile Phe Gly Thr Ala Asn Tyr Ala Gln Lys
1               5                   10

<210> SEQ ID NO 42
<211> LENGTH: 15
<212> TYPE: PRT
<213> ORGANISM: Homo sapiens

<400> SEQUENCE: 42

Asp Thr Ala Met Ala Leu Phe Tyr Tyr Tyr Tyr Gly Met Asp Val
1               5                   10                  15

<210> SEQ ID NO 43
<211> LENGTH: 21
<212> TYPE: DNA
<213> ORGANISM: Artificial Sequence
<220> FEATURE:
<223> OTHER INFORMATION: Synthetic Polynucleotide

<400> SEQUENCE: 43
cgcaaatggg cggtaggcgt g                                             21

<210> SEQ ID NO 44
<211> LENGTH: 19
<212> TYPE: DNA
<213> ORGANISM: Artificial Sequence
<220> FEATURE:
<223> OTHER INFORMATION: Synthetic Polynucleotide

<400> SEQUENCE: 44
gccggtggcg gtggccacc                                                19

<210> SEQ ID NO 45
<211> LENGTH: 39
<212> TYPE: DNA
<213> ORGANISM: Artificial Sequence
<220> FEATURE:
<223> OTHER INFORMATION: Synthetic Polynucleotide

<400> SEQUENCE: 45
ggtggccacc gccaccggcc aggtccagct ggtgcagtc        39

<210> SEQ ID NO 46
<211> LENGTH: 41
<212> TYPE: DNA
<213> ORGANISM: Artificial Sequence
<220> FEATURE:
<223> OTHER INFORMATION: Synthetic Polynucleotide

<400> SEQUENCE: 46
gctaggcccc tttgttgatg ctgaggagac ggtgaccatt g        41

<210> SEQ ID NO 47
<211> LENGTH: 21
<212> TYPE: DNA
<213> ORGANISM: Artificial Sequence
<220> FEATURE:
<223> OTHER INFORMATION: Synthetic Polynucleotide

<400> SEQUENCE: 47
gcatcaacaa aggggcctag c        21

<210> SEQ ID NO 48
<211> LENGTH: 22
<212> TYPE: DNA
<213> ORGANISM: Artificial Sequence
<220> FEATURE:
<223> OTHER INFORMATION: Synthetic Polynucleotide

<400> SEQUENCE: 48
aactagaagg cacagtcgag gc        22

<210> SEQ ID NO 49
<211> LENGTH: 39
<212> TYPE: DNA
<213> ORGANISM: Artificial Sequence
<220> FEATURE:
<223> OTHER INFORMATION: Synthetic Polynucleotide

<400> SEQUENCE: 49
ggtggccacc gccaccggcc aggtgcagct ggtgcaatc        39

<210> SEQ ID NO 50
<211> LENGTH: 40
<212> TYPE: DNA
<213> ORGANISM: Artificial Sequence
<220> FEATURE:
<223> OTHER INFORMATION: Synthetic Polynucleotide

<400> SEQUENCE: 50
gctaggcccc tttgttgatg ctgaggagac ggtgaccagg        40

<210> SEQ ID NO 51
<211> LENGTH: 40
<212> TYPE: DNA
<213> ORGANISM: Artificial Sequence
<220> FEATURE:
<223> OTHER INFORMATION: Synthetic Polynucleotide

<400> SEQUENCE: 51
gctaggcccc tttgttgatg ctgaggagac ggtgaccagg        40

<210> SEQ ID NO 52
<211> LENGTH: 39
<212> TYPE: DNA
<213> ORGANISM: Artificial Sequence
<220> FEATURE:
<223> OTHER INFORMATION: Synthetic Polynucleotide

<400> SEQUENCE: 52
ggtggccacc gccaccggcg atgttgtgat gactcagtc        39

<210> SEQ ID NO 53
<211> LENGTH: 41
<212> TYPE: DNA
<213> ORGANISM: Artificial Sequence
<220> FEATURE:
<223> OTHER INFORMATION: Synthetic Polynucleotide

<400> SEQUENCE: 53
gacagatgga gcggccacag tacgtttgat ctccagcttg g     41

<210> SEQ ID NO 54
<211> LENGTH: 39
<212> TYPE: DNA
<213> ORGANISM: Artificial Sequence
<220> FEATURE:
<223> OTHER INFORMATION: Synthetic Polynucleotide

<400> SEQUENCE: 54
ggtggccacc gccaccggcc agtctgccct gactcagtc        39

<210> SEQ ID NO 55
<211> LENGTH: 36
<212> TYPE: DNA
<213> ORGANISM: Artificial Sequence
<220> FEATURE:
<223> OTHER INFORMATION: Synthetic Polynucleotide

<400> SEQUENCE: 55
gggttggcct tgggctgacc taaaacggtg agctgg           36

<210> SEQ ID NO 56
<211> LENGTH: 38
<212> TYPE: DNA
<213> ORGANISM: Artificial Sequence
<220> FEATURE:
<223> OTHER INFORMATION: Synthetic Polynucleotide

<400> SEQUENCE: 56
ggtggccacc gccaccggcc agtctgccct gactcagc         38

<210> SEQ ID NO 57
<211> LENGTH: 37
<212> TYPE: DNA
<213> ORGANISM: Homo sapiens

<400> SEQUENCE: 57
gggttggcct tgggctgacc taggacggtc agcttgg          37

<210> SEQ ID NO 58
<211> LENGTH: 20
<212> TYPE: DNA
<213> ORGANISM: Homo sapiens

<400> SEQUENCE: 58
ggtcagccca aggccaaccc                             20

<210> SEQ ID NO 59
<211> LENGTH: 18
<212> TYPE: DNA

<213> ORGANISM: Artificial Sequence
<220> FEATURE:
<223> OTHER INFORMATION: Synthetic Polynucleotide

<400> SEQUENCE: 59

```
tgtaaaacga cggccagt                                                   18
```

<210> SEQ ID NO 60
<211> LENGTH: 1392
<212> TYPE: DNA
<213> ORGANISM: Homo sapiens

<400> SEQUENCE: 60

```
atgggctggt cctgcatcat cctgttcctg gtggccaccg ccaccggcca ggtccagctg     60
gtgcagtctg ggggaggcgt ggtccagcct gggaggtccc tgagactctc ctgtgcagcg    120
tctggattca ccttcagtag ctatggcatg cactgggtcc gccaggctcc aggcaagggg    180
ctggagtggg tggcagttat atggtatgat ggaagtaggc aatattatgc tgactccgtg    240
aagggccgat tcaccatctc cagagacgat tccaagaaca cgatgtatct gcaaatgaac    300
agcctgagag ccgaagacac ggctgtttat tactgtgcga ggggggattt tggggggct    360
tttgatatct ggggccaagg gacaatggtc accgtctcct cagcatcaac aaaggggcct    420
agcgtgtttc cactggcccc ctctagtaaa tccacctctg cggaacagc agccctgggt    480
tgtctggtga aggactactt cccagagccc gtcactgtga ctggaactc cggcgccctg    540
acaagcggag tccatacttt tcctgctgtg ctgcagtcaa gcgggctgta ctccctgtcc    600
tctgtggtca ctgtcccaag ttcaagcctg gtactcaga cctatatctg caacgtgaat    660
cacaagccaa gcaatacca agtcgacaag aaagtggagc ccaagtcctg tgataaaaca    720
catacttgcc ccccttgtcc tgcaccagaa ctgctgggag tccatccgt gttcctgttt    780
ccacccaagc ctaaagacac cctgatgatt tctcggactc cagaggtcac ctgcgtggtc    840
gtggacgtga gccacgagga tcccgaagtc aagttcaact ggtacgtgga tggcgtcgaa    900
gtgcataatg ctaagacaaa accacgggag gaacagtaca actccactta tcgcgtcgtg    960
tctgtcctga ccgtgctgca ccaggattgg ctgaacggca aggagtataa gtgcaaagtg   1020
tccaataagg ctctgccccg acctatcgag aaaacaattt ctaaggctaa aggacagcct   1080
agagaaccac aggtgtacac tctgcctcca tctcgggagg aaatgaccaa gaaccaggtc   1140
agtctgacat gtctggtgaa aggcttctat cccagcgaca tcgcagtgga gtgggaatcc   1200
aatggacagc ctgagaacaa ttacaagacc acaccccctg tgctggactc tgatggcagt   1260
ttcttctctgt atagtaagct gaccgtggat aaatcaaggt ggcagcaggg aaacgtcttt   1320
agttgttcag tgatgcacga agcactgcat aatcactaca cccagaagtc actgtcactg   1380
tccccaggat ga                                                      1392
```

<210> SEQ ID NO 61
<211> LENGTH: 463
<212> TYPE: PRT
<213> ORGANISM: Homo sapiens

<400> SEQUENCE: 61

```
Met Gly Trp Ser Cys Ile Ile Leu Phe Leu Val Ala Thr Ala Thr Gly
  1               5                  10                  15

Gln Val Gln Leu Val Gln Ser Gly Gly Gly Val Val Gln Pro Gly Arg
             20                  25                  30

Ser Leu Arg Leu Ser Cys Ala Ala Ser Gly Phe Thr Phe Ser Ser Tyr
```

```
                35                  40                  45
Gly Met His Trp Val Arg Gln Ala Pro Gly Lys Gly Leu Glu Trp Val
 50                  55                  60

Ala Val Ile Trp Tyr Asp Gly Ser Arg Gln Tyr Tyr Ala Asp Ser Val
 65                  70                  75                  80

Lys Gly Arg Phe Thr Ile Ser Arg Asp Asp Ser Lys Asn Thr Met Tyr
                 85                  90                  95

Leu Gln Met Asn Ser Leu Arg Ala Glu Asp Thr Ala Val Tyr Tyr Cys
            100                 105                 110

Ala Arg Gly Gly Phe Trp Gly Ala Phe Asp Ile Trp Gly Gln Gly Thr
        115                 120                 125

Met Val Thr Val Ser Ser Ala Ser Thr Lys Gly Pro Ser Val Phe Pro
130                 135                 140

Leu Ala Pro Ser Ser Lys Ser Thr Ser Gly Gly Thr Ala Ala Leu Gly
145                 150                 155                 160

Cys Leu Val Lys Asp Tyr Phe Pro Glu Pro Val Thr Val Ser Trp Asn
                165                 170                 175

Ser Gly Ala Leu Thr Ser Gly Val His Thr Phe Pro Ala Val Leu Gln
            180                 185                 190

Ser Ser Gly Leu Tyr Ser Leu Ser Ser Val Val Thr Val Pro Ser Ser
        195                 200                 205

Ser Leu Gly Thr Gln Thr Tyr Ile Cys Asn Val Asn His Lys Pro Ser
210                 215                 220

Asn Thr Lys Val Asp Lys Lys Val Glu Pro Lys Ser Cys Asp Lys Thr
225                 230                 235                 240

His Thr Cys Pro Pro Cys Pro Ala Pro Glu Leu Leu Gly Gly Pro Ser
                245                 250                 255

Val Phe Leu Phe Pro Pro Lys Pro Lys Asp Thr Leu Met Ile Ser Arg
            260                 265                 270

Thr Pro Glu Val Thr Cys Val Val Val Asp Val Ser His Glu Asp Pro
        275                 280                 285

Glu Val Lys Phe Asn Trp Tyr Val Asp Gly Val Glu Val His Asn Ala
290                 295                 300

Lys Thr Lys Pro Arg Glu Glu Gln Tyr Asn Ser Thr Tyr Arg Val Val
305                 310                 315                 320

Ser Val Leu Thr Val Leu His Gln Asp Trp Leu Asn Gly Lys Glu Tyr
                325                 330                 335

Lys Cys Lys Val Ser Asn Lys Ala Leu Pro Ala Pro Ile Glu Lys Thr
            340                 345                 350

Ile Ser Lys Ala Lys Gly Gln Pro Arg Glu Pro Gln Val Tyr Thr Leu
        355                 360                 365

Pro Pro Ser Arg Glu Glu Met Thr Lys Asn Gln Val Ser Leu Thr Cys
370                 375                 380

Leu Val Lys Gly Phe Tyr Pro Ser Asp Ile Ala Val Glu Trp Glu Ser
385                 390                 395                 400

Asn Gly Gln Pro Glu Asn Asn Tyr Lys Thr Thr Pro Val Leu Asp
                405                 410                 415

Ser Asp Gly Ser Phe Phe Leu Tyr Ser Lys Leu Thr Val Asp Lys Ser
            420                 425                 430

Arg Trp Gln Gln Gly Asn Val Phe Ser Cys Ser Val Met His Glu Ala
        435                 440                 445

Leu His Asn His Tyr Thr Gln Lys Ser Leu Ser Leu Ser Pro Gly
450                 455                 460
```

<210> SEQ ID NO 62
<211> LENGTH: 696
<212> TYPE: DNA
<213> ORGANISM: Homo sapiens

<400> SEQUENCE: 62

```
atgggctggt cctgcatcat cctgttcctg gtggccaccg ccaccggcga tgttgtgatg      60
actcagtctc caggcaccct gtctttgtct ccagggaag gagccacact ctcctgcagg     120
gccagtcaac atgttatcag cagctactta gcctggtatc agcaaaaacc tggccaggct     180
cccaggctcc tcgtctacgg tgcatccagt agggacactg gcgtctcaga caggttcact     240
ggcagtgggt ctgggacaga cttcactctc accatcagca gactggagcc tgaagattct     300
gcggtgtatt tctgtcagca gtatggtaca tcaccgtgga cgttcggcca agggaccaag     360
ctggagatca aacgtactgt ggccgctcca tctgtcttca tttttccacc cagtgacgaa     420
cagctgaagt ccgggacagc tagcgtggtc tgtctgctga caattttta ccccagggaa     480
gccaaagtgc agtggaaggt cgataacgct ctgcagtctg gaaatagtca ggagtcagtg     540
acagaacagg actccaaaga tagcacttat tctctgtcta gtaccctgac actgagcaag     600
gcagactacg agaagcataa agtgtatgcc tgtgaagtca ctcatcaggg gctgtccagt     660
cccgtcacaa aatccttta tcgtggcgaa tgttga                               696
```

<210> SEQ ID NO 63
<211> LENGTH: 231
<212> TYPE: PRT
<213> ORGANISM: Homo sapiens

<400> SEQUENCE: 63

```
Met Gly Trp Ser Cys Ile Ile Leu Phe Leu Val Ala Thr Ala Thr Gly
1               5                   10                  15

Asp Val Val Met Thr Gln Ser Pro Gly Thr Leu Ser Leu Ser Pro Gly
            20                  25                  30

Glu Gly Ala Thr Leu Ser Cys Arg Ala Ser Gln His Val Ile Ser Ser
        35                  40                  45

Tyr Leu Ala Trp Tyr Gln Gln Lys Pro Gly Gln Ala Pro Arg Leu Leu
    50                  55                  60

Val Tyr Gly Ala Ser Ser Arg Asp Thr Gly Val Ser Asp Arg Phe Thr
65                  70                  75                  80

Gly Ser Gly Ser Gly Thr Asp Phe Thr Leu Thr Ile Ser Arg Leu Glu
                85                  90                  95

Pro Glu Asp Ser Ala Val Tyr Phe Cys Gln Gln Tyr Gly Thr Ser Pro
            100                 105                 110

Trp Thr Phe Gly Gln Gly Thr Lys Leu Glu Ile Lys Arg Thr Val Ala
        115                 120                 125

Ala Pro Ser Val Phe Ile Phe Pro Pro Ser Asp Glu Gln Leu Lys Ser
    130                 135                 140

Gly Thr Ala Ser Val Val Cys Leu Leu Asn Asn Phe Tyr Pro Arg Glu
145                 150                 155                 160

Ala Lys Val Gln Trp Lys Val Asp Asn Ala Leu Gln Ser Gly Asn Ser
                165                 170                 175

Gln Glu Ser Val Thr Glu Gln Asp Ser Lys Asp Ser Thr Tyr Ser Leu
            180                 185                 190

Ser Ser Thr Leu Thr Leu Ser Lys Ala Asp Tyr Glu Lys His Lys Val
        195                 200                 205
```

Tyr Ala Cys Glu Val Thr His Gln Gly Leu Ser Ser Pro Val Thr Lys
    210                 215                 220

Ser Phe Asn Arg Gly Glu Cys
225                 230

<210> SEQ ID NO 64
<211> LENGTH: 1410
<212> TYPE: DNA
<213> ORGANISM: Homo sapiens

<400> SEQUENCE: 64
atgggctggt cctgcatcat cctgttcctg gtggccaccg ccaccggcca ggtgcagctg      60
gtgcaatctg ggctgaggt gaagaagcct ggggcctcag tgaaggtttc ctgcaaggca     120
tctggattca gtttccccaa ctactacatg cactgggtgc acaggcccc tggacaaggg     180 cttgagtgga tgggaataat cagccctacc ggtggtagca aacgtacgc acagaagttc     240 cagggcagag tcaccataac cagggacacg tccacgagca cagtctatat ggagttgagc     300
agcctgagat ctgaggacac ggccgtctat tactgtgcga gaaatgta caactggaac     360 ggaggttggg actacggtat ggacgtctgg ggccaaggaa ccctggtcac cgtctcctca     420
gcatcaacaa agggccttc cgtgtttcca ctggcccct ctagtaaaag cacctctggc     480
ggaacagcag ccctgggttg tctggtgaag gactacttcc cagagccagt caccgtgtcc     540
tggaacagcg gcgccctgac atccggagtc catactttc ctgctgtgct gcagtcatcc     600
gggctgtaca gcctgagctc tgtggtcact gtcccaagtt catccctggg tactcagacc     660
tatatctgca acgtgaatca caagccatcc aataccaaag tggacaagaa agtggagccc     720
aagagctgtg ataaaacaca tacttgcccc ccttgtcctg caccagaact gctgggaggt     780
ccatccgtgt tcctgtttcc acccaagcct aaagacaccc tgatgatttc tcgaactcca     840
gaggtcacct gcgtggtcgt ggacgtgtcc cacgaggacc ccgaagtcaa gttcaactgg     900
tacgtggatg gcgtcgaagt gcataatgct aagacaaaac aagagagga acagtacaac     960 agcacttatc gcgtcgtgtc tgtcctgacc gtgctgcacc aggattggct gaacggcaag    1020
gagtataagt gcaaagtgag caataaggct ctgcccgcac ctatcgagaa acaatttct    1080 aaggctaaag gacagcctag ggaaccacag gtgtacactc tgcctccatc tcgggaggaa    1140
atgaccaaga accaggtcag tctgacatgt ctggtgaaag cttctatcc ctccgacatc    1200 gcagtggagt gggaaagcaa tggacagcct gagaacaatt acaagaccac accccctgtg    1260
ctggactctg atggcagttt ctttctgtat agtaagctga ccgtggataa atcacggtgg    1320
cagcagggaa atgtctttag ttgttcagtg atgcacgaag cactgcacaa tcactacact    1380
cagaaatcac tgtcactgtc cccagggtaa                                     1410

<210> SEQ ID NO 65
<211> LENGTH: 469
<212> TYPE: PRT
<213> ORGANISM: Homo sapiens

<400> SEQUENCE: 65

Met Gly Trp Ser Cys Ile Ile Leu Phe Leu Val Ala Thr Ala Thr Gly
1               5                   10                  15

Gln Val Gln Leu Val Gln Ser Gly Ala Glu Val Lys Lys Pro Gly Ala
            20                  25                  30

Ser Val Lys Val Ser Cys Lys Ala Ser Gly Phe Ser Phe Pro Asn Tyr
        35                  40                  45

```
Tyr Met His Trp Val Arg Gln Ala Pro Gly Gln Gly Leu Glu Trp Met
    50                  55                  60

Gly Ile Ile Ser Pro Thr Gly Gly Ser Arg Thr Tyr Ala Gln Lys Phe
65                  70                  75                  80

Gln Gly Arg Val Thr Ile Thr Arg Asp Thr Ser Thr Ser Thr Val Tyr
                85                  90                  95

Met Glu Leu Ser Ser Leu Arg Ser Glu Asp Thr Ala Val Tyr Tyr Cys
                100                 105                 110

Ala Arg Glu Met Tyr Asn Trp Asn Gly Gly Trp Asp Tyr Gly Met Asp
        115                 120                 125

Val Trp Gly Gln Gly Thr Leu Val Thr Val Ser Ser Ala Ser Thr Lys
130                 135                 140

Gly Pro Ser Val Phe Pro Leu Ala Pro Ser Ser Lys Ser Thr Ser Gly
145                 150                 155                 160

Gly Thr Ala Ala Leu Gly Cys Leu Val Lys Asp Tyr Phe Pro Glu Pro
                165                 170                 175

Val Thr Val Ser Trp Asn Ser Gly Ala Leu Thr Ser Gly Val His Thr
                180                 185                 190

Phe Pro Ala Val Leu Gln Ser Ser Gly Leu Tyr Ser Leu Ser Ser Val
        195                 200                 205

Val Thr Val Pro Ser Ser Ser Leu Gly Thr Gln Thr Tyr Ile Cys Asn
210                 215                 220

Val Asn His Lys Pro Ser Asn Thr Lys Val Asp Lys Lys Val Glu Pro
225                 230                 235                 240

Lys Ser Cys Asp Lys Thr His Thr Cys Pro Pro Cys Pro Ala Pro Glu
                245                 250                 255

Leu Leu Gly Gly Pro Ser Val Phe Leu Phe Pro Pro Lys Pro Lys Asp
                260                 265                 270

Thr Leu Met Ile Ser Arg Thr Pro Glu Val Thr Cys Val Val Val Asp
        275                 280                 285

Val Ser His Glu Asp Pro Glu Val Lys Phe Asn Trp Tyr Val Asp Gly
290                 295                 300

Val Glu Val His Asn Ala Lys Thr Lys Pro Arg Glu Glu Gln Tyr Asn
305                 310                 315                 320

Ser Thr Tyr Arg Val Val Ser Val Leu Thr Val Leu His Gln Asp Trp
                325                 330                 335

Leu Asn Gly Lys Glu Tyr Lys Cys Lys Val Ser Asn Lys Ala Leu Pro
                340                 345                 350

Ala Pro Ile Glu Lys Thr Ile Ser Lys Ala Lys Gly Gln Pro Arg Glu
        355                 360                 365

Pro Gln Val Tyr Thr Leu Pro Pro Ser Arg Glu Glu Met Thr Lys Asn
370                 375                 380

Gln Val Ser Leu Thr Cys Leu Val Lys Gly Phe Tyr Pro Ser Asp Ile
385                 390                 395                 400

Ala Val Glu Trp Glu Ser Asn Gly Gln Pro Glu Asn Asn Tyr Lys Thr
                405                 410                 415

Thr Pro Pro Val Leu Asp Ser Asp Gly Ser Phe Phe Leu Tyr Ser Lys
                420                 425                 430

Leu Thr Val Asp Lys Ser Arg Trp Gln Gln Gly Asn Val Phe Ser Cys
        435                 440                 445

Ser Val Met His Glu Ala Leu His Asn His Tyr Thr Gln Lys Ser Leu
450                 455                 460
```

Ser Leu Ser Pro Gly
465

<210> SEQ ID NO 66
<211> LENGTH: 699
<212> TYPE: DNA
<213> ORGANISM: Homo sapiens

<400> SEQUENCE: 66

```
atgggctggt cctgcatcat cctgttcctg gtggccaccg ccaccggcca gtctgccctg      60
actcagtctg cctccgtgtc tggatttcct ggacagtcga tcaccgtctc ctgcgttgga     120
accaacagtg atgttgaggc ttatgacctc gtcctcctggt accgacaaca cccagacaag    180
tcccccaacc tcctaattta tgacaactat aagcgaccct caggggtttc tgatcgcttc     240
tctgccttca atctggaaa cacggcctcc ctgaccattt ctggcctcca ggctgaagac      300
gaggcttatt attactgctg ctcttatgca ggttttttcca cctggatctt cggcgcgggg    360
acccagctca ccgttttagg tcagcccaag gccaacccca ccgtgaccct gttcccccct     420
tcctccgagg agctgcaggc caacaaggcc accctggtgt gcctgatctc cgacttctac     480
cccggcgctg tgaccgtcgc ttggaaagcc gatggctccc ccgtgaaggc tggagtggag     540
accaccaagc cctccaagca gtccaacaac aagtacgccg ctagctccta cctgagcctg     600
accccgagc agtggaagtc ccacaggtcc tactcctgcc aggtgaccca cgagggctcc      660
accgtggaga agaccgtggc tcccaccgag tgcagctaa                            699
```

<210> SEQ ID NO 67
<211> LENGTH: 232
<212> TYPE: PRT
<213> ORGANISM: Homo sapiens

<400> SEQUENCE: 67

Met Gly Trp Ser Cys Ile Ile Leu Phe Leu Val Ala Thr Ala Thr Gly
1               5                   10                  15

Gln Ser Ala Leu Thr Gln Ser Ala Ser Val Ser Gly Phe Pro Gly Gln
            20                  25                  30

Ser Ile Thr Val Ser Cys Val Gly Thr Asn Ser Asp Val Glu Ala Tyr
        35                  40                  45

Asp Leu Val Ser Trp Tyr Arg Gln His Pro Asp Lys Ser Pro Asn Leu
    50                  55                  60

Leu Ile Tyr Asp Asn Tyr Lys Arg Pro Ser Gly Val Ser Asp Arg Phe
65                  70                  75                  80

Ser Ala Phe Lys Ser Gly Asn Thr Ala Ser Leu Thr Ile Ser Gly Leu
                85                  90                  95

Gln Ala Glu Asp Glu Ala Tyr Tyr Tyr Cys Cys Ser Tyr Ala Gly Phe
            100                 105                 110

Ser Thr Trp Ile Phe Gly Ala Gly Thr Gln Leu Thr Val Leu Gly Gln
        115                 120                 125

Pro Lys Ala Asn Pro Thr Val Thr Leu Phe Pro Pro Ser Ser Glu Glu
    130                 135                 140

Leu Gln Ala Asn Lys Ala Thr Leu Val Cys Leu Ile Ser Asp Phe Tyr
145                 150                 155                 160

Pro Gly Ala Val Thr Val Ala Trp Lys Ala Asp Gly Ser Pro Val Lys
                165                 170                 175

Ala Gly Val Glu Thr Thr Lys Pro Ser Lys Gln Ser Asn Asn Lys Tyr
            180                 185                 190

Ala Ala Ser Ser Tyr Leu Ser Leu Thr Pro Glu Gln Trp Lys Ser His
            195                 200                 205

Arg Ser Tyr Ser Cys Gln Val Thr His Glu Gly Ser Thr Val Glu Lys
        210                 215                 220

Thr Val Ala Pro Thr Glu Cys Ser
225                 230

<210> SEQ ID NO 68
<211> LENGTH: 1410
<212> TYPE: DNA
<213> ORGANISM: Homo sapiens

<400> SEQUENCE: 68

```
atgggctggt cctgcatcat cctgttcctg gtggccaccg ccaccggcca ggtgcagctg      60
gtgcagtccg gggctgaggt gaagaagcct gggtcctcgg tgaaggtctc ctgcaaggct     120
tctggaggca ccttcagcag ctatgctatc agctgggtgc gacaggcccc tggacaaggg     180
cttgagtgga tggagggat catccctatc tttggtacag caaactacgc acagaagttc     240
cagggcagag tcacgattac cgcggacgaa tccacgagca cagcctacat ggagctgagc     300
agcctgagat ctgaggacac ggccgtgtat tactgtgcga gagatactgc tatggcacta     360
ttctactact actacggtat ggacgtctgg ggccaaggca ccctggtcac cgtctcctca     420
gcatcaacaa aggggcctag cgtgtttcca ctggccccct ctagtaaatc cacctctggc     480
ggaacagcag ccctgggttg tctggtgaag gactacttcc cagagcccgt cactgtgagc     540
tggaactccg gcgccctgac aagcggagtc catactttc ctgctgtgct gcagtcaagc     600
gggctgtact ccctgtcctc tgtggtcact gtcccaagtt caagcctggg tactcagacc     660
tatatctgca acgtgaatca caagccaagc aataccaaag tcgacaagaa agtggagccc     720
aagtcctgtg ataaaacaca cttgcccc ccttgtcctg caccagaact gctgggaggt     780
ccatccgtgt tcctgtttcc acccaagcct aaagacaccc tgatgatttc tcggactcca     840
gaggtcacct gcgtggtcgt ggacgtgagc acgaggatc cgaagtcaa gttcaactgg     900
tacgtggatg gcgtcgaagt gcataatgct aagacaaaac cacgggagga acagtacaac     960
tccacttatc gcgtcgtgtc tgtcctgacc gtgctgcacc aggattggct gaacggcaag    1020
gagtataagt gcaaagtgtc caataaggct ctgcccgcac ctatcgagaa aacaatttct    1080
aaggctaaag gacagcctag agaaccacag gtgtacactc tgcctccatc tcggaggaa    1140
atgaccaaga accaggtcag tctgacatgt ctggtgaaag gcttctatcc cagcgacatc    1200
gcagtggagt gggaatccaa tggacagcct gagaacaatt acaagaccac cccctgtg    1260
ctggactctg atggcagttt ctttctgtat agtaagctga ccgtggataa atcaaggtgg    1320
cagcagggaa acgtctttag ttgttcagtg atgcacgaag cactgcataa tcactacacc    1380
cagaagtcac tgtcactgtc cccaggatga                                    1410
```

<210> SEQ ID NO 69
<211> LENGTH: 469
<212> TYPE: PRT
<213> ORGANISM: Homo sapiens

<400> SEQUENCE: 69

Met Gly Trp Ser Cys Ile Ile Leu Phe Leu Val Ala Thr Ala Thr Gly
1               5                   10                  15

Gln Val Gln Leu Val Gln Ser Gly Ala Glu Val Lys Lys Pro Gly Ser
            20                  25                  30

```
Ser Val Lys Val Ser Cys Lys Ala Ser Gly Gly Thr Phe Ser Ser Tyr
            35                  40                  45

Ala Ile Ser Trp Val Arg Gln Ala Pro Gly Gln Gly Leu Glu Trp Met
    50                  55                  60

Gly Gly Ile Ile Pro Ile Phe Gly Thr Ala Asn Tyr Ala Gln Lys Phe
65                  70                  75                  80

Gln Gly Arg Val Thr Ile Thr Ala Asp Glu Ser Thr Ser Thr Ala Tyr
                85                  90                  95

Met Glu Leu Ser Ser Leu Arg Ser Glu Asp Thr Ala Val Tyr Tyr Cys
            100                 105                 110

Ala Arg Asp Thr Ala Met Ala Leu Phe Tyr Tyr Tyr Gly Met Asp
        115                 120                 125

Val Trp Gly Gln Gly Thr Leu Val Thr Val Ser Ser Ala Ser Thr Lys
    130                 135                 140

Gly Pro Ser Val Phe Pro Leu Ala Pro Ser Ser Lys Ser Thr Ser Gly
145                 150                 155                 160

Gly Thr Ala Ala Leu Gly Cys Leu Val Lys Asp Tyr Phe Pro Glu Pro
                165                 170                 175

Val Thr Val Ser Trp Asn Ser Gly Ala Leu Thr Ser Gly Val His Thr
            180                 185                 190

Phe Pro Ala Val Leu Gln Ser Ser Gly Leu Tyr Ser Leu Ser Ser Val
        195                 200                 205

Val Thr Val Pro Ser Ser Ser Leu Gly Thr Gln Thr Tyr Ile Cys Asn
    210                 215                 220

Val Asn His Lys Pro Ser Asn Thr Lys Val Asp Lys Lys Val Glu Pro
225                 230                 235                 240

Lys Ser Cys Asp Lys Thr His Thr Cys Pro Pro Cys Pro Ala Pro Glu
                245                 250                 255

Leu Leu Gly Gly Pro Ser Val Phe Leu Phe Pro Pro Lys Pro Lys Asp
            260                 265                 270

Thr Leu Met Ile Ser Arg Thr Pro Glu Val Thr Cys Val Val Val Asp
        275                 280                 285

Val Ser His Glu Asp Pro Glu Val Lys Phe Asn Trp Tyr Val Asp Gly
    290                 295                 300

Val Glu Val His Asn Ala Lys Thr Lys Pro Arg Glu Glu Gln Tyr Asn
305                 310                 315                 320

Ser Thr Tyr Arg Val Val Ser Val Leu Thr Val Leu His Gln Asp Trp
                325                 330                 335

Leu Asn Gly Lys Glu Tyr Lys Cys Lys Val Ser Asn Lys Ala Leu Pro
            340                 345                 350

Ala Pro Ile Glu Lys Thr Ile Ser Lys Ala Lys Gly Gln Pro Arg Glu
        355                 360                 365

Pro Gln Val Tyr Thr Leu Pro Pro Ser Arg Glu Glu Met Thr Lys Asn
    370                 375                 380

Gln Val Ser Leu Thr Cys Leu Val Lys Gly Phe Tyr Pro Ser Asp Ile
385                 390                 395                 400

Ala Val Glu Trp Glu Ser Asn Gly Gln Pro Glu Asn Asn Tyr Lys Thr
                405                 410                 415

Thr Pro Pro Val Leu Asp Ser Asp Gly Ser Phe Phe Leu Tyr Ser Lys
            420                 425                 430

Leu Thr Val Asp Lys Ser Arg Trp Gln Gln Gly Asn Val Phe Ser Cys
        435                 440                 445

Ser Val Met His Glu Ala Leu His Asn His Tyr Thr Gln Lys Ser Leu
```

Ser Leu Ser Pro Gly
465

<210> SEQ ID NO 70
<211> LENGTH: 702
<212> TYPE: DNA
<213> ORGANISM: Homo sapiens

<400> SEQUENCE: 70

```
atgggctggt cctgcatcat cctgttcctg gtggccaccg ccaccggcca gtctgccctg      60
actcagcctg cctccgtgtc tgggtctcct ggacagtcga ccaccatctc ctgcactgga     120
accagcagtg acgttggtgg ttataactat gtctcctggt accaacagca cccaggcaaa     180
gcccccaaac tcatgattta tgaggtcagt aatcggccct cagggggttttc taatcgcttc     240
tctggctcca agtctggcaa cacggcctcc ctgaccatct ctgggctcca ggctgaggac     300
gaggctgatt attactgcag ctcatataga agcagcggca ctccttatgt cttcggaact     360
gggaccaagc tgaccgtcct aggtcagccc aaggccaacc ccaccgtgac cctgttcccc     420
ccttcctccg aggagctgca ggccaacaag gccaccctgg tgtgcctgat ctccgacttc     480
taccccggcg ctgtgaccgt cgcttggaaa gccgatggcc cccccgtgaa ggctggagtg     540
gagaccacca gccctccaa gcagtccaac aacaagtacg ccgctagctc ctacctgagc     600
ctgacccccg agcagtggaa gtcccacagg tcctactcct gccaggtgac ccacgagggc     660
tccaccgtgg agaagaccgt ggctcccacc gagtgcagct aa                        702
```

<210> SEQ ID NO 71
<211> LENGTH: 233
<212> TYPE: PRT
<213> ORGANISM: Homo sapiens

<400> SEQUENCE: 71

Met Gly Trp Ser Cys Ile Ile Leu Phe Leu Val Ala Thr Ala Thr Gly
1               5                   10                  15

Gln Ser Ala Leu Thr Gln Pro Ala Ser Val Ser Gly Ser Pro Gly Gln
            20                  25                  30

Ser Thr Thr Ile Ser Cys Thr Gly Thr Ser Ser Asp Val Gly Gly Tyr
        35                  40                  45

Asn Tyr Val Ser Trp Tyr Gln Gln His Pro Gly Lys Ala Pro Lys Leu
    50                  55                  60

Met Ile Tyr Glu Val Ser Asn Arg Pro Ser Gly Val Ser Asn Arg Phe
65                  70                  75                  80

Ser Gly Ser Lys Ser Gly Asn Thr Ala Ser Leu Thr Ile Ser Gly Leu
                85                  90                  95

Gln Ala Glu Asp Glu Ala Asp Tyr Tyr Cys Ser Ser Tyr Arg Ser Ser
            100                 105                 110

Gly Thr Pro Tyr Val Phe Gly Thr Gly Thr Lys Leu Thr Val Leu Gly
        115                 120                 125

Gln Pro Lys Ala Asn Pro Thr Val Thr Leu Phe Pro Pro Ser Ser Glu
    130                 135                 140

Glu Leu Gln Ala Asn Lys Ala Thr Leu Val Cys Leu Ile Ser Asp Phe
145                 150                 155                 160

Tyr Pro Gly Ala Val Thr Val Ala Trp Lys Ala Asp Gly Ser Pro Val
                165                 170                 175

Lys Ala Gly Val Glu Thr Thr Lys Pro Ser Lys Gln Ser Asn Asn Lys

```
                    180               185               190
Tyr Ala Ala Ser Ser Tyr Leu Ser Leu Thr Pro Glu Gln Trp Lys Ser
            195               200               205

His Arg Ser Tyr Ser Cys Gln Val Thr His Glu Gly Ser Thr Val Glu
    210               215               220

Lys Thr Val Ala Pro Thr Glu Cys Ser
225                 230

<210> SEQ ID NO 72
<211> LENGTH: 294
<212> TYPE: DNA
<213> ORGANISM: Homo sapiens

<400> SEQUENCE: 72
caggtgcagc tggtggagtc tgggggaggc gtggtccagc ctgggaggtc cctgagactc     60
tcctgtgcag cgtctggatt caccttcagt agctatggca tgcactgggt ccgccaggct    120
ccaggcaagg gctggagtg gtggcagtt atatggtatg atggaagtaa taaatactat      180
gcagactccg tgaagggccg attcaccatc tccagagaca attccaagaa cacgctgtat    240
ctgcaaatga acagcctgag agccgaggac acggctgtgt attactgtgc gaga          294

<210> SEQ ID NO 73
<211> LENGTH: 7
<212> TYPE: PRT
<213> ORGANISM: Artificial Sequence
<220> FEATURE:
<223> OTHER INFORMATION: Synthetic

<400> SEQUENCE: 73

Gly Ser Gly Gly Gly Gly Ser
1               5
```

CTLA-4 ANTIBODIES AND USES THEREOF

RELATED APPLICATION

This Application is a national stage filing under 35 U.S.C. 371 of International Patent Application Serial No. PCT/CN2015/095072, filed Nov. 19, 2015, entitled "CTLA-4 ANTIBODIES AND USES THEREOF," the entire disclosure of which is hereby incorporated by reference in its entirety.

REFERENCE TO A SEQUENCE LISTING SUBMITTED AS A TEXT FILE VIA EFS-WEB

The instant application contains a Sequence Listing which has been submitted in ASCII format via EFS-Web and is hereby incorporated by reference in its entirety. Said ASCII copy, created on Dec. 10, 2020, is named X002570017US00-SUBSEQ-UG and is 50 kilobytes in size.

BACKGROUND

The section headings used herein are for organizational purposes only and are not to be construed as limiting the subject matter described.

T-cell activation depends on the presentation of peptide antigen to the antigen receptor complex (TCR) by antigen-presenting cells (APCs) together with additional signals from co-receptors (Bretscher (1970) Science 169:1042-1049). The ligation of the TCR complex alone is generally insufficient to induce a T-cell response, and, in many instances, results in non-responsiveness or T-cell anergy (Lafferty (1974) Nature 249:275-276; Jenkins et.al. (1987) J Exp Med 165:302-319). Most naïve T cells fail to respond to MHC-peptides without an additional co-signal. This underscores the importance of the antigen presenting cells (APCs) in T-cell activation with their presentation of ligands such as CD80 (also called B7-1) and CD86 (also called B7-2). Dendritic cells (DCs), macrophages, and B-cells express co-receptor ligands that are absent on stromal and epithelial cells. DCs express the highest levels of CD80'86 amongst presenting cells. Antigen presentation is context dependent with different ligands being expressed in niches of the peripheral immune system.

Co-stimuli are potent modulators of protein synthesis, metabolism, cell cycle progression, apoptosis and differentiation in T cells. Conversely, inhibitory co-stimuli can prevent the onset or downregulate immune reactions (Rudd (2003) Nat Rev Immunol 3:544-556; Rudd (2008) Nat Rev Immunol 8:153-160). The best established co-stimulatory pairs are CD28 and its binding partners CD80 and CD86. CD28 is constitutively expressed on naive and activated CD4 and CDS positive T cells (Lee et al. (1990) J Immunol 145:344-352; Gross et al. (1990) J Immunol 144:3201-3210) while CD80 and CD86 are induced on DCs with their activation (Freeman et al. (1993) J Exp Med 17S:2185-2192; Freeman et al. (1993) Science 262:909-911; Hathcock et al. (1994) J Exp Med 180:631-640). CD28 was first identified in the 19SOs as a co-receptor that enhanced TCR-induced proliferation and promoted the differentiation of naive CD4+ T cells (Gmunder et al. (1984) Eur J Biochem 142:153-160; Lesslauer et al. (1986) Eur J Immunol 16:1289-1296). It encodes a 44 kDa type I transmembrane glycoprotein that homodimerises due to disulphide bonds between cysteines juxta-positioned in the transmembrane region (Aruffo et al. (1987) Proc Natl Acad Sci USA 84:8573-8577).

The in vivo relevance of CD28 was made evident with the generation of CD2S deficient (i.e., Cd28[1]) mice (Shahinian et al. (1993) Science 261:609-612). These mice are immune compromised, showing reduced T-cell responses to antigen, defective germinal center formation and T-cell differentiation. Anti-CD3 responses are reduced by 60-70 percent. CD28 also preferentially promotes TH2 differentiation (Rulifson et al. (1997) J Immunol 158:658-665) providing help for B-cells with germinal center formation and isotype switching (Ferguson et al. (1996) J Immunol 156:4576-4581). In addition, the co-receptor prevents anergy by modulating cell cycle progression and reduces cell death or apoptosis due to the increased expression of anti-apoptotic proteins such as Bcl-2 and Bcl-$X_L$ (Mueller et al. (1996) J Immunol 156:1764-1771). CDS T-cell cytolytic responses to viral infection are also reduced due to impaired T-cell help (Kundig et al. (1996) Immunity 5:41-52).

Cytotoxic T-lymphocyte-associated Protein 4 ("CTLA-4"), a CD28 homologue, is expressed on the surface of activated CD4+ and CD8+ T cells. Like CD28, CTLA-4 also binds to CD80 and CD86. (Walunas et al. (1996) J Exp. Med. 183: 2541-2550) CTLA-4 is upregulated after T cell activation and functions as an immune checkpoint, downregulating the T cell activation and immune activity. (Grosso et al. (2013) Cancer Immun. 13:1-14).

The comparatively high binding affinity of CTLA4 has made it a potential therapy for autoimmune diseases as an agonist to reduce immune activity. It plays a role in the initial immune response to an infection of immune cells by HIV, along with the PD-1 pathway and others. Fusion proteins of CTLA4 with the Fe regions ofigG molecules (CTLA4-Ig) have been used in clinical trials for rheumatoid arthritis. A CTLA4-Ig fusion protein is commercially available as ORENCIA® (abatacept). A second generation form of CTLA4-Ig known as belatacept was also recently approved by the U.S. Food and Drug Administration based on favorable results from the randomized Phase III BENEFIT (Belatacept Evaluation of Nephroprotection and Efficacy as First Line Immunosuppression) study. It was approved in the U.S. for renal transplantation in patients that are sensitized to EBV, or Ebstein Barr Virus. Conversely, blocking CTLA-4 (e.g., using antibodies against CTLA such as ipilimumab) might be a means of inhibiting immune system tolerance to tumours and thereby providing a potentially useful immunotherapy strategy for patients with cancer (Grosso J F. and Jure-Kunkel M N. (2013) Cancer Immunity 13:5). Ipilimumab (YERVOY®) is currently indicated in the U.S. for treatment of unresectable or metastatic melanoma. Itis a therapeutic human mAb that has been shown to bind to CTLA-4 and block its interaction with B7 ligands to augment T cell activation and proliferation (Grosso et al. (2013) Cancer Immu. Rev. 13(5):1-14).

SUMMARY

The present disclosure relates to antibodies that specifically bind CTLA-4 with high affinity and modulate the effect of CTLA-4 on certain diseases.

Provided herein are antibodies (e.g., human, mouse, chimeric, humanized antibodies) that specifically bind to human CTLA-4. In certain embodiments, the antibodies described herein may comprise an antibody heavy chain of, for example, IgG or IgM. The IgG antibody heavy chain can be chosen from, for example, IgG1, IgG2, IgG3 and IgG4. In certain embodiments, the antibodies provided herein may comprise an antibody light chain chosen from, for example, a kappa light chain and a lambda light chain. In certain embodiments, the variable region of the human IgG heavy chain described herein may be encoded by a nucleic acid comprising a nucleotide sequence chosen from, for example, SEQ ID NOs: 7, 9 and 11. In certain embodiments, the variable region of the human kappa light chain may be encoded by a nucleic acid comprising a nucleotide sequence chosen from, for example, SEQ ID NO: 1. In certain embodiments, the variable region of the human lambda light chain may be encoded by a nucleic acid comprising a nucleotide sequence chosen from, for example, SEQ ID NOs: 3 and 5. While the antibodies in some of the embodiments described below are human antibodies, the disclosure also provides for antibodies with the same CDRs and non-human frameworks, chimeric antibodies, and humanized antibodies.

In some embodiments, the human antibodies described herein may comprise: a variable region of a human IgG heavy chain encoded by a nucleic acid comprising the nucleotide sequence as set forth in SEQ ID NO:7, and a variable region of a human kappa light chain encoded by a nucleic acid comprising the nucleotide sequence as set forth in SEQ ID NO: 1.

In some embodiments, the human antibodies may comprise: a variable region of a human IgG heavy chain encoded by a nucleic acid comprising the nucleotide sequence as set forth in SEQ ID NO:9, and a variable region of a human lambda light chain encoded by a nucleic acid comprising the nucleotide sequence as set forth in SEQ ID NO:3.

In some embodiments, the human antibodies may comprise: a variable region of a human IgG heavy chain encoded by a nucleic acid comprising the nucleotide sequence as set forth in SEQ ID NO:11, and a variable region of a human lambda light chain encoded by a nucleic acid comprising the nucleotide sequence as set forth in SEQ ID NO:5.

In some embodiments, the human antibodies may comprise: a heavy chain variable region comprising the amino acid sequence as set forth in SEQ ID NO: 8, and a light chain variable region comprising the amino acid sequence as set forth in SEQ ID NO: 2.

In some embodiments, the human antibodies may comprise: a heavy chain variable region comprising the amino acid sequence as set forth in SEQ ID NO: 10, and a light chain variable region comprising the amino acid sequence as set forth in SEQ ID NO: 4.

In some embodiments, the human antibodies may comprise: a heavy chain variable region comprising the amino acid sequence as set forth in SEQ ID NO: 12, and a light chain variable region comprising the amino acid sequence as set forth in SEQ ID NO: 6.

In some embodiments, the human antibodies may comprise: a variable region of a human IgG heavy chain encoded by a nucleic acid comprising the V gene segment VH 3-33 of the sequence set forth in SEQ ID NO: 72, and a variable region of a human kappa light chain encoded by a nucleic acid comprising the V gene segment KV 3-20 of the sequence set forth in SEQ ID NO: 13 (FIG. 15).

In some embodiments, the human antibodies may comprise: a variable region of a human IgG heavy chain encoded by a nucleic acid comprising the V gene segment VH 1-46 of the sequence set forth in SEQ ID NO: 14, and a variable region of a human lambda light chain encoded by a nucleic acid comprising the V gene segment LV 2-23 of the sequence set forth in SEQ ID NO: 15 (FIG. 15).

In some embodiments, the human antibodies may comprise: a variable region of a human IgG heavy chain encoded by a nucleic acid comprising the V gene segment VH 1-69 of the sequence set forth in SEQ ID NO: 16, and a variable region of a human lambda light chain encoded by a nucleic acid comprising the V gene segment LV 2-14 of the sequence set forth in SEQ ID NO: 17 (FIG. 15).

In some embodiments, the antibodies may comprise heavy chain CDR1, CDR2, and CDR3 sequences, SYGMH (SEQ ID NO:34), VIWYDGSRQYYADS (SEQ ID NO:35) and GGFWGAFDI (SEQ ID NO:36), respectively, and light chain CDR1, CDR2, and CDR3 sequences, RASQHVISSYLA (SEQ ID NO:25), GASSRDT (SEQ ID NO:26), and QQYGTSPWTF (SEQ ID NO:27), respectively. In some embodiments, the antibodies are human antibodies. In some embodiments, the antibodies are mouse, chimeric, or humanized antibodies.

In some embodiments, the antibodies may comprise heavy chain CDR1, CDR2, and CDR3 sequences, NYYMH (SEQ ID NO:37), IISPTGGSRTYAQK (SEQ ID NO:38) and EMYNWNGGWDYGMDV (SEQ ID NO:39), respectively, and light chain CDR1, CDR2, and CDR3 sequences, VGTNSDVEAYDLVS (SEQ ID NO:28), DNYKRPS (SEQ ID NO:29), and CSYAGFSTWIF (SEQ ID NO:30), respectively. In some embodiments, the antibodies are human antibodies. In some embodiments, the antibodies arc mouse, chimeric, or humanized antibodies.

In some embodiments, the antibodies may comprise heavy chain CDR1, CDR2, and CDR3 sequences, SYAIS (SEQ ID NO:40), GIIPIFGTANYAQK (SEQ ID NO:41) and DTAMALFYYYYGMDV (SEQ ID NO:42), respectively, and light chain CDR1, CDR2, and CDR3 sequences, TGTSSDVGGYNYVS (SEQ ID NO:31), EVSNRPS (SEQ ID NO:32), and SSYRSSGTPYVF (SEQ ID NO:33), respectively. In some embodiments, the antibodies are human antibodies. In some embodiments, the antibodies are mouse, chimeric, or humanized antibodies.

In some embodiments, the scFv of the antibodies may comprise a heavy chain variable region comprising the amino acid sequence as set forth is SEQ ID NO: 8, and a light chain variable region comprising the amino acid sequence as set forth is SEQ ID NO: 2.

In some embodiments, the scFv of the antibodies may comprise a heavy chain variable region comprising the amino acid sequence as set forth is SEQ ID NO: 10, and a light chain variable region comprising the amino acid sequence as set forth is SEQ ID NO: 4.

In some embodiments, the scFv of the antibodies may comprise a heavy chain variable region comprising the amino acid sequence as set forth is SEQ ID NO: 12, and a light chain variable region comprising the amino acid sequence as set forth is SEQ ID NO: 6.

Also provided herein is a cell line comprising a human antibody heavy chain transgene and a human antibody light chain transgene, wherein the cell line produces a human antibody that may specifically bind to human CTLA-4. In some embodiments, the cell line may be a CHO cell line. In certain embodiments, the cell line may secrete a human antibody that specifically binds human CTLA-4. In some embodiments, the antibody produced by the cell line may comprise:

the heavy chain CDR1, CDR2, and CDR3 sequences SYGMH (SEQ ID NO:34), VIWYDGSRQYYADS (SEQ ID NO:35) and GGFWGAFDI (SEQ ID NO:36), respectively, and the light chain CDR1, CDR2, and CDR3 sequences RASQHVISSYLA (SEQ ID NO:25), GASSRDT (SEQ ID NO:26), and QQYGTSPWTF (SEQ ID NO:27), respectively; or a heavy chain variable region comprising the amino acid sequence as set forth in SEQ ID NO: 8, and a light chain variable region comprising the amino acid sequence as set forth in SEQ ID NO: 2; or the heavy chain CDR1, CDR2, and CDR3 sequences NYYMH (SEQ ID NO:37), IISPTGGSRTYAQK (SEQ ID NO:38) and EMYNWNGGWDYGMDV (SEQ ID NO:39), respectively, and the light chain CDR1, CDR2, and CDR3 sequences VGTNSDVEAYDLVS (SEQ ID NO:28), DNYKRPS (SEQ ID NO:29), and CSYAGF-STWIF (SEQ ID NO:30), respectively; or a heavy chain variable region comprising the amino acid sequence as set forth in SEQ ID NO: 10, and a light chain variable region comprising the amino acid sequence as set forth in SEQ ID NO: 4; or the heavy chain CDR1, CDR2, and CDR3 sequences SYAIS (SEQ ID NO:40), GIIPIFGTANYAQK (SEQ ID NO:41) and DTAMALFYYYYGMDV (SEQ ID NO:42), respectively, and the light chain CDR1, CDR2, and CDR3 sequences TGTSSDVGGYNYVS (SEQ ID NO:31), EVSNRPS (SEQ ID NO:32), and SSYRSSGTPYVF (SEQ ID NO:33), respectively; or a heavy chain variable region comprising the amino acid sequence as set forth in SEQ ID NO: 12, and a light chain variable region comprising the amino acid sequence as set forth in SEQ ID NO: 6.

In some embodiments, the human antibodies as described above may be produced by a transgenic non-human animal. The transgenic non-human animal can be, for example, a mouse.

The human antibodies as described above may be any whole antibody molecule or any antigen binding fragment (i.e., "antigen-binding portion") or single chains thereof, camelid antibodies including, e.g., nanobodies, phage-display binding constructs, according to the definitions of "antibody" and "antigen-binding portion" provided below. For example, in some embodiments, the human antibody may be a Fab fragment, a F(ab)$_2$ fragment, a Fd fragment having the V$_H$ and CH1 domains; a Fv fragment having the V$_L$ and V$_H$ domains of a single amino acid sequence of an antibody chain; a dAb fragment (Ward et al., 1989 Nature 341:544-546), which has a V$_H$ domain; or an isolated complementarity determining region (CDR), or a single chain Fv (scFv). In some embodiments, the human antibody may be conjugated to another atom or molecule. The human antibodies, as described above, may comprise part of a complex comprising at least two human antibodies, each of which specifically binds to human CTLA-4. In some embodiments, the complex may be polyvalent. The at least two antibodies can be linked to each other covalently or non-covalently. In some embodiments, the human antibodies described herein may also comprise part of an immunoconjugate or bispecific antibody.

In some embodiments, the human antibodies described herein may block or antagonize signals transduced by the human CTLA-4. Some of these antibodies may bind to an epitope on human CTLA-4 so as to inhibit CTLA-4 from interacting with a human B7 counterreceptor.

The present disclosure also provides nucleic acids which comprise a nucleotide sequence encoding the amino acid sequence of the human antibodies described herein. Also provided herein are nucleic acids comprising a nucleotide sequence chosen from SEQ ID NOs: 7, 9 and 11, which encodes an antibody heavy chain amino acid sequence. Further provided herein are nucleic acids comprising a light chain nucleotide sequence chosen from SEQ ID NOs: 1, 3 and 5, which encodes an antibody light chain amino acid sequence.

The present disclosure further provides pharmaceutical compositions which comprise the human antibodies described herein, and a pharmaceutically acceptable carrier. In some embodiments, the pharmaceutical compositions may further comprise one or more additional therapeutic agents. In some embodiments, the additional therapeutic agent or agents are effective to induce an immune response against tumors. In some embodiments, the additional therapeutic agent or agents are chemotherapeutic agents. Also in some embodiments, the additional therapeutic agent or agents are antibodies acting as immune checkpoint inhibitors, including but not limited to antibodies against PD-1, PD-1 L1, or PD-1 L2.

Also provided herein are methods of treating a CTLA-4 associated disease in a subject which comprise administering to the subject a therapeutically effective amount of the pharmaceutical compositions described herein. In some embodiments, the method further comprises administering to the subject one or more additional therapeutic agents. In some embodiments, the additional therapeutic agent or agents are effective to induce an immune response against tumors. In some embodiments, the additional therapeutic agent or agents are chemotherapeutic agents. Also in some embodiments, the additional therapeutic agent or agents are antibodies acting as immune checkpoint inhibitors, including but not limited to antibodies against PD-1, PD-1 L1, or PD-1 L2. Further in some embodiments, the additional therapeutic agent is a vaccine, including but not limited to a GM-CSF-modified tumor cell vaccine, or an antigen-loaded dendritic cell vaccine. In some embodiments, the CTLA-4 associated disease is a T cell medicated autoimmune disease. In some embodiments, the CTLA-4 associated disease can be cancer. Further in some embodiments, the CTLA-4 associated disease may be chosen from melanoma, non-small cell lung cancer, and prostate cancer.

The present disclosure also provides methods of using the antibodies in the present disclosure to detect in vitro or in vivo the presence of human CTLA-4 antigen in a sample for diagnosis of a CTLA-4 associated disease. In some embodiments, the CTLA-4 associated disease is a T cell mediated autoimmune disease. In some embodiments, the CTLA-4 associated disease can be cancer. Further in some embodiments, the CTLA-4 associated disease may be chosen from melanoma, non-small cell lung cancer, and prostate cancer.

Also provided in the present disclosure are methods of using the antibodies to inhibit, i.e., antagonize, the ability of CTLA-4 to bind ligands or to activate cells. In some embodiments, the methods may inhibit the ability of CTLA-4 to transmit a signal to the cell or to simulate, i.e. agonize, the effect of the ligand. In some embodiment, the methods may comprise contacting the antibodies described herein with a cell expressing a CTLA-4 peptide.

The present disclosure further provides methods of using the antibodies in the present disclosure to fabricate a medicament for treating a CTLA-4 associated disease. In some embodiments, the CTLA-4 associated disease is a T cell mediated autoimmune disease. In some embodiments, the CTLA-4 associated disease can be cancer. Further in some embodiments, the CTLA-4 associated disease may be chosen from melanoma, non-small cell lung cancer, and prostate cancer.

The present disclosure also provides methods for inducing, augmenting or prolonging an immune response to an antigen in a patient, comprising administering a therapeutically effective amount of a pharmaceutical composition described herein, wherein the pharmaceutical composition blocks binding of human CTLA-4 to human B7 ligands. In some embodiments, the antigen is a tumor antigen or an antigen from a pathogen. In some embodiments, the antigen is a Hepatitis B surface antigen.

BRIEF DESCRIPTION OF DRAWINGS

FIG. 2A shows alignment of nucleotide sequences of heavy chain variable regions from clones C2, C4, C10, C11, C12 and C13. All six sequences correspond to SEQ ID NO: 7.

FIG. 2B shows alignment of nucleotide sequences of light chain variable regions from clones C2, C4, C10, C11, C12 and C13. All six sequences correspond to SEQ ID NO: 1.

FIG. 3A shows alignment of nucleotide sequences of heavy chain variable regions from clones C6, C7 and C15. All three sequences correspond to SEQ ID NO: 11.

FIG. 3B shows alignment of nucleotide sequences of light chain variable regions from clones C6, C7 and C15. All three sequences correspond to SEQ ID NO: 5.

Figure 4C:
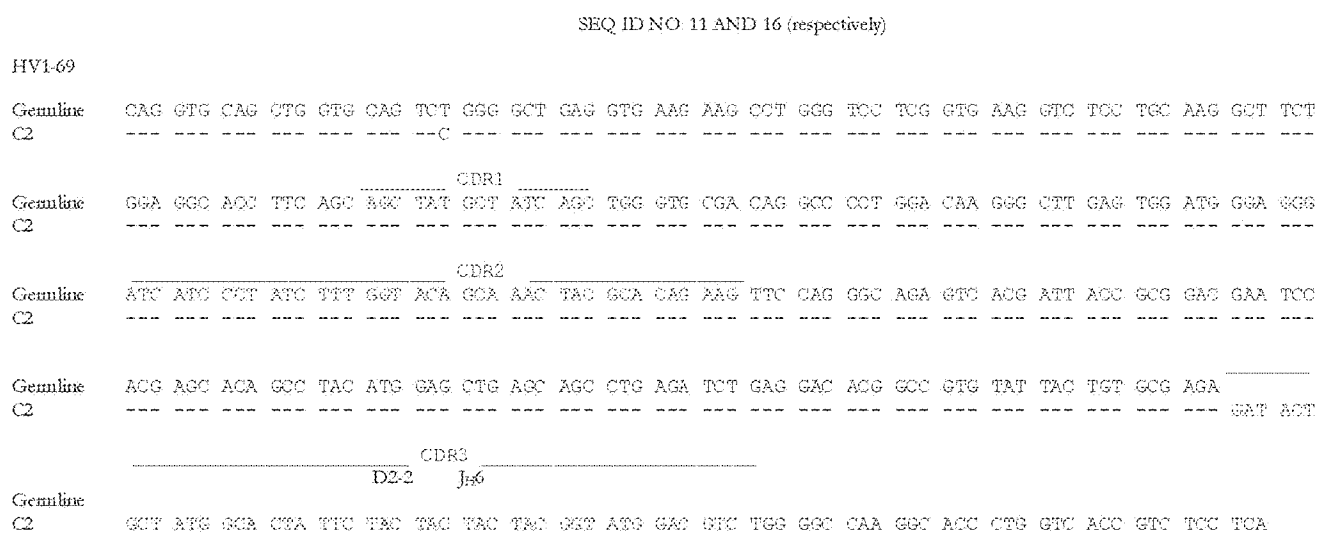

FIGS. 4A-4C show sequence alignments between nucleotide sequences of the heavy chain variable regions (VH) of anti-human CTLA-4 antibodies and their germline sequences. Particularly, FIG. 4A shows the anti-CTLA-4 antibody C2 (SEQ ID NO: 7) derived from the VH3-33 germline sequence (SEQ ID NO: 72). FIG. 4B shows the anti-CTLA-4 antibody C5 (SEQ ID NO: 9) derived from the VH1-46 germline sequence (SEQ ID NO: 14). FIG. 4C shows the anti-CTLA-4 antibody C15 (SEQ ID NO: 11) derived from the VH1-69 germline sequence (SEQ ID NO: 16). FIGS. 4A-4C also indicate the positions of the complementary determining residues (CDR1, CDR2 and CDR3) which are labeled. Dashes denote sequence identity.

FIGS. 5A-5C show sequence alignments between nucleotide sequences of the light chain variable regions (VL) of anti-human CTLA-4 antibodies. Particularly, FIG. 5A shows the anti-CTLA-4 antibody C2 (SEQ ID NO: 1) derived from the VL3-20 germline sequence (SEQ ID NO: 13). FIG. 5B shows the anti-CTLA-4 antibody C5 (SEQ ID NO: 3) derived from the VL2-23 germline sequence (SEQ ID NO: 15). FIG. 5C shows the anti-CTLA-4 antibody C15 (SEQ ID NO: 5) derived from the VL2-14 germline sequence (SEQ ID NO: 17). The positions of CDR1, CDR2 and CDR3 are labeled in FIGS. 5A-5C, dashes denote sequence identity.

FIG. 6 shows sequence alignments between the predicted amino acid sequences of the heavy chain variable regions (VH) of anti-human CTLA-4 antibodies described in FIG. 6 and the germline amino acid sequences. The anti-CTLA-4 antibody C2 (SEQ ID NO: 8) derived from the VH3-33 germline sequence (SEQ ID NO: 18) is shown at the top of the figure. The anti-CTLA-4 antibody C5 (SEQ ID NO: 10) derived from the VH1-46 germline sequence (SEQ ID NO: 20) is depicted in the middle of the figure, and the anti-CTLA-4 antibody C15 (SEQ ID NO: 12) derived from the VH1-69 germline sequence (SEQ ID NO: 22) is shown at the bottom of the figure.

FIG. 7 shows sequence alignments between the predicted amino acid sequences of the light chain variable regions (VL) of anti-human CTLA-4 antibodies and the germline amino acid sequences. The anti-CTLA-4 antibody C2 (SEQ ID NO: 2) derived from the VL3-20 germline sequence (SEQ ID NO: 19) is depicted at the top of the figure. The anti-CTLA-4 antibody C5 (SEQ ID NO: 4) derived from the VL2-23 germline sequence (SEQ ID NO: 21) is depicted in the middle of the figure, and the anti-CTA-4 antibody C15 (SEQ ID NO: 6) derived from the VL2-14 germline sequence (SEQ ID NO: 23) is shown at the bottom of the figure.

FIGS. 8A and 8B show full-length nucleotide sequences (SEQ ID NO: 60 and 62, respectively) and amino acid sequences (SEQ ID NO: 61 and 63, respectively) of heavy chain and light chain variable regions of clone C2. Particularly, FIG. 8A shows the full-length nucleotide sequence (SEQ ID NO: 60) and the full-length amino acid sequence (SEQ ID NO: 61) of the heavy chain variable regions of clone 2. FIG. 8B shows the full-length nucleotide sequence (SEQ ID NO: 62) and the full-length amino acid sequence (SEQ ID NO: 63) of the light chain variable regions of clone 2. Underlined are signal peptide sequences.

FIGS. 9A and 9B show full length nucleotide sequences (SEQ ID NO: 64 and 66, respectively) and amino acid sequences (SEQ ID NO: 65 and 67, respectively) of heavy chain and light chain variable regions of clone C5. Particularly, FIG. 9A shows the full-length nucleotide sequence (SEQ ID NO: 64) and the full-length amino acid sequence (SEQ ID NO: 65) of the heavy chain variable regions of clone 5. FIG. 9B shows the full-length nucleotide sequence (SEQ ID NO: 66) and the full-length amino acid sequence (SEQ ID NO: 67) of the light chain variable regions of clone 5. Underlined are signal peptide sequences.

FIGS. 10A and 10B show full length nucleotide sequences (SEQ ID NO: 68 and 70, respectively) and amino acid sequences (SEQ ID NO: 69 and 71, respectively) of heavy chain and light chain variable regions of clone C15. Particularly, FIG. 10A shows the full-length nucleotide sequence (SEQ ID NO: 68) and the full-length amino acid sequence (SEQ ID NO: 69) of the heavy chain variable regions of clone 15. FIG. 10B shows the full-length nucleotide sequence (SEQ ID NO: 70) and the full-length amino acid sequence (SEQ ID NO: 71) of the light chain variable regions of clone 15. Underlined are signal peptide sequences.

FIG. 13A shows C2 mAb's enhancement of PBMC IL-2 production when PBMC were stimulated with various concentrations of PHA. FIG. 13B shows C2 mAb-induced increase of PBMC IL-2 production when PBMC were stimulated by 1 ug/ml of PHA.

FIG. 15 shows human germline V gene segment nucleotide sequences according to some embodiments of the present disclosure.

DETAILED DESCRIPTION OF CERTAIN EMBODIMENTS

Figure 1:
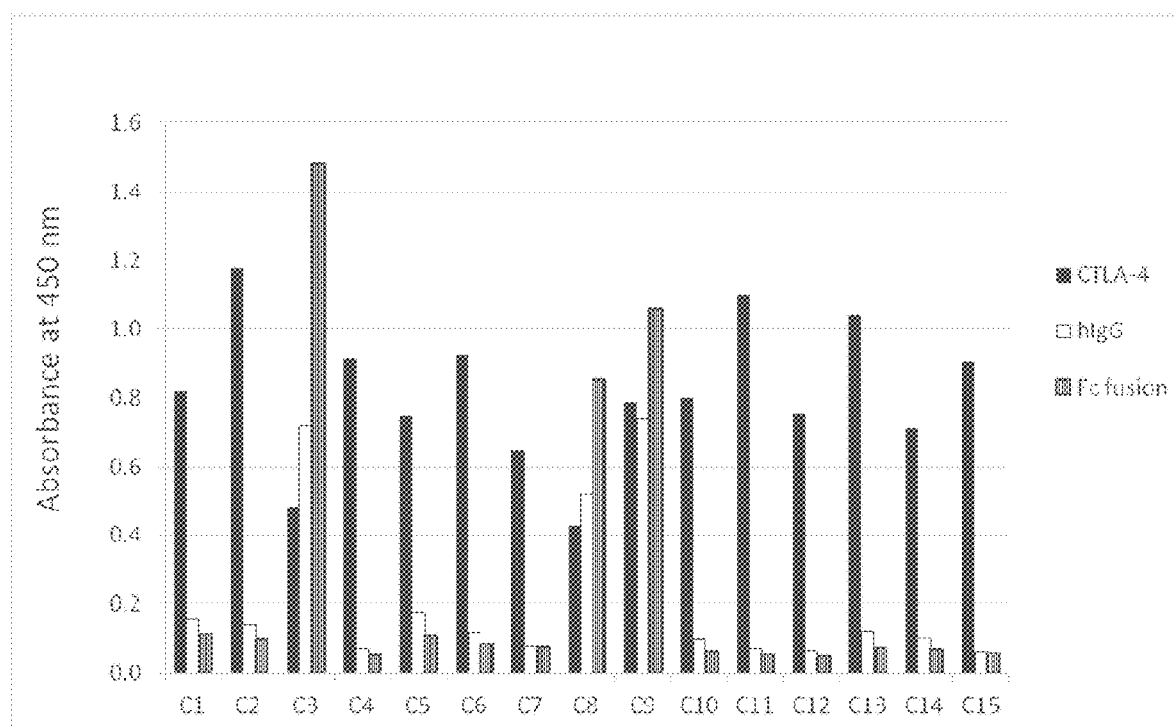
FIG. 1 shows the binding of scFv phages to recombinant human CTLA-4 (rhCTLA-4) proteins.

The present disclosure provides novel antibody-based therapies for treating and diagnosing diseases characterized by expression, particularly overexpression, or activation, particularly overactivation, of human CTLA-4 and/or related molecules. Therapies described herein employ human antibodies, particularly human monoclonal antibodies, that bind specifically to human CTLA-4. In certain embodiments, the antibodies described herein may be derived from particular heavy and light chain sequences, and/or comprise particular structural features such as CDR regions comprising particular amino acid sequences. The present disclosure also provides isolated antibodies, methods of making such antibodies, assays for detecting such antibodies, immunoconjugates and bispecific molecules comprising such antibodies, and pharmaceutical compositions comprising the antibodies. The present disclosure also relates to methods of using the antibodies to inhibit, i.e., antagonize, the ability of CTLA4 to bind ligands or to activate cells, e.g., by inhibiting its ability to transmit a signal to the cell or to simulate, i.e. agonize, the effect of the ligand.

In order that the present disclosure may be more readily understood, certain terms are first defined. These definitions should be read in light of the remainder of the disclosure and as understood by a person of ordinary skill in the art. Unless defined otherwise, all technical and scientific terms used herein have the same meanings as commonly understood by a person of ordinary skill in the art.

Additional definitions are set forth throughout the detailed description.

The articles "a" and "an," as used herein, should be understood to mean "at least one," unless clearly indicated to the contrary.

The phrase "and/or," as used herein, should be understood to mean "either or both" of the elements so conjoined, i.e., elements that are conjunctively present in some cases and disjunctively present in other cases. Other elements may optionally be present other than the elements specifically identified by the "and/or" clause, whether related or unrelated to those elements specifically identified unless clearly indicated to the contrary. Thus, as a non-limiting example, a reference to "A and/or B," when used in conjunction with open-ended language such as "comprising" can refer, in one embodiment, to A without B (optionally including elements other than B); in another embodiment, to B without A (optionally including elements other than A); in yet another embodiment, to both A and B (optionally including other elements).

As used herein, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements.

In general, the term "or" as used herein shall only be interpreted as indicating exclusive alternatives (i.e. "one or the other but not both") when preceded by terms of exclusivity, such as "either," "one of," "only one of," or "exactly one of."

As used herein, the phrase "at least one" in reference to a list of one or more elements should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified.

Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

As used herein, all transitional phrases such as "comprising," "including," "carrying," "having," "containing," "involving," "holding," and the like are to be understood to be open-ended, i.e., to mean including but not limited to.

Only the transitional phrases "consisting of" and "consisting essentially of" shall be closed or semi-closed transitional phrases, respectively, as used in the field of patent law.

The term "epitope" means a protein determinant capable of specific binding to an antibody. Epitopes may include chemically active surface groupings of molecules such as amino acids or sugar side chains and may have specific three dimensional structural characteristics, as well as specific charge characteristics. Conformational and nonconformational epitopes are distinguished in that the binding to the former but not the latter is lost in the presence of denaturing solvents.

The term "antigen" refers to a molecule, e.g., CTLA4, or a portion of a molecule, capable of being specifically bound by a selective binding agent, such as an antigen binding protein (including, e.g., an antibody or immunological functional fragment thereof), and/or capable of being used in an animal to produce antibodies capable of binding to that molecule or the portion thereof. An antigen may possess one or more epitopes that are capable of interacting with different antigen binding proteins, e.g., antibodies.

The term "antibody" encompasses any moiety having immunoglobin-like antigen binding function. The term includes whole antibody molecules, single chain antibodies, camelid antibodies including, e.g., nanobodies, phage-display binding constructs, as well as bispecific antibodies, antibody conjugates, chimeric antibodies, and the like. A naturally occurring antibody is a glycoprotein comprising at least two heavy (H) chains and two light (L) chains interconnected by disulfide bonds. Each heavy chain is comprised of a heavy chain variable region (abbreviated herein as $V_H$) and a heavy chain constant region. The heavy chain constant region is comprised of three domains, CH1, CH2 and CH3. There are two types of light chain: lambda and kappa. Each light chain is comprised of a light chain variable region (abbreviated herein as $V_L$) and a light chain constant region. The light chain constant region is comprised of one domain, $C_L$. The $V_H$ and $V_L$ regions can be further subdivided into regions of hypervariability, termed complementarity determining regions (CDR), interspersed with regions that are more conserved, termed framework regions (FR). As found in nature, each $V_H$ and $V_L$ is composed of three CDRs and four FRs arranged from amino-terminus to carboxy-terminus in the following order: FR1, CDR1, FR2, CDR2, FR3, CDR3, FR4. The variable regions of the heavy and light chains contain a binding domain that interacts with an antigen. The constant regions of the antibodies may mediate the binding of the immunoglobulin to host tissues or factors, including various cells of the immune system (e.g., effector cells) and the first component (Clq) of the classical complement system. An antibody may be monoclonal or polyclonal. In some embodiments, the antibody is a human antibody.

In some embodiments, the antibody is non-human (e.g., mouse), chimeric, or humanized.

The terms "antigen-binding fragment," "antigen-binding portion," and "antigen portion" are used interchangeably herein and refer to one or more fragments of an antibody having the ability to specifically bind to an antigen (e.g., a portion of CTLA-4). It has been shown that the antigen-binding function of an antibody can be performed by fragments of a full-length antibody molecule. Examples of antigen-binding portions include a Fab fragment, which is a monovalent fragment consisting of the $V_L$, $V_H$, $C_L$ and CH1 domains; a F(ab)$_2$ fragment, which is a bivalent fragment comprising two Fab fragments linked by a disulfide bridge at the hinge region; a Fd fragment having the $V_H$ and CH1 domains; a Fv fragment having the $V_L$ and $V_H$ domains of a single amino acid sequence of an antibody chain; a dAb fragment (Ward et al., 1989 Nature 341:544-546), which has a $V_H$ domain; and an isolated complementary determining region (CDR).

Antigen-binding portions may be isolated fragments or may be conjugated to one or more another atoms or molecules, such as chemical or biological moieties, or fragments attached to non-traditional immunoglobulin-derived frameworks or scaffolds, including but not limited to, e.g., ankyrins, fibronectins, domain antibodies, lipocalin, small modular immuno-pharmaceuticals, maxybodies, nanobodies, protein A, affilin, gamma-crystallin and ubiquitin, and other contemplated scaffolds known to one skilled in the art.

Furthermore, although in a naturally occurring antibody molecule there are two chains having Fv domains, $V_L$ and $V_H$, which are encoded by separate genes, they can be joined using recombinant methods, by a synthetic linker that enables them to be recombinantly expressed as a single protein chain in which the $V_L$ and $V_H$ regions form one monovalent molecule (known as single chain Fv (scFv); see e.g., Bird et al., 1988 Science 242:423-426; and Huston et al., 1988 Proc. Natl. Acad. Sci. 85:5879-5883). Such single chain antibodies are also encompassed within the term "antibody." These single chain antibodies may be obtained using conventional techniques known to those of skill in the art, and may be screened for utility in the same manner as are intact antibodies.

An "isolated antibody" refers to an antibody that is substantially free of other antibodies having different antigenic specificities (e.g., an isolated antibody that specifically binds to a determinant that is a set of amino acids on CTLA-4 is substantially free of antibodies that bind specifically and substantially to antigens other than CTLA-4). An isolated antibody that specifically binds to a CTLA-4 protein such as human CTLA-4 may, however, have cross-reactivity to other antigens, such as to CTLA-4 molecules from other species, or to proteins having a high amount of homology to a human CTLA-4 amino acid sequence. Moreover, an isolated antibody may be substantially free of other cellular material and/or chemicals.

The terms "monoclonal antibody" or "monoclonal antibody composition" refer to a preparation of antibody molecules, all of which share a single molecular composition. A monoclonal antibody composition thus displays a single binding specificity and affinity for a particular epitope.

As used herein, the term "polyclonal antibody" refers to an antibody composition having a heterogeneous antibody population. Polyclonal antibodies are often derived from the pooled serum from immunized animals or from selected humans.

The term "human antibody", as used herein, is intended to include antibodies having variable regions in which at least one and generally both the framework and CDR regions are derived from sequences of human origin. Furthermore, if the antibody contains a constant region, the constant region also is derived from such human sequences, e.g., human germline sequences, or mutated versions of human germline sequences. The human antibodies of the disclosure may include amino acid residues not encoded by human sequences (e.g., mutations such as substitutions introduced by random or site-specific mutagenesis in vitro or by somatic mutation in vivo).

The term "human monoclonal antibody" refers to a human antibody that is also a "monoclonal antibody." In some embodiments, the human monoclonal antibodies are produced by hybridoma cells, which include a B cell obtained from a transgenic nonhuman animal, e.g., a transgenic mouse, having a genome comprising a heavy chain transgene, generally of human origin, and a light chain transgene, generally of human origin, fused to an immortalized cell, generally of human origin.

The term "recombinant human antibody", as used herein, includes human antibodies that are prepared, expressed, created or isolated by recombinant means. This includes antibodies isolated from an animal (e.g., a mouse) that is transgenic or transchromosomal for human immunoglobulin genes or a hybridoma prepared therefrom; antibodies isolated from a host cell transformed to express the human antibody, e.g., from a transfectoma; antibodies isolated from a recombinant, combinatorial human antibody library; and antibodies prepared, expressed, created or isolated by any other means that involve splicing of all or a portion of one or more human immunoglobulin gene sequences to other DNA sequences. Such recombinant human antibodies have variable regions in which the framework and CDR regions are derived from human germline immunoglobulin sequences. In certain embodiments, however, such recombinant human antibody sequences may be altered by in vitro mutagenesis, or, when an animal transgenic for human Ig sequences is used, by in vivo somatic mutagenesis, so that the amino acid sequences of the $V_H$ and $V_L$ regions of the recombinant human antibodies are sequences that, while derived from and related to human germline $V_H$ and $V_L$ sequences, may differ somewhat from those that naturally exist within the human antibody germline repertoire in vivo.

The phrases "an antibody recognizing an antigen" and "an antibody specific for an antigen" are used interchangeably herein with the term "an antibody which binds specifically to an antigen."

In some embodiments, the human antibodies to human CTLA-4 described herein may block or antagonize signals transduced by the human CTLA4. Some of these antibodies may bind to an epitope on human CTLA-4 so as to inhibit CTLA-4 from interacting with a human B7 counterreceptor. Because interaction of human CTLA-4 with human B7 transduces a signal leading to inactivation of T-cells bearing the human CTLA-4 receptor, antagonism of the interaction effectively induces, augments, or prolongs the activation of T cells bearing the human CTLA-4 receptor, thereby prolonging or augmenting an immune response. A "blocking antibody" refers to an antibody that reduces the binding of soluble human CTLA4 to cell-expressed human B7 ligand by at least 10%, such as by 20%, 30%, 40%, 50%, 60%, 70%, 80%, 90%, 99% or 99.9%, or any range that begins and ends with any of the above percentages, under conditions in which the ratio of antibody combining site to human CTLA-4 ligand binding site is greater than 1:1 and the concentration of antibody is greater than 10 nM.

As used herein, an antibody that "specifically binds to human CTLA-4" refers to an antibody that binds to human CTLA-4 with a $K_D$ of $1\times10^{-7}$ M or less, such as $1\times10^{-8}$ M or less, $1\times10^{-9}$ M or less. As used herein, the term "cross-reactivity" refers to a situation in which an antibody or population of antibodies detectably binds not only to its intended antigen, but also to epitopes on other antigens. This can be caused either by low avidity or specificity of the antibody or by multiple distinct antigens having identical or very similar epitopes. Cross reactivity is sometimes desirable when one wants general binding to a related group of antigens or when attempting cross-species labeling if the antigen epitope sequence is not highly conserved in evolution.

The term "nucleic acid molecule", as used herein, refers to a polymer of nucleotides including, e.g., DNA molecules and RNA molecules. Such polymers of nucleotides may contain natural and/or non-natural nucleotides. A nucleic acid molecule may be single-stranded or double-stranded.

The nucleic acids may be present in whole cells, in a cell lysate, or in a partially purified or substantially pure form. A nucleic acid is "isolated" or "rendered substantially pure" when purified away from other cellular components or other contaminants, e.g., other cellular nucleic acids or proteins, by standard techniques, including alkaline/SDS treatment, CsCl banding, column chromatography, agarose gel electrophoresis and others well known in the art. See, F. Ausubel, et al., ed. Current Protocols in Molecular Biology, Greene Publishing and Wiley Interscience, New York (1987). The term "degenerate" when applied to a reference "nucleic acid molecule" herein refers to a nucleic acid molecule that encodes the same amino acid sequence as the reference nucleic acid molecule, but that has a different nucleotide sequence from the reference nucleic acid molecule. For example, a nucleic acid sequence that is degenerate to SEQ ID NO:1 herein encodes the same amino acid sequence as encoded by SEQ ID NO:1, but has itself a different nucleic acid sequence than SEQ ID NO:1.

The term "substantially identical," in the context of two nucleic acids or polypeptides refers to two or more sequences or subsequences that have at least about 80%, for example, at least about 85%, about 90%, about 95%, about 98%, or about 99% nucleotide or amino acid residue identity with a specific reference sequence, when compared and aligned for maximum correspondence, as measured using the following sequence comparison method and/or by visual inspection. For example, the disclosure provides nucleic acids having sequences that are substantially identical to SEQ ID NO:1, SEQ ID NO:2. The "substantial identity" can exist over a region of sequence that is at least about 50 residues in length, over a region of at least about 100 residues, or over a region at least about 150 residues, or over the full length of the two sequences to be compared. As described below, any two antibody sequences can only be aligned in one way, by using the numbering scheme in Kabat. Amino acids from the variable regions of the mature heavy and light chains of immunoglobulins are designated Hx and Lx respectively, where x is a number designating the position of an amino acid according to the scheme of Kabat, Sequences of Proteins of Immunological Interest (National Institutes of Health, Bethesda, Md., 1987 and 1991). Kabat lists many amino acid sequences for antibodies for each subgroup, and lists the most commonly occurring amino acid for each residue position in that subgroup to generate a consensus sequence. Kabat uses a method for assigning a residue number to each amino acid in a listed sequence, and this method for assigning residue numbers has become standard in the field. Kabat's scheme is extendible to other antibodies not included in his compendium by aligning the antibody in question with one of the consensus sequences in Kabat by reference to conserved amino acids. The use of the Kabat numbering system readily identifies amino acids at equivalent positions in different antibodies. For example, an amino acid at the 150 position of a human antibody occupies the equivalent position to an amino acid position L50 of a mouse antibody. Likewise, nucleic acids encoding antibody chains are aligned when the amino acid sequences encoded by the respective nucleic acids are aligned according to the Kabat numbering convention.

A nucleic acid is "operably linked" when it is placed into a functional relationship with another nucleic acid sequence. For instance, a promoter or enhancer is operably linked to a coding sequence if it affects the transcription of the sequence. With respect to transcription of regulatory sequences, operably linked means that the DNA sequences being linked are contiguous and, where necessary to join two protein coding regions, contiguous and in reading frame.

The term "vector", as used herein, refers to a nucleic acid molecule capable of transporting another nucleic acid to which it has been linked. One type of vector is a "plasmid", which refers to a circular double stranded DNA loop into which additional DNA segments may be ligated. Another type of vector is a viral vector, wherein additional DNA segments may be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) can be integrated into the genome of a host cell upon introduction into the host cell, and thereby are replicated along with the host genome. Moreover, certain vectors are capable of directing the expression of genes to which they are operatively linked.

Such vectors are referred to herein as "recombinant expression vectors" (or simply, "expression vectors"). In general, expression vectors of utility in recombinant DNA techniques are often in the form of plasmids. In the present specification, "plasmid" and "vector" may be used interchangeably as the plasmid is the most commonly used form of vector. However, other forms of expression vectors are also encompassed herein, such as phagemid vectors (e.g., replication defective retroviruses, adenoviruses and adeno-associated viruses), which serve equivalent functions.

The term "recombinant host cell" (or simply "host cell"), as used herein, refers to a cell into which a recombinant expression vector has been introduced. Such terms refer not only to the particular subject cell but to the progeny of such a cell. Because certain modifications may occur in succeeding generations due to either mutation or environmental influences, such progeny may not, in fact, be identical to the parent cell, but are still included within the scope of the term "host cell" as used herein. Recombinant host cells include, for example, transfectomas, such as CHO cells, NS/0 cells, and lymphocytic cells.

The phrase "immune cell response" refers to the response of immune system cells to external or internal stimuli (e.g., antigen, cytokines, chemokines, and other cells) producing biochemical changes in the immune cells that result in, for example, immune cell migration, killing of target cells, phagocytosis, production of antibodies, other soluble effectors of the immune response, and the like.

The terms "T lymphocyte response" and "T lymphocyte activity" are used here interchangeably to refer to the component of immune response dependent on T lymphocytes (e.g., the proliferation and/or differentiation of T lymphocytes into helper, cytotoxic killer, or suppressor T lymphocytes, the provision of signals by helper T lymphocytes to B lymphocytes that cause or prevent antibody production, the killing of specific target cells by cytotoxic T lymphocytes, and the release of soluble factors such as cytokines that modulate the function of other immune cells).

The term "immune response" refers to the concerted action of lymphocytes, antigen presenting cells, phagocytic cells, granulocytes, and soluble macromolecules (including, e.g., antibodies, cytokines, and complement) produced by the above cells or tissues, e.g., the liver, that results in selective damage to, destruction of, or elimination from the human body of invading pathogens, cells or tissues infected with pathogens, cancerous cells, or, in cases of autoimmunity or pathological inflammation, normal human cells or tissues.

Components of an immune response may be detected in vitro by various methods. For example, (1) cytotoxic T lymphocytes can be incubated with radioactively labeled target cells and the lysis of these target cells detected by the release of radioactivity, (2) helper T lymphocytes can be incubated with antigens and antigen presenting cells and the synthesis and secretion of cytokines measured by standard methods (Windhagen A; et al., 1995, *Immunity* 2 (4): 373-80), (3) antigen presenting cells can be incubated with whole protein antigen and the presentation of that antigen on MHC detected by either T lymphocyte activation assays or biophysical methods (Harding et al., 1989, *Proc. Natl. Acad Sci.*, 86: 42304), (4) mast cells can be incubated with reagents that cross-link their Fc-epsilon receptors and histamine release measured by enzyme immunoassay (Siraganian, et al., 1983, *TIPS* 4: 432-437). Similarly, products of an immune response in either a model organism (e.g., mouse) or a human patient can also be detected by various methods that are well known to those of ordinary skill in the art. For example, (1) the production of antibodies in response to vaccination can be readily detected by standard methods currently used in clinical laboratories, e.g., an ELISA; (2) the migration of immune cells to sites of inflammation can be detected by scratching the surface of skin and placing a sterile container to capture the migrating cells over scratch site (Peters et al., 1988, *Blood* 72: 1310-5); (3) the proliferation of peripheral blood mononuclear cells in response to mitogens or mixed lymphocyte reaction can be measured using $^3$H-thymidine; (4) the phagocitic capacity of granulocytes, macrophages, and other phagocytes in PBMCs can be measured by placing PBMCs in wells together with labeled particles (Peters et al., 1988 *Blood* 72: 1310-5)); and (5) the differentiation of immune system cells can be measured by labeling PBMCs with antibodies to CD molecules such as CD4 and CD8 and measuring the fraction of the PBMCs expressing these markers.

As used herein, the phrase "signal transduction pathway" or "signal transduction event" refers to at least one biochemical reaction, but more commonly a series of biochemical reactions, which result from interaction of a cell with a stimulatory compound or agent. Thus, the interaction of a stimulatory compound with a cell generates a "signal" that is transmitted through the signal transduction pathway, ultimately resulting in a cellular response, e.g., an immune response described above.

As used herein, the phrase "cell surface receptor" includes molecules and complexes of molecules capable of receiving a signal and the transmission of such a signal across the plasma membrane of a cell. An example of a "cell surface receptor" described herein is the T cell receptor (TCR) or the B7 ligands of CTLA-4.

A signal transduction pathway in a cell can be initiated by interaction of a cell with a stimulator that is inside or outside of the cell. If an exterior (i.e., outside of the cell) stimulator (e.g., an MHC-antigen complex on an antigen presenting cell) interacts with a cell surface receptor (e.g., a T cell receptor), a signal transduction pathway can transmit a signal across the cell's membrane, through the cytoplasm of the cell, and in some instances into the nucleus. If an interior (e.g., inside the cell) stimulator interacts with an intracellular signal transduction molecule, a signal transduction pathway can result in transmission of a signal through the cell's cytoplasm, and in some instances into the cell's nucleus.

Signal transduction can occur through, e.g., the phosphorylation of a molecule; non-covalent allosteric interactions; complexing of molecules; the conformational change of a molecule; calcium release; inositol phosphate production; proteolytic cleavage; cyclic nucleotide production and diacylglyceride production. Typically, signal transduction occurs through phosphorylating a signal transduction molecule.

The term "nonspecific T cell activation" refers to the stimulation of T cells independent of their antigenic specificity.

The term "pharmaceutically acceptable carrier," as used herein, refers to solid or liquid filler, diluent or substance which may be safely used in the administration of the antibodies described herein (for example, systemic or topical administration). Pharmaceutically acceptable carriers for systemic administration that may be incorporated in the composition of the disclosure include sugar, starches, cellulose, vegetable oils, buffers, polyols and alginic acid, among others known to one of ordinary skill in the art. Representative carriers include acacia, agar, alginates, hydroxyalkylcellulose, hydroxypropyl methylcellulose, carboxymethylcellulose, carboxymethylcellulose sodium, carrageenan, powdered cellulose, guar gum, cholesterol, gelatin, gum agar, gum arabic, gum karaya, gum ghatti, locust bean gum, octoxynol 9, oleyl alcohol, pectin, poly(acrylic acid) and its homologs, polyethylene glycol, polyvinyl alcohol, polyacrylamide, sodium lauryl sulfate, poly (ethylene oxide), polyvinylpyrrolidone, glycol monostearate, propylene glycol monostearate, xanthan gum, tragacanth, sorbitan esters, stearyl alcohol, starch and its modifications, among others known to one of ordinary skill in the art.

The terms "therapeutically effective amount" or "effective amount" refer to an amount of the pharmaceutical composition described herein effective to "treat" a disease or disorder in a subject. In the case of cancer, the therapeutic effective amount of the drug may reduce the number of cancer cells; reduce the tumor size; inhibit (i.e., slow to some extent or stop) cancer cell infiltration into peripheral organs; inhibit (i.e., slow to some extent or stop) tumor metastasis; inhibit, to some extent, tumor growth; and/or relieve to some extent one or more of the symptoms associated with the cancer. The skilled artisan would understand that the effective amount of the compound or composition administered herein varies and can be readily determined based on a number of factors such as the disease or condition being treated, the stage of the disease, the age and health and physical condition of the mammal being treated, the severity of the disease, the particular compound being administered, and the like.

As used herein, to "treat" means reducing the frequency of symptoms of a disease that are experienced by a patient (i.e., tumor growth and/or metastasis, or other effect mediated by the numbers and/or activity of immune cells, and the like). The term includes the administration of the compounds or agents of the present disclosure to prevent or delay the onset of the symptoms, complications, or biochemical indicia of a disease (e.g., elevation of PSA level), alleviating the symptoms or arresting or inhibiting further development of the disease, condition, or disorder. Treatment may be prophylactic (to prevent or delay the onset of the disease, or to prevent the manifestation of clinical or subclinical symptoms thereof) or therapeutic suppression or alleviation of symptoms after the manifestation of the disease.

The term "CTLA-4 associated disease" refers to a disease characterized by expression, particularly over-expression, or activation, particularly overactivation, of human CTLA-4.

The term "subject" refers to mammals such as human beings and non-human primates, as well as experimental animals such as rabbits, rats, and mice, and other animals. Animals include all vertebrates, e.g., mammals and non-mammals, such as sheep, dogs, cows, chickens, amphibians, and reptiles.

As used herein, the terms "administer" or "administration" refer to the act of injecting or otherwise physically delivering a substance as it exists outside the body (e.g., a formulation of the invention) into a patient, such as by oral, mucosal, intradermal, intravenous, subcutaneous, intramuscular delivery and/or any other method of physical delivery described herein or known in the art. When a disease, or a symptom thereof, is being treated, administration of the substance typically occurs after the onset of the disease or symptoms thereof. When a disease or symptoms thereof, are being prevented, administration of the substance typically occurs before the onset of the disease or symptoms thereof.

The term "immune checkpoint inhibitor" as used herein refers to an agent involved in inhibitory pathways in the immune system that are responsible for maintaining self-tolerance and modulating the degree of immune system response to minimize peripheral tissue damage.

The term "tumor antigen" refers to a differentiation antigen expressed in tumors and in cells from which the tumors arose, for example melanocyte antigens gplOO, MAGE/BAGE/GAGE, Yo, GAD, MART-I/melan-A, Trp-2, Heat Shock Proteins, and many others. The tumor antigen as described herein can be targets of tumor specific T-cells found in the host. The tumor antigen may also include telomerase, which is required for the synthesis of telomeres of chromosomes and expressed in more than 85% of human cancers and in only a limited number of somatic tissues (Kim et al. (1994) *Science*, 266:2011-2013).

The term "pathogen" as used herein refers to a biological agent that causes disease to its host. For example, the pathogen can be bacteria, virus, fungi or parasites. The pathogen can also be an HIV. Various aspects of the invention are described in further detail in the following subsections.

I. Production of Human Antibodies to Human CTLA-4

Human antibodies or human monoclonal antibodies described herein can be produced by a variety of techniques, e.g., somatic cell hybridization techniques of Kohler and Milstein, Nature 256:495 (1975). Other techniques for producing monoclonal antibody can also be employed, e.g., viral or oncogenic transformation of B-lymphocytes or phage display techniques using libraries of human antibody genes.

Human monoclonal antibodies directed against CTLA-4 can also be prepared using phage display methods for screening libraries of human immunoglobulin genes. See for example: U.S. Pat. Nos. 5,223,409; 5,403,484; and U.S. Pat. No. 5,571,698 to Ladner et al.; U.S. Pat. Nos. 5,427,908 and 5,580,717 to Dower et al.; U.S. Pat. Nos. 5,969,108 and 6,172,197 to McCafferty et al.; and U.S. Pat. Nos. 5,885,793; 6,521,404; 6,544,731; 6,555,313; 6,582,915 and 6,593,081 to Griffiths et al., which describe such methods.

Construction of a Library and Panning Using CTLA-4

A phage display library can be formed by cloning the antibody variable region genes described herein into a phage display vector encoding a phage coat protein that is normally expressed on the outer surface of the phage. A fusion protein containing the antibody variable regions and the phase coat protein is expressed, transported to the outer surface, assembled, and displayed on the outer surface of the phage. The phage most frequently used for display libraries are bacteriophage, particularly filamentous phage, and especially phage M13, Fd or F1.

The phase display antibody library is then panned against human CTLA-4 bound to a solid phase. After surface is washed to remove nonbinding phage antibodies, bound phages were eluted for infection and production of fresh phage antibodies that are used in the next round of panning. Repeated rounds of panning lead to the enrichment of phage antibodies that are specific to CTLA-4.

The phage display library of antibodies can be made in single chain form or double chain form. Single chain antibody libraries may comprise the heavy chain or light chain of an antibody alone or the variable domain thereof. However, the members of single-chain antibody libraries are more often formed from a fusion of heavy and light chain variable domains separated by a peptide spacer within a single contiguous protein which is fused to a phage coat protein.

Diversity of antibody libraries may arise from obtaining antibody variable domain-encoding sequences from a natural source, e.g., a nonclonal population of immunized or unimmunized B cells. Alternatively, diversity can be introduced by artificial mutagenesis of nucleic acids encoding antibody chains before or after inserted into a display vector. Such mutagenesis can occur in the course of PCR or can be introduced before or after PCR.

Repertoires of antibody fragments can be constructed by combining amplified $V_H$ and $V_L$ Sequences together in several ways.

Production of Human Monoclonal Antibodies to CTLA-4

Human antibodies described herein can be produced in a host cell transfectoma using, for example, a combination of recombinant DNA techniques and gene transfection methods, see e.g. Morrison, S. (1985) *Science* 229:1202

For example, to express the antibodies, DNAs encoding partial or full-length light and heavy chains, can be obtained by standard molecular biology techniques (e.g., PCR amplification, site directed mutagenesis) and can be inserted into expression vectors such that the genes are operatively linked to transcriptional and translational control sequences. The expression vector and expression control sequences are chosen to be compatible with the expression host cell used. The antibody light chain gene and the antibody heavy chain gene can be inserted into separate vectors or, in some embodiments, both genes are inserted into the same expression vector. The antibody genes can be inserted into the expression vector by standard methods (e.g., ligation of complementary restriction sites on the antibody gene fragment and vector, or blunt end ligation if no restriction sites are present). The light and heavy chain variable regions of the antibodies described herein can be used to create full-length antibody genes of any antibody isotype by inserting them into expression vectors already encoding heavy chain constant and light chain constant regions of the desired isotype such that the $V_H$ segment is operatively linked to the $C_H$ segment(s) within the vector and the $V_L$ segment is operatively linked to the $C_L$ segment within the vector. Additionally, a recombinant expression vector can encode a signal peptide that facilitates secretion of the antibody chain from a host cell. The antibody chain genes can be cloned into vectors such that the signal peptide is linked in-frame to the amino terminus of the antibody chain gene. Or alternatively, a signal peptide gene can be operatively linked to the antibody chain gene. The signal peptide can be an immunoglobulin signal peptide or a heterologous signal peptide (i.e., a signal peptide from a non-immunoglobulin protein).

In addition to the antibody chain genes, the recombinant expression vectors described herein may carry regulatory sequences that control the expression of the antibody chain genes in a host cell. The term "regulatory sequence" includes promoters, enhancers, and other expression control elements (e.g., polyadenylation signals) that control the transcription or translation of the antibody chain genes. Such regulatory sequences are described, for example, in Goeddel; Gene Expression Technology. Methods in Enzymology 185, Academic Press, San Diego, Calif. (1990). The design of the expression vector, including the selection of regulatory sequences, may depend on such factors as the choice of the host cell to be transformed, the level of expression of protein desired, etc. Exemplary regulatory sequences for mammalian host cell expression include viral elements that direct high levels of protein expression in mammalian cells, such as promoters and/or enhancers derived from cytomegalovirus (CMV), Simian Virus 40 (SV40), adenovirus (e.g., the adenovirus major late promoter (AdMLP)), and polyoma. In some embodiments, nonviral regulatory sequences may be used, such as the ubiquitin promoter or β-globin promoter.

In addition to the antibody chain genes and regulatory sequences, the recombinant expression vectors described herein may carry additional sequences, such as sequences that regulate replication of the vector in host cells (e.g., origins of replication) and selectable marker genes. The selectable marker gene facilitates selection of host cells into which the vector has been introduced (see e.g., U.S. Pat. Nos. 4,399,216, 4,634,665 and 5,179,017, all by Axel et al.). For example, the selectable marker gene may confer resistance to drugs, such as G418, hygromycin, or methotrexate, on a host cell into which the vector has been introduced. Exemplary selectable marker genes include the dihydrofolate reductase (DHFR) gene (for use in dhfr-host cells with methotrexate selection/amplification) and the neo gene (for G418 selection).

For expression of the light and heavy chains, the expression vector(s) encoding the heavy and light chains may be transfected into a host cell by standard techniques. The various forms of the term "transfection" encompass a wide variety of techniques commonly used for the introduction of exogenous DNA into a prokaryotic or eukaryotic host cell, e.g., electroporation, calcium-phosphate precipitation, DEAE-dextran transfection and the like. It is possible to express the antibodies described herein in either prokaryotic or eukaryotic host cells.

In some embodiments, the antibodies may be expressed in eukaryotic cells, such as mammalian host cells. Exemplary mammalian host cells for expressing the recombinant antibodies described herein include Chinese Hamster Ovary (CHO cells), including dhfr-CHO cells, described in Urlaub and Chasin, 1980 *Proc. Natl. Acad Sc. USA* 77:4216-4220 used with a DH FR selectable marker, e.g., as described in R. J. Kaufman and P. A. Sharp, 1982 *Mol. Biol.* 159:601-621, NSO myeloma cells, COS cells, and SP2 cells. In some embodiments, the GS gene expression system shown in WO 87/04462, WO 89/01036 and EP 338,841 may be used with NSO myeloma cells. When recombinant expression vectors encoding antibody genes are introduced into mammalian host cells, the antibodies may be produced by culturing the host cells for a period of time sufficient to allow for expression of the antibody in the host cells or secretion of the antibody into the culture medium in which the host cells are grown. Antibodies can be recovered from the culture medium using standard protein purification methods.

In some embodiments, the cloned antibody genes can be expressed in other expression systems, including prokaryotic cells, such as microorganisms, e.g. *E. coli* (e.g., for the production of scFv antibodies), algi, as well as insect cells. Furthermore, the antibodies can be produced in transgenic non-human animals, such as in milk from sheep and rabbits or eggs from hens, or in transgenic plants. See e.g. Verma, R., et al. (1998) *J. Immunol. Meth.* 216:165-181; Pollock, et al. (1999) *J. Immmnol. Meth.* 231:147-157; and Fischer, R., et al. (1999) *Biol. Chem.* 380:825-839.

To create an scFv gene, the $V_H$- and $V_L$-encoding DNA fragments may be operatively linked to another fragment encoding a flexible linker, e.g., the amino acid sequence (Gly4-Ser)$_3$, such that the $V_H$ and $V_L$ sequences can be expressed as a contiguous single-chain protein, with the $V_L$ and $V_H$ regions joined by the flexible linker (see e.g., Bird et al.; 1988 *Science* 242:423-426; Huston et at., 1988 *Proc. Natl. Acad Sci. USA* 85:5879-5883; McCafferty et al., 1990 *Nature* 348:552-554).

Detailed procedures to generate fully human monoclonal antibodies to CTLA-4 according to some embodiments of the present disclosure are described in the Examples below. For example, dhfr-CHO cells may be transfected by electroporation with the expression vectors carrying heavy chain and light chain genes and limit-dilution plated on 96-well plates. Transfected cells may be cultured in OptiCHO medium containing Methotrexate. Cell lines expressing human monoclonal antibodies to CTLA-4 may be selected by ELISA screening wells in which cell colonies are formed.

To purify anti-CTLA-4 human monoclonal antibodies, selected CHO cell clones can be grown in two-liter spinner-flasks for monoclonal antibody purification. Supernatants can be filtered and concentrated before affinity chromatography with commercially available protein A-sepharose (e.g., Pharmacia, Piscataway, N.J.). Eluted IgG can be checked by gel electrophoresis and high performance liquid chromatography to ensure purity. The buffer solution can be exchanged into PBS, and the concentration can be determined by OD280 using 1.54 extinction coefficient. The monoclonal antibodies can be aliquoted and stored at −80° C. The antibodies can be further purified by affinity chromatography for CTLA-4 using routine techniques.

To determine if the selected human anti-CTLA-4 monoclonal antibodies bind to unique epitopes, each antibody can be biotinylated using commercially available reagents (e.g., Pierce, Rockford, Ill.). Competition studies using unlabeled monoclonal antibodies and biotinylated monoclonal antibodies can be performed using CTLA-4 coated-ELISA plates as described above. Biotinylated MAb binding can be detected with a strep-avidin-alkaline phosphatase probe.

To demonstrate binding of monoclonal antibodies to live cells expressing the CTLA4, flow cytometry can be used. For example, cell lines expressing CTLA-4 (grown under standard growth conditions) may be mixed with various concentrations of monoclonal antibodies in PBS containing 0.1% BSA and 10% fetal calf serum, and incubated at 37° C. for 1 hour. After washing, the cells may be reacted with Fluorescein-labeled anti-human IgG antibody under the same conditions as the primary antibody staining. The samples can be analyzed by FACScan instrument using light and side scatter properties to gate on single cells. An alternative assay using fluorescence microscopy may be used (in addition to or instead of) the flow cytometry assay. Cells can be stained as described above and examined by fluorescence microscopy.

Anti-CTLA-4 human IgGs can be further tested for reactivity with CTLA-4 antigen by Western blotting. For example, cell extracts from cells expressing CTLA-4 can be prepared and subjected to sodium dodecyl sulfate polyacrylamide gel electrophoresis. After electrophoresis, the separated antigens are transferred to nitrocellulose membranes, blocked with 10% fetal calf serum, and probed with the monoclonal antibodies to be tested. Human IgG binding can be detected using anti-human IgG alkaline phosphatase and developed with BCIP/NBT substrate tablets (e.g., Sigma Chem. Co., St. Louis, Mo.).

In some embodiments, certain structural features of the human anti-CTLA-4 antibodies described herein may be used to create structurally related human anti-CTLA-4 antibodies that retain at least one functional property of the antibodies, such as the capability of binding to CTLA-4. For example, one or more CDR regions of C2, C5 and C15 can be combined recombinantly with known human framework regions and CDRs to create additional, recombinant human anti-CTLA-4 antibodies encompassed herein.

Accordingly, in some embodiments, a method for preparing an anti-CTLA-4 antibody is provided, the method comprising:

preparing an antibody comprising (1) human heavy chain framework regions and human heavy chain CDRs, wherein at least one of the human heavy chain CDRs comprises the amino acid sequence of SEQ ID NOs: 34, 35, and 36; and (2) human light chain framework regions and human light chain CDRs, wherein at least one of the human light chain CDRs comprises the amino acid sequence chosen from SEQ ID NOs: 25, 26, and 27; wherein the antibody specifically binds to CTLA-4.

preparing an antibody comprising (1) human heavy chain framework regions and human heavy chain CDRs, wherein at least one of the human heavy chain CDRs comprises the amino acid sequence of SEQ ID NOs: 37, 38, and 39; and (2) human light chain framework regions and human light chain CDRs, wherein at least one of the human light chain CDRs comprises the amino acid sequence chosen from SEQ ID NOs: 28, 29, and 30; wherein the antibody specifically binds to CTLA-4.

preparing an antibody comprising (1) human heavy chain framework regions and human heavy chain CDRs, wherein at least one of the human heavy chain CDRs comprises the amino acid sequence of SEQ ID NOs: 40, 41, and 42; and (2) human light chain framework regions and human light chain CDRs, wherein at least one of the human light chain CDRs comprises the amino acid sequence chosen from SEQ ID NOs: 31, 32, and 33; wherein the antibody specifically binds to CTLA-4.

In some embodiments, the recombinant antibodies as prepared above may comprise (1) human heavy chain variable region comprising three CDRs: $V_H$ CDR1 of SEQ ID NO: 34, $V_H$ CDR2 of SEQ ID NO: 35, and $V_H$ CDR3 of SEQ ID NO: 36; and (2) human a light chain variable region comprising three CDRs: $V_L$ CDR1 of SEQ ID NO: 25, $V_L$ CDR2 of SEQ ID NO: 26, and $V_L$ CDR3 of SEQ ID NO: 27.

In some embodiments, the recombinant antibodies as prepared above may comprise (1) human heavy chain variable region comprising three CDRs: $V_H$ CDR1 of SEQ ID NO: 37, $V_H$ CDR2 of SEQ ID NO: 38, and $V_H$ CDR3 of SEQ ID NO: 39; and (2) human light chain variable region comprising three CDRs: $V_L$ CDR1 of SEQ ID NO: 28, $V_L$ CDR2 of SEQ ID NO: 29, and $V_L$ CDR3 of SEQ ID NO: 30.

In some embodiments, the recombinant antibodies as prepared above may comprise (1) human heavy chain variable region comprising three CDRs: $V_H$ CDR1 of SEQ ID NO: 40, $V_H$ CDR2 of SEQ ID NO: 41, and $V_H$CDR3 of SEQ ID NO: 42; and (2) human light chain variable region comprising three CDRs: $V_L$ CDR1 of SEQ ID NO: 31, $V_L$ CDR2 of SEQ ID NO: 32, and $V_L$ CDR3 of SEQ ID NO: 33.

In some embodiments, the recombinant antibodies as prepared above may be a single-chain Fv (scFv) comprising a heavy chain variable region comprising the amino acid sequence as set forth in SEQ ID NO: 8, and a light chain variable region comprising the amino acid sequence as set forth in SEQ ID NO:2.

In some embodiments, the recombinant antibodies have non-human framework regions (e.g., mouse).

In some embodiments, the recombinant antibodies as prepared above may be a scFv comprising a heavy chain variable region comprising the amino acid sequence as set forth in SEQ ID NO: 10, and a light chain variable region comprising the amino acid sequence as set forth in SEQ ID NO: 4.

In some embodiments, the recombinant antibodies as prepared above may be a scFv comprising a heavy chain variable region comprising the amino acid sequence as set forth in SEQ ID NO: 12, and a light chain variable region comprising the amino acid sequence as set forth in SEQ ID NO: 6.

In some embodiments, the scFv may optionally further comprise a flexible peptide linker between the heavy chain variable region and the light chain variable region. The peptide linker preferably consists of 1-15 amino acids and more preferably consists of 3-10 amino acids; the preferred sequence of the peptide linker is GSGGGGS (SEQ ID NO: 73).

The nucleotide and polypeptide sequences of the antibodies according to some embodiments are provided below. The amino acid and nucleotide sequences of the parental, or first screen, antibodies are provided in Table A and Table B, respectfully.

TABLE A

Amino Acid Sequences of Heavy and Light Chain Variable Regions of Anti-CTLA-4 scFv Antibodies (Underlined and bolded are the CDRs)

C2 VH, SEQ ID NO: 8
QVQLVQSGGGVVQPGRSLRLSCAASGFTFSSYGMHWVRQAPGKGLEW
VAVIWYDGSRQYYADSVKGRFTISRDDSKNTMYLQMNSLRAEDTAVY
YCARGGFWGAFDIWGQGTMVTVSS

TABLE A-continued

Amino Acid Sequences of Heavy and Light Chain
Variable Regions of Anti-CTLA-4 scFv Antibodies
(Underlined and bolded are the CDRs)

C2 VL, SEQ ID NO: 2
DVVMTQSPGTLSLSPGEGATLSCRASQHVISSYLAWYQQKPGQAPRL
LVYGASSRDTGVSDRFTGSGSGTDFTLTISRLEPEDSAVYFC**QQYGT
SPWTF**GQGTKLEIKR

C5 VH, SEQ ID NO: 10
QVQLVQSGAEVKKPGASVKVSCKASGFSFPNYYMHWVRQAPGQGLEW
MGIISPTGGSRTYAQKFQGRVTITRDTSTSTVYMELSSLRSEDTAVY
YCAREMYNWNGGWDYGMDVWGQGTLVTVSS

C5 VL, SEQ ID NO: 4
QSALTQSASVSGFPGQSITVSCVGTNSDVEAYDLVSWYRQHPDKSPN
LLIYDNYKRPSGVSDRFSAFKSGNTASLTISGLQAEDEAYYYC**CSYA
GFSTWIF**GAGTQLTVLG

C15 VH, SEQ ID NO: 12
QVQLVQSGAEVKKPGSSVKVSCKASGGTFSSYAISWVRQAPGQGLEW
MGGIIPIFGTANYAQKFQGRVTITADESTSTAYMELSSLRSEDTAVY
YCARDTAMALFYYYYGMDVWGQGTLVTVSS

C15 VL, SEQ ID NO: 6
QSALTQPASVSGSPGQSTTISCTGTSSDVGGYNYVSWYQQHPGKAPK
LMIYEVSNRPSGVSNRFSGSKSGNTASLTISGLQAEDEADYYC**SSYR
SSGTPYVF**GTGTKLTVLG

TABLE B

Nucleotide Sequences of Heavy and Light Chain
Variable Regions of Anti-CTLA-4 scFv Antibodies C2 VH, SEQ ID NO: 7
CAGGTCCAGCTGGTGCAGTCTGGGGGAGGCGTGGTCCAGCCTGGG
AGGTCCCTGAGACTCTCCTGTGCAGCGTCTGGATTCACCTTCAGT
AGCTATGGCATGCACTGGGTCCGCCAGGCTCCAGGCAAGGGGCTG
GAGTGGGTGGCA**GTTATATGGTATGATGGAAGTAGGCAATATTAT
GCTGACTCC**GTGAAGGGCCGATTCACCATCTCCAGAGACGATTCC
AAGAACACGATGTATCTGCAAATGAACAGCGTGAGAGCCGAAGAC
ACGGCTGTTTATTACTGTGCGAGA**GGGGGATTTTGGGGGCTTTT
GATATC**TGGGGCCAAGGGACAATGGTCACCGTCTCCTCA C2 VL, SEQ ID NO: 1
GATGTTGTGATGACTCAGTCTCCAGGCACC
CTGTCTTTGTCTCCAGGGGAAGGAGCCACACTCTCCTGC**AGGGCC
AGTCAACATGTTATCAGCAGCTACTTAGCC**TGGTATCAGCAAAAA
CCTGGCCAGGCTCCCAGGCTCCTCGTCTAC**GGTGCATCCAGTAGG
GACACT**GGCGTCTCAGACAGGTTCACTGGCAGTGGGTCTGGGACA
GACTTCACTCTCACCATCAGCAGACTGGAGCCTGAAGATTCTGCG
GTGTATTTCTGTCAGCAGTATGGTACATCACCGTGGACGTTCGGC
CAAGGGACCAAGCTGGAGATCAAACGT C5 VH, SEQ ID NO: 9
CAGGTGCAGCTGGTGCAATCTGGGGCTGAG
GTGAAGAAGCCTGGGGCCTCAGTGAAGGTTTCCTGCAAGGCATCT
GGATTCAGTTTCCCCAACTACTACATGCACTGGGTGCGACAGGCC
CCTGGACAAGGGCTTGAGTGGATGGGA**ATAATCAGCCCTACCGGT
GGTAGCAGAACGTACGCACAGAAG**TTCCAGGGCAGAGTCACCATA
ACCAGGGACACGTCCACGAGCACAGTCTATATGGAGTTGAGCAGC
CTGAGATCTGAGGACACGGCCGTCTATTAGTGTGCGAGA**GAAATG
TACAACTGGAACGGAGGTTGGGACTACGGTATGGACGTC**TGGGGC
CAAGGAACCCTGGTCACCGTCTCCTCA C5 VL, SEQ ID NO: 3
CAGTCTGCCCTGACTCAGTCTGCCTCCGTGTCT
GGATTTCCTGGACAGTCGATCACCGTCTCCTGC**GTTGGAACCAAC
AGTGATGTTGAGGCTTATGACCTCGTCTCC**TGGTACCGACACAC
CCAGACAAGTCCCCCAACCTCCTAATTTAT**GACAACTATAAGCGA
CCCTCA**GGGGTTTCTGATCGCTTCTCTGCCTTCAAATCTGGAAAC
ACGGCCTCCCTGACCATTTCTGGCCTCCAGGCTGAAGACGAGGCT
TATTATTACTGCTGCTCTTATGCAGGTTTTTCCACCTGGATCTTC
GGCGCGGGGACCCAGCTCACCGTTTTAGGT

TABLE B-continued

Nucleotide Sequences of Heavy and Light Chain
Variable Regions of Anti-CTLA-4 scFv Antibodies C15 VH, SEQ ID NO: 11
CAGGTGCAGCTGGTGCAGTCCGGGGCTGAGGTGAAGAAGC
CTGGGTCCTCGGTGAAGGTCTCCTGCAAGGCTTCTGGAGGCACCT
TCAGCAGCTATGCTATCAGCTGGGTGCGACAGGCCCCTGGACAAG
GGCTTGAGTGGATGGGA**GGGATCATCCCTATCTTTGGTACAGCAA
ACTACGCACAGAAG**TTCCAGGGCAGAGTCACGATTACCGCGGACG
AATCCACGAGCACAGCCTACATGGAGCTGAGCAGCCTGAGATCTG
AGGACACGGCCGTGTATTACTGTGCGAGA**GATACTGCTATGGCAC
TATTCTACTACTACTACGGTATGGACGTC**TGGGGCCAAGGCACCC
TGGTCACCGTCTCCTCA C15 VL, SEQ ID NO: 5
CAGTCTGCCC
TGACTCAGCCTGCCTCCGTGTCTGGGTCTCCTGGACAGTCGACCA
CCATCTCCTGC**ACTGGAACCAGCAGTGACGTTGGTGGTTATAACT
ATGTCTCC**TGGTACCAACAGCACCCAGGCAAAGCCCCCAAACTCA
TGATTTATGAGGTCAGTAATCGGCCCTCAGGGGTTTCTAATCGCT
TCTCTGGCTCCAAGTCTGGCAACACGGCCTCCCTGACCATCTCTG
GGCTCCAGGCTGAGGACGAGGCTGATTATTACTGC**AGCTCATATA
GAAGCAGCGGCACTCCTTATGTCTTC**GGAACTGGGACCAAGCTGA
CCGTCCTAGGT

TABLE 1

CDR amino acid sequences of light chain and
heavy chain variable regions
for C2, C5 and C15

CDR sequences of light and heavy chains
for MAbs C2, C5 and C15

| Chain | HuMAb | CDR1 | SEQ ID NO: | CDR2 | SEQ ID NO: | CDR3 | SEQ ID NO: |
|---|---|---|---|---|---|---|---|
| Light chain | C2 | RASQHV ISSYLA | 25 | GASSRDT | 26 | QQYGT SPWTF | 27 |
| | C5 | VGTNSDV EAYDLVS | 28 | DNYKRPS | 29 | CSYAGF STWIF | 30 |
| | C15 | TGTSSDV GGYNYVS | 31 | EVSNRPS | 32 | SSYRSS GTPYVF | 33 |
| Heavy chain | C2 | SYGMH | 34 | VIWYDGS RQYYADS | 35 | GGFWGAFDI | 36 |
| | C5 | NYYMH | 37 | IISPTGG SRTYAQK | 38 | EMYNWNGG WDYGMDV | 39 |
| | C15 | SYAIS | 40 | GIIPIFG TANYAQK | 41 | DTAMALFY YYYGMDV | 42 |

II. Therapeutic Compositions and Methods

Also provided are pharmaceutical compositions comprising at least one human monoclonal antibody and/or human antibody and/or antigen-binding fragment thereof, and a pharmaceutically acceptable carrier as described herein. Some compositions include a combination of multiple (e.g., two or more) isolated human monoclonal antibodies and/or human antibodies described herein. In some embodiments, each of the antibodies of the composition may be a monoclonal antibody or a human antibody that binds to a distinct, pre-selected epitope of human CTLA-4.

The pharmaceutical compositions of the present disclosure have in vitro and in vivo diagnostic and therapeutic utilities. In some embodiments, the present disclosure provides a method of using antibodies described herein for detecting in vitro or in vivo the presence of human CTLA-4 antigen in a sample, e.g., for diagnosing a CTLA-4 associated disease. In some methods, this is achieved by contacting a sample to be tested, along with a control sample, with an antibody of the present disclosure, under conditions that allow for formation of a complex between the antibody and human CTLA4. Complex formation is then detected (e.g., by ELISA) in the test samples, and any statistically significant increase in the formation of complexes between the test and control samples is indicative of human CTLA-4 antigen in the test sample.

The present disclosure also provides a method of inhibiting the ability of CTLA-4 to activate a cell expressing a CTLA-4 peptide by contacting the antibody described herein with the cell. In some embodiments, a method of treating a CTLA4 associated disease in a subject is provided, which comprises administering to the subject a therapeutically effective amount of the pharmaceutical composition described herein. Also in some embodiments, the antibody of the present disclosure can be used for fabrication of a medicament for treating a CTLA-4 associated disease. The CTLA-4 associated disease may include cancer, a cell proliferative disorder, a disease of the central nervous system, a disease of the blood system, an inflammatory disease, an infectious disease, an allergy, or a T-cell related disease. In some embodiments, the CTLA-4 associated disease is a T cell mediated autoimmune disease. In some embodiments, the CTLA-4 associated disease is cancer. Further in some embodiments, the CTLA-associated disease is chosen from melanoma, non-small lung cancer, and prostate cancer.

The present disclosure also provides a method for inducing, augmenting, or prolonging an immune response to an antigen in a patient, comprising administering a therapeutically effective amount of the pharmaceutical composition described herein that blocks binding of human CTLA-4 to human B7 ligands. The antigen described herein can be a tumor antigen or an antigen from a pathogen. The tumor antigen may also include the protein telomerase. Another form of tumor antigen is purified heat shock proteins (HSP) isolated from the tumor tissue itself. These heat shock proteins contain fragments of proteins from the tumor cells and these HSPs are highly efficient at delivery to antigen presenting cells for eliciting tumor immunity (Suot, R & Srivastava, P (1995) *Science* 269: 1585-1588; Tamura, Y. et al. (1997) *Science* 278: 117-120). In some embodiments, the antigen is a Hepatitis B surface antigen.

Dosage regimens are adjusted to provide the optimum desired response (e.g., a therapeutic response). For example, a single bolus may be administered, several divided doses may be administered over time or the dose may be proportionally reduced or increased as indicated by the exigencies of the therapeutic situation. The specification for the dosage unit forms of the disclosure are dictated by and directly dependent on (a) the unique characteristics of the antibody and the particular therapeutic effect to be achieved, and (b) the limitations inherent in the art for the treatment of sensitivity in individuals.

In one embodiment, administration be intravenous, intramuscular, intraperitoneal, or subcutaneous, or administered proximal to the site of the target. If desired, the effective daily dose can be administered as two, three, four, five, six or more sub-doses administered separately at appropriate intervals throughout the day, optionally, in unit dosage forms. While it is possible for the antibody of the present disclosure to be administered alone, it is preferable to administer the compound as a pharmaceutical composition as described herein.

Combination Therapies

One or more additional therapeutic agents can be either incorporated into the pharmaceutical compositions described herein for administering to a subject or co-administered to a subject, for treatment of a CTLA-4 associated disease in the subject.

CTLA4 blockade may be effectively combined with chemotherapeutic regimes. In these instances, it may be possible to reduce the dose of chemotherapeutic reagent administered (Mokyr, M. et al. (1998) *Cancer Research* 58: 5301-5304). In some embodiments, the additional therapeutic agent or agents are chemotherapeutic agents including but are not limited to mitotic inhibitors, alkylating agents, anti-metabolites, intercalating antibiotics, growth factor inhibitors, cell cycle inhibitors, enzymes, topoisomerase inhibitors, biological response modifiers, anti-hormones, angiogenesis inhibitors, and anti-androgens.

In some embodiments, the additional therapeutic agents are antibodies acting as immune checkpoint inhibitors, including but not limited to rituximab, bevacizumab, trastuzumab, anti-IGF 1R antibody (e.g., CP-751,871), anti-CD40 antibody (e.g., CP-870,8930), anti-PD-1 antibody, anti-PD-1 L1 antibody, anti-PD-1 L2 antibody, and the like. In some embodiments, the additional therapeutic agent is a vaccine, including but not limited to a GM-CSF-modified tumor vector vaccine or an antigen-loaded dendrite cell vaccine. Co-administration includes administration of the therapeutic agents in a sequential manner, that is, wherein each therapeutic agent is administered at a different time, as well as administration of these therapeutic agents, or at least two of the therapeutic agents, concurrently. Sequential or concurrent administration of each therapeutic agent can be effected by any appropriate route including, but not limited to, oral routes, intravenous routes, intramuscular, subcutaneous routes, and direct absorption through mucous membrane tissues. The therapeutic agents can be administered by the same route or by different routes. For example, a first therapeutic agent (e.g., a chemotherapeutic agent) can be administered orally, and a second agent (e.g., anti-CTLA4 antibody) can be administered intravenously. Further, a first therapeutic agent of the combination selected may be administered by intravenous injection while the other therapeutic agents of the combination may be administered orally. Alternatively, for example, both the therapeutic agents may be administered by intravenous or subcutaneous injection.

EXAMPLES

The examples discussed below are intended to be purely exemplary of the invention and should not be considered to limit the invention in any way. The examples are not intended to represent that the experiments below are all or the only experiments performed. Efforts have been made to ensure accuracy with respect to numbers used (for example, amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

Example 1

Construction of PIII Phage-Display Library

Synthesis of the Phage-Display Vector. The vector comprising a gene coding for viral coat protein PIII was synthesized (GenScript). The PIII gene is located downstream of polyclonal sites in which antibody variable region genes (both VH and VL genes) would be inserted. An enterokinase cut site is located upstream of the PIII gene and downstream of a his-tag for purification purposes.

Preparation of the cDNA Template. Human Peripheral Blood from eight donors were collected in PAXgene™ Blood RNA Tubes (PAXgene). PBMCs were purified using the Ficoll Hypaque method. Total RNA was prepared from PBMCs using RNeasy® Midi Kit (Qiagen). First strand cDNA was synthesized from total RNA by using a SuperScript® III First-Strand Synthesis kit (Invitrogen) with oligo (dT).

Amplification of Antibody Variable Region Genes. Both the VH and VL gene repertoires were PCR amplified by using the cDNA a as template. To amplify the VH and VL genes from the cDNA and plasmid template, primers were designed based on those previously published and the most recent gene segments entered in the V-Base sequence directory (de Haard (1999) J. Biol. Chem. 274:18218-18230; Haidaris (1999) J. Immunol. Methods 257: 185-202; Welschof (1995) J. Immunol. Methods 179: 203-214; Marks (1991) Eur. J. Immunol. 21:985-991). All primary PCR reactions were carried out with separate backward primers and combined forward primers. For the amplification of the VH gene repertoires, 12 separate PCR reactions were set up by using one of 12 different human VH (HVH) back primers and an equimolar mixture of four human heavy chain J region (HJH) forward primers. For the kappa and lamda VL genes, the same approach was used with 13 separate reactions defined by individual $HV_{kappa}$ or $HV_{lamda}$ back primers and a mixture of $HJ_{kappa}$ or $HJ_{lamda}$ forward primers. PCRs were performed in 100 ul volumes containing 2 ul of cDNA reaction mixture, 2 uM of primer solutions, 200 uM of dNTPs, 5% DMSO, and 10 ul of Pfu polymerase reaction buffer (Stratagene). After 5 min of denaturation at 94° C., 5 units of Pfu polymerase was added, followed by 30 cycles of 1 min at 94° C., 1 min at 57° C., and 1 min at 72° C., and at the end of cycling an incubation of 10 min at 72° C. After PCR, the various reactions afforded VH, $V_{kappa}$, and $V_{lamda}$ subpools from the mixture of 8 different PBL samples which gave three final VH, $V_{kappa}$, and $V_{lamda}$ pools ready for purification and assembly.

Cloning of VH or VL genes into the TA plasmid. The amplified VH and VL genes were gel-purified using QIAquick® Kit (Qiagen) and cloned into a TA vector, separately. Ligation reactions were performed in 400 ul volume (NEB) containing 2 ug of T vector and 3 ug of purified VH fragments or 2.5 ug of T vector and 6 ug of purified VL fragments. The reactions were incubated at 16° C. overnight. The reaction volume was concentrated to 50 ul using a plasmid miniprep column. The ligated products were transformed into XL-1 blue E. Co/i competent cells (transformation efficiency was $8.7 \times 10^8$ cell/ug). Transformation was performed 9 times for each ligation product with each transformation using 5 ul of ligated product and 40 ul of competent cells. The mixture of ligation product and competent cells was electroporated at 25 μFD, 200Ω, 2.5 kV using Xcell™ (Bio-Rad). When each electroporation was done, cells were harvested in LB medium and combined. The final volume of transformed cells was 15 ml. To calculate the size of T vector library of VH or VL, 10 ul of transformed cells were distributed evenly on a LB plate and cultured at 37° C. overnight. Colonies were counted and the size of the T vector library was calculated: $1.62 \times 10^7$ for $V_H$ genes, $1.86 \times 10^7$ for VL genes. All 15 ml of transformed cells were plated on 10 150-mm LB/agar plates and incubated at 37° C. overnight. Cells from plates were harvest using total 320 LB medium and 20 ml was aliquoted in 16 50-ml falcon tubes and stored at –80° C. freezer.

Construction of the scFv Library. 20 ml of each T vector library of VH genes and VL genes was thawed and spun down to obtain cells. VH and VL genes-containing T vectors were purified using HighPure Midi plasmid purification kit (TianGen). The purified plasmid was double digested with NcoI-HF/XhoI-HF (both from NEB) for VH genes or with NheI-HF and NotI-HF (both from NEB) for VL genes as follows: in total 750 ul reaction volume, 120 ug of above purified VII or VL genes-containing T plasmid, and 600 U NcoI-HF and 900 U XhoI-HF or 600 U NhetI-HF and 900 U NotI-HF were added. The reaction was performed at 37° C. overnight. After the digestion reaction was done, the digested plasmid was precipitated in ethanol, dissolved in 40 ul TE buffer and the insert of VH or VL genes was gel-purified. Linearized phage-vectors digested with NcoI/XhoI for VH genes or NheI-HF and NotI-HF for VL genes were prepared using the same method. VH genes were cloned between NcoI/XhoI sites, and $V_{kappa}/V_{lamda}$ genes were cloned between NheI/NotI sites, such that both VH and VL genes were in frame with a PIII coat protein coding sequence in the phage display vector. VH and VL genes were cloned into the phage-display vector in two steps. The VL genes were cloned into the vector first. The ligation reaction was performed in 900 ul volume containing 5.5 ug of the linearized vector, 3.5 ug of the VL genes insert and 10,000 U of $T_4$ ligase (NEB) at 16° C. overnight.

The ligated products were purified in mini columns and eluted in 200 ul TE buffer and were electroporated into E. Coli XL-1 blue competent cells. The electroporation were done 40 times with each 5 ul of the ligated product and 40 ul of competent cells, which yielded a diversity of total about $5.3 \times 10^8$ independent transformants. After electroporation, cells were plated on LB agar containing 2% glucose, 50 ug/ml carbenicillin, and 20 ug/ml tetracycline in 40 dishes (150 mm×10 mm; Nunc) and incubated overnight at 37° C. The clones were scraped off the plates into 1600 ml of superbroth (SB) medium with 10% glycerol and aliquot and stored at –70° C. The VL genes-containing phage vector was purified and linearized plasmid by digestion with NheI-HF and NotI-HF was gel-purified. The ligation with VII genes was performed in the same way as VL genes ligation.

Example 2

Panning and Obtaining scFv Sequences Targeting CTLA-4 Extracellular Ig-V Domain Antigen. Recombinant human CTLA-4-Fc fusion protein was purchased from R&D Systems (Catalog number 352-CTY/CF). CTLA4 sequence from amino acid 37 to 162 was fused to immunoglobulin gamma I Fc region. The recombinant human CTLA-4-Fc fusion protein is then expressed in cultured insect cells and purified using an immobilized protein A column (Repligen Corporation).

Preparation of the PIII Phage Library. 1 L of SB medium containing 2% glucose, 50 ug/ml carbenicillin and 20 ug/ml tetracycline was inoculated overnight with about $5 \times 10^{10}$ cells from the above mentioned PIII library glycerol stock. The culture was shaken at 37° C. until OD600 of about 0.5-0.7 was obtained. Then, about $4 \times 10^{13}$ plaque forming units of helper phage VCSM13 and 2 ml of 0.5 M isopropylbeta-D-thiogalactopyranoside (IPTG) were added. After 30-min incubation at room temperature, the culture was diluted into 5 liters of SB medium containing 50 ug/ml carbenicillin, 20 ug/ml tetracycline, and 0.5 mM IPTG and grown for 2 h at 30° C. Kanamycin was then added to a final concentration of 70 ug/ml, and the culture was grown overnight at 30° C. On next day, the culture was spun down at a speed of 3000 g, 15 mins, 4° C., and bacteria pellets were discarded. The supernatant was transferred to clean, 500 ml centrifuge bottles, and PEG8000 (4% w/v) and NaCl (3% w/v) were added to precipitate ScFv-phage. The phage pellet was resuspended in PBS (10 mM phosphate/150 mM NaCl, pH 7.4) supplied with 2% skimmed milk or 2% BSA.

Panning. 1 ml CTLA-4 Extracellular Ig-V Domain obtained/prepared as described above was solubilized in PBS and incubated with immunotubes (Maxisorb, Nunc) overnight at room temperature. The protein concentration was 50 ug/ml for the first round panning, 10 ug/ml and 5 ug/ml for the second and third round panning, respectively. The immunotubes were blocked with PBS supplied with 4% skimmed milk (Blotto) for 1 h at room temperature. And then about $10^{13}$ cfu scFv-phages were added. After 2 h of incubation with rocking at room temperature, the unbound and nonspecifically bound scFv-phages were eluted by 10 washes of PBS/0.1% Tween-20, and 10 washes of PBS. Specifically bound scFv-phages were eluted with 1 ml elution buffer (100 mM HCl, adjusted to pH 2.2 with solid glycine and containing 0.1% BSA) for 10 min at room temperature. The elute was neutralized with 60 ul of 2 M Tris base, and was subjected to ELISA assay.

ELISA check of scFv-Phage Binding. CTLA-4 Extracellular V Domain (10 ug/ml in PBS) obtained/prepared as described above was coated on a microtiter plate at room temperature overnight, and then with Blotto. Approximately 25 ul soluble scFv-phage was added to each well, and incubated for 1 h at 37° C. After washing, 25 ul of anti-M13 mAb horseradish peroxidase (HRP) conjugate (Amersham Pharmacia) diluted 1:1000 in Blotto was added, and incubated for 30 min at 37° C. Then 50 ul tetramethylbenzidine substrate (Pierce) was added to each well, and the absorbance at 450 nm was checked.

Rescue of scFv-Phage. Positive ScFv-phage pools were used to infect freshly prepared E. coli XL1-Blue cells. The scFv-phages were then rescued, amplified, and subjected to the next round of panning. To rescue the scFv-phage, 10 ml SB (10 ug/ml tetracycline) was inoculated with fresh XL1-Blue cells, and shacked at 250 rpm, 37° C., till OD600=1. 1 ml Sc-Fv phage was added and incubated at 37° C. for 1 hour. Bacteria were spun down, plated on 2YT agar with 50 ug/ml carbenicillin, 20 ug/ml tetracycline and 2% glucose, and incubated at 30° C., overnight. On next day, bacterial cells from the plates were inoculated into 50 ml of SB medium containing 1% glucose, 50 ug/ml carbenicillin, and 10 ug/ml tetracycline (make sure OD600-0.1), and shook at 250 rpm, 37° C. until OD600=0.7. Helper phage VCSM13 was added, and IPTG to a final concentration of 0.25 mM. The culture was incubated at room temperature for 30 mins, diluted into 100 ml of SB medium containing 50 ug/ml carbenicillin, 10 ug/ml tetracycline, and 0.5 mM IPTG, and grown for 2 hours at 30° C. 70 ug/ml kanamycin was added, and the culture was grown overnight (about 16 hours) at 30° C. On next day, amplified phages were precipitated.

Retrieve positive scFv sequences. Once final positive phage pools were identified after several rounds of panning, phages were transduced back into XL1-Blue. XL1_Blue SB culture (10 ug/ml tetracycline) was grown to OD600=1, then phage was added. After incubation at 37° C. for 1 hour, the culture was plated on SB agar with 50 ug/ml carbenicillin, 20 ug/ml tetracycline, 2% glucose, and incubated at 30° C., overnight. On next day, single clones were picked, miniprepped, and sent for sequencing.

Purification of scFvs and Affinity Measurements. Positive scFv genes were subcloned into expression vector pETFlag (derived from pET-15b, Novagen) and transformed into E. coli B834 (Novagen). The scFv expression was induced by growth in super broth containing 0.5 mM isopropyl-thioga-lactoside overnight at 30° C. The Flag-tagged scFvs were purified on anti-Flag M2 affinity agorose (Sigma) from the periplasmic extracts and media. Purified monomeric scFv was prepared by Sephacryl-100 chromatography on FPLC (Amersham Pharmacia) by using PBS buffer. (Mao (1999) PNAS 96:6953-6958)). Dissociation constants (Kd) were calculated from the measured association (kon) and dissociation (koff) rate constants determined by BIAcore instrumentation and software (Amersham Pharmacia) (Medaglia (2002) Protein-Protein Interact. 255-272; Roder (1998) Methods Mol. Med. 13:531-554). In BIAcore experiments, protein antigens were immobilized on CM5 chips. After scFv binding measurements, chips were regenerated with 75 mM HCl (Table 6).

Example 3

Binding of scFv to CTLA-4

Binding to purified recombinant human CTLA-4 Binding of CTLA-4 scFv expressed (sequences shown in FIGS. 3A, 3B, 4A, and 4B) and purified from E. Coli to recombinant human CTLA-4 was shown by ELISA using standard methods and procedures. Microtiter plates coated with purified CTLA4 were incubated with varying concentration of scFv, and then developed with goat anti-human IgG F(ab')$_2$ conjugated to alkaline phosphatase. The data demonstrate dose-dependent, specific binding of all of scFv to CTLA-4 (FIG. 1).

Example 4

Production of Human Full Length Monoclonal Antibodies

Construction of Expression Vectors Full length nucleotide sequences coding for anti-human CTLA-4 MAbs were assembled by overlap PCR from signal peptide gene, VII or VL genes, and IgG gamma 1 constant region or kappa or lambda constant region genes. All of signal peptide gene, IgG gamma 1 constant region or kappa or lambda constant region genes were synthesized (GenScript) and had been cloned into mammalian expression vectors.

In order to construct KD6001-2 full length nucleotide sequence of IgG gamma I heavy chain isotype, the signal peptide gene, VH gene, and IgG gamma I constant region gene were PCR amplified from plasmids containing corresponding sequences by three pairs of primers, CMV promoter and KDP032, KDP034 and KDP035, and KDP020 and BGH reverse primer, respectively (see Table 2 for used primer sequences). The forward primer sequence of KDP034 for $V_H$ gene was complementary at 5' end 19 nt to the back primer sequence of KDP032 for the signal peptide gene, and the back primer sequence of KDP035 for VH gene was complementary at 5' end 21 nt to the forward primer sequence of KDP020 for the IgG gamma I constant region gene, so that the short regions of complementarity built into the ends of VH gene promoted hybridization of the various fragments. The three amplified genes were gel-purified on agarose. Approximately 20 ng of each of three genes were linked by gradient PCR using outer primers CMV promoter and BGH reverse sequence. Gradient PCRs were performed in 10 ul volumes for each annealing temperature reaction containing 2 uM of primer solutions, 200 uM of dNTPs and 0.1 ul of Pfx polymerase reaction buffer (Invitrogen). An initial denaturation step for 5 min at 94° C. was followed by 30 cycles of 1 min at 94° C., 1 min at 8 various temperatures ranging from 45° C. to 60° C., and 1.5 min at 68° C., and at the end of cycling an incubation of 7 min at 68° C. After PCR, products were examined on agarose and right DNA fragments were gel-purified. The purified DNA fragment was digested with NotI and XbaI, agarose gel-purified, and ligated into the mammalian expression vector that had been cut with the same restriction enzymes. The ligated products were transformed into *E. coli* XL1-Blue competent cells and transformed cells were plated on LB/agar plates containing 100 ug/ml Ampicillin. The plates were cultured at 37° C. overnight. PCR were performed directly on *E. coli* colonies using CMV promoter and BGH reverse sequence to obtain positive clones. 3 positive colonies were picked up, inoculated into 3 ml LB, and cultured at 37° C. overnight. Plasmids were purified from 1.5 ml LB culture using Miniprep kit (Qiagen, Germany). The sequence was confirmed by sequencing using CMV promoter and BGH reverse sequence (FIG. 8).

TABLE 2

Primer sequences used for vector construction of C2 mAb heavy chain

| Signal peptide gene | CMV promoter | CGCAAATGGGCGGTAGGCGTG (SEQ ID NO: 43) |
|---|---|---|
| | KDP032 | GCCGGTGGCGGTGGCCACC (SEQ ID NO: 44) |
| VH gene | KDP034 | GGTGGCCACCGCCACCGGCCA GGTCCAGCTGGTGCAGTC (SEQ ID NO: 45) |
| | KDP035 | GCTAGGCCCCTTTGTTGATGC TGAGGAGACGGTGACCATTG (SEQ ID NO: 46) |
| IgG gamma I constant region gene | KDP020 | GCATCAACAAAGGGGCCTAGC (SEQ ID NO: 47) |
| | BGH reverse | AACTAGAAGGCACAGTCGAGGC (SEQ ID NO: 48) |

The same approach was used to construct KD6001-5 and KD6001-15 full length nucleotide sequence of IgG gamma I heavy chain (FIGS. 9 and 10). For VH genes PCR amplified, primers KDP038 and KDP039 were used for KD5001-5 VH gene, primers KDP042 and KDP039 were used for KD5001-15 VII gene (see Table 3 for primer sequences). The signal peptide gene and IgG gamma I constant region gene were the same as those used for KD6001-2 IgG gamma I construction. A

TABLE 3

Primer sequences used for vector construction of C5 and C15 mAb heavy chains

| KD6001-5 VH gene | KDP038 | GGTGGCCACCGCCACCGGCCAGG TGCAGCTGGTGCAATC (SEQ ID NO: 49) |
|---|---|---|
| | KDP039 | GCTAGGCCCCTTTGTTGATGCTG AGGAGACGGTGACCAGG (SEQ ID NO: 50) |
| KD6001-15 VH gene | KDP042 | GGTGGCCACCGCCACCGGCCAGG TGCAGCTGGTGCAGTC (SEQ ID NO: 51) |
| | KDP039 | GCTAGGCCCCTTTGTTGATGCTG AGGAGACGGTGACCAGG (SEQ ID NO: 50) |

In order to construct KD6001-2 full length nucleotide sequence of kappa light chain isotype, the signal peptide gene, VL gene, and kappa constant region gene were PCR amplified from plasmids containing corresponding sequences by three pairs of primers, CMV promoter and KDP032, KDP036 and KDP037, and KDP010 and BGH reverse primer, respectively (see Table 4 for used primer sequences). The forward primer sequence of KDP036 for VL gene was complementary at 5' end 19 nt to the back primer sequence of KDP032 for the signal peptide gene, and the back primer sequence of KDP037 for VL gene was complementary at 5' end 21 nt to the forward primer sequence of KDP010 for the kappa constant region gene, so that the short regions of complementarity built into the ends of VL gene promoted hybridization of the various fragments. The three amplified genes were gel-purified on agarose. Approximately 20 ng of each of three genes were linked by gradient PCR using outer primers CMV promoter and BGH reverse sequence. Gradient PCRs were performed in 10 ul volumes for each annealing temperature reaction containing 2 uM of primer solutions, 200 uM of dNTPs and 0.1 ul of Pfx polymerase reaction buffer (Invitrogen). An initial denaturation step for 5 min at 94° C. was followed by 30 cycles of 1 min at 94° C., 1 min at 8 various temperatures ranging from 45° C. to 60° C., and 1 min at 68° C., and at the end of cycling an incubation of 7 min at 68° C. After PCR, products were examined on agarose and right DNA fragments were gel-purified. The purified DNA fragment was digested with NotI and XbaI, agarose gel-purified, and ligated into the mammalian expression vector that had been cut with the same restriction enzymes. The ligated products were transformed into *E. coli* XL1-Blue competent cells and transformed cells were plated on LB/agar plates containing 100 ug/ml Ampicillin. The plates were cultured at 37° C. overnight. PCR were performed directly on *E. coli* colonies using CMV promoter and BGH reverse sequence to obtain positive clones. 3 positive colonies were picked up, inoculated into 3 ml LB, and cultured at 37° C. overnight. Plasmids were purified from 1.5 ml LB culture using Miniprep kit (TianGen Corp., China). The sequence was confirmed by sequencing using CMV promoter and BGH reverse sequence.

TABLE 4

Primer sequences used for vector construction of C2 mAb light chain

| C2 VL gene | KDP036 | GGTGGCCACCGCCACCGGCGAT GTTGTGATGACTCAGTC (SEQ ID NO: 52) |
|---|---|---|
| | KDP037 | GACAGATGGAGCGGCCACAGTA CGTTTGATCTCCAGCTTGG (SEQ ID NO: 53) |
| kappa constant region gene | KDP010 | ACTGTGGCCGCTCCATCTGTC (SEQ ID NO: 24) |
| | BGH reverse | AACTAGAAGGCACAGTCGAGGC (SEQ ID NO: 48) |

To construct KD6001-5 and KD6001-15 full length nucleotide sequences of lambda constant region isotype, lambda constant region gene was PCR amplified from the plasmid containing the lambda constant region gene using primers KDP108 and M13F (−21) sequence. For VL genes PCR amplified, primers KDP040 and KDP106 were used for KD5001-5 VL gene, primers KDP043 and KDP107 were used for KD5001-15 VL gene (see Table 5 for primer sequences). The signal peptide gene was the same as that used for KD6001-2 IgG gamma I construction.

TABLE 5

Primer sequences used for vector construction of C5 and C15 mAb light chains

| KD6001-5 VL gene | KDP040 | GGTGGCCACCGCCACCGGCC AGTCTGCCCTGACTCAGTC (SEQ ID NO: 54) |
| --- | --- | --- |
| | KDP106 | GGGTTGGCCTTGGGCTGACC TAAAACGGTGAGCTGG (SEQ ID NO: 55) |
| KD6001-15 VL gene | KDP043 | GGTGGCCACCGCCACCGGCC AGTCTGCCCTGACTCAGC (SEQ ID NO: 56) |
| | KDP107 | GGGTTGGCCTTGGGCTGACC TAGGACGGTCAGCTTGG (SEQ ID NO: 57) |
| lambda constant region gene | KDP108 | GGTCAGCCCAAGGCCAACCC (SEQ ID NO: 58) |
| | M13F (-21) | TGTAAAACGACGGCCAGT (SEQ ID NO: 59) |

Generation of mAb-producing CHO cells The parent CHO DG44 cells (which are dhfr⁻) were cultured in CD DG44 medium containing 8 mM L-glutamine and 5 ug/ml recombinant human insulin (rINS). Stable transfected cells were cultured in OptiCHO medium containing 8 mM L-glutamine, 5 ug/ml rINS and various concentrations of methotrexate (MTX).

The expression vectors for the heavy chains and light chains of mAbs were co-transfected into CHO DG44 cells by electroporation method. Pools of stable transfected clones were made by culturing in the selection medium containing 20 nM of MTX. Then stable pools were further selected with iteratively increasing concentrations of MTX up to 10 uM in order to amplify expression genes. At this stage, single clones were obtained by plating the cells with amplified expression genes at low density in 96-well plates. After an appropriate period of growth, those wells with single clones were screened for mAb production using ELISA with anti-Fc antibodies (Wood et al., 1984. *Nucleic Acids Research* 12:3937). Clones with high levels of mAb-producing were further expanded.

Example 5

Anti-CTLA-4 Full Length mAbs Binding to CTLA-4

Figure 11A:
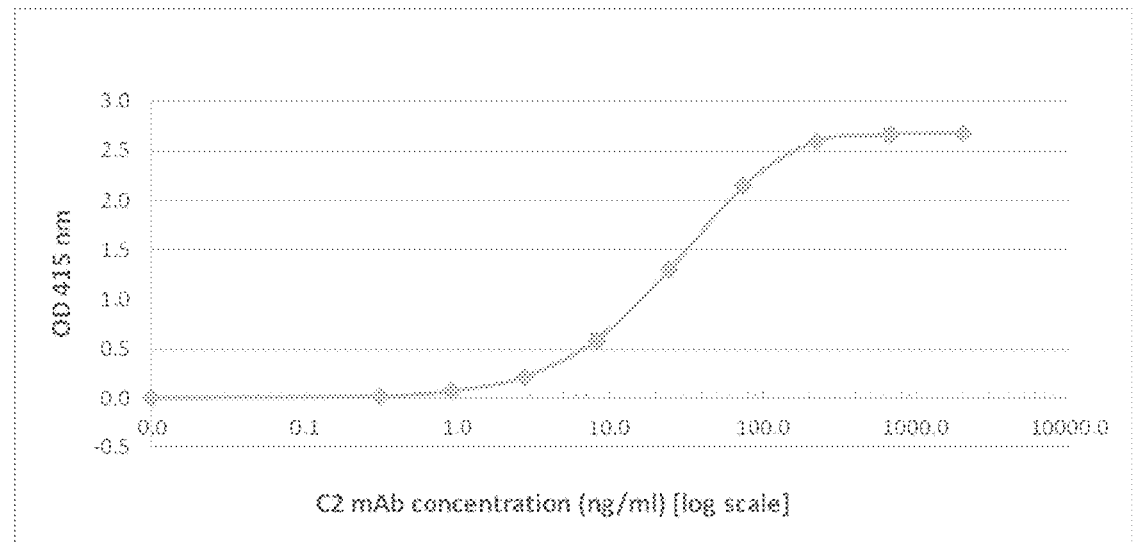
FIG. 11A shows the in vitro binding of the C2 mAb to rhCTLA-4.
Figure 11B:
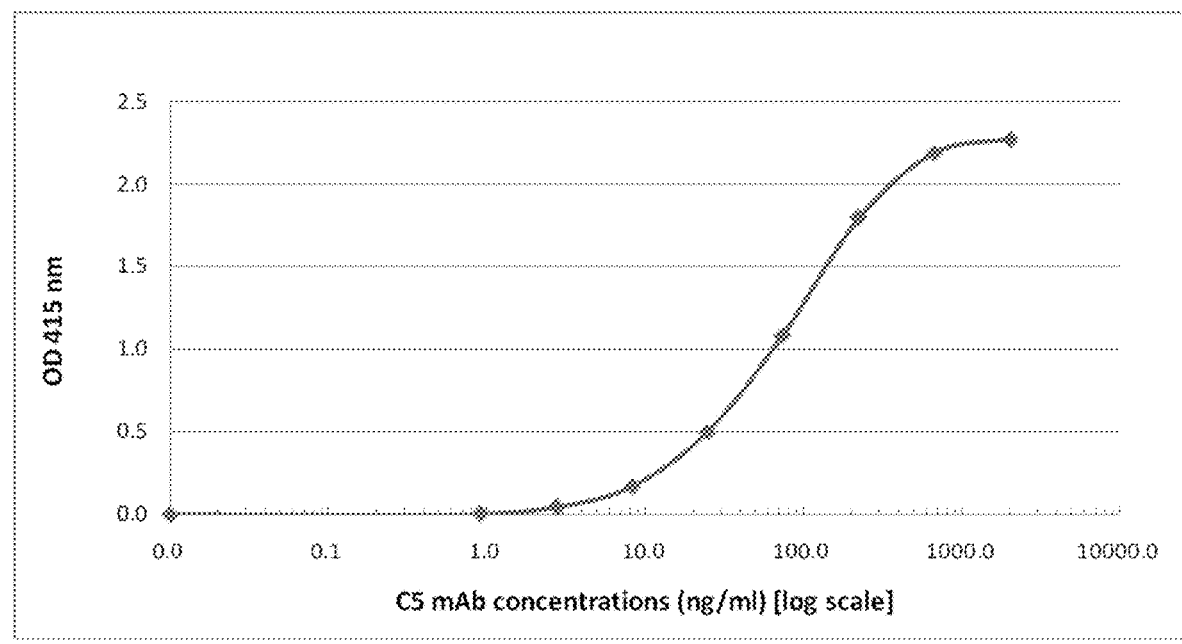
FIG. 11B shows the in vitro binding of the C5 mAb to rhCTLA-4.

Binding to purified recombinant human CTLA-4 (rhCTLA-4) Binding of CTLA-4 mAbs to purified recombinant human CTLA-4 (Purchased from R&D Systems, Catalog number 352-CTY/CF) was shown by ELISA using standard methods and procedures. Microtiter plates coated with purified CTLA4 were incubated with varying concentration of C2 and C5 mAbs, and then developed with goat anti-human IgG F(ab')₂ conjugated to alkaline phosphatase. The data demonstrate dose-dependent binding of C2 (FIG. 11A) and C5 (FIG. 11B) that are well fit to a 4-parameter curve (correlation coefficient is −1.0). The half-maximal binding at 25 ng/ml reflects the high binding capacity of C2 to CTLA-4. C5 has less binding capacity compared to C2 with 66 ng/ml of EC50.

Kinetic analysis of binding to rhCTLA-4. Dissociation constants (Kd) of C2 and C5 mAb were calculated from the measured association (kon) and dissociation (koff) rate constants determined by Fortbio instrumentation and software (Pall Corp) (Table 6). C2 and C5 mAbs were diluted in the binding buffer to 20 ug/ml and sensors of eight were soaked in the diluted mAb solution for 5 min for antibody capturing. The sensors were then blocked in the blocking solution for 5 min. Recombinant human CTLA-4-Fc protein was two-fold serial diluted in the blocking solution to 7 different concentrations, range from 100 nM to 1.6 nM. Kinetic association assays were started by putting antibody-capturing sensors into above serial diluted CTLA-4-Fc solutions. One sensor was immersed into the blocking solution as negative control. After 5 min binding, all sensors were moved to the blocking solution to start kinetic dissociation assays. Assays were stopped after 7 min. Results were shown in Table 6.

TABLE 6

Kinetic analysis of C2 and C5 mAb binding to rhCTLA-4

| Clones | kon (1/Ms) | koff (1/s) | KD (M) |
| --- | --- | --- | --- |
| C2 | $5.5 \times 10^5$ | $4.8 \times 10^{-4}$ | $8.6 \times 10^{-10}$ |
| C5 | $2.8 \times 10^5$ | $6.1 \times 10^{-4}$ | $2.2 \times 10^{-9}$ |

Example 6

C2 mAb Blocking of B7-1 Ligand Binding to CTLA-4

CTLA-4 inhibits T cell activation by binding to co-activators, CD80 (B7-1) and CD86 (B7-2). To determine if the disclosed mAbs and B7-1 or B7-2 may inhibit each other's binding to CTLA-4, an in vitro assay was conducted to test if C2 mAb was capable of inhibiting the binding of B7-1 to CTLA-4. Ipilimumab (Bristol-Myers Squibb, USA) was used as a positive control.

Figure 12:
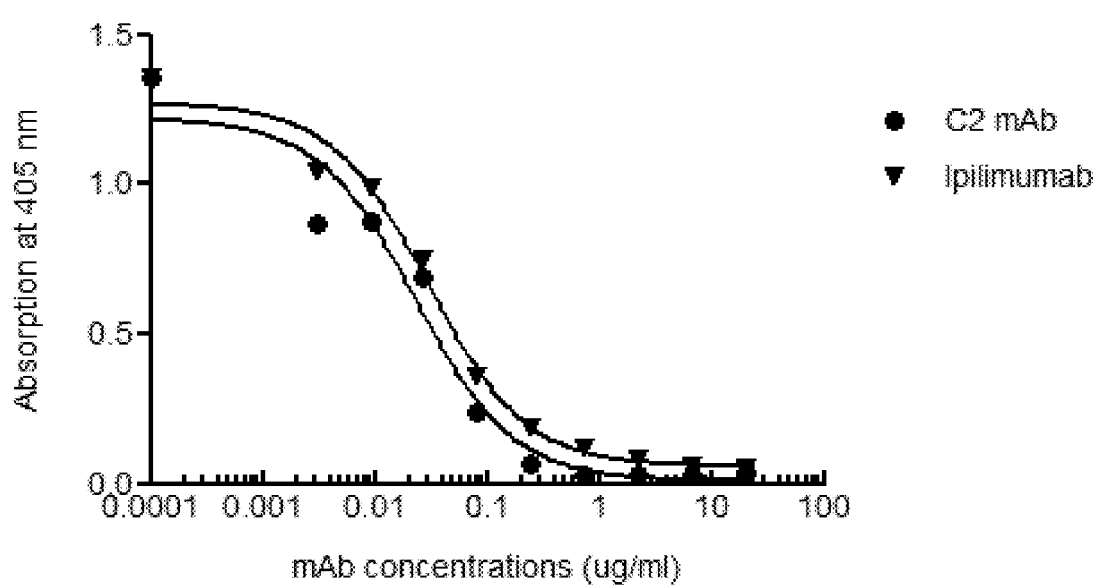
FIG. 12 shows the competitive binding of B7-1 and C2 mAb to rhCTLA-4.

Human recombinant CTLA-4-Fc (2 ug/ml) in 50 ul of 20 mM NaHCO3, pH 9.7 was coated on 96-well plates and incubated at 4° C. overnight. After rhCTLA-4-Fc was removed, the plates were blocked with 100 ul of 3% BSA in wash/dilution buffer (TBS buffer, pH 7.0 containing 0.05% Tween-20) at 37° C. for 2 hours. Human recombinant B7-1-IgG1 Fc fusion protein (R&D Systems Inc., USA) was biotin-labeled using a biotin protein labeling kit (Herochem Inc., China). 10 ng/ml of the biotin-B7-1 fusion protein was mixed with different concentrations of C2 mAb or Ipilimumab in binding buffer (1% BSA in TBST). The mixtures (50 ul/well) were added to rhCTLA-4-Fc coated plates and incubated at 37° C. for 2 hours. The solution was decanted, and the plates were washed 3 times with wash buffer. Alkaline phosphatase conjugated streptavidin (Herochem Inc., China) was diluted 2500-fold in binding buffer and add 50 ul/well to plates. After the plates were incubated at 37° C. for 2 hours, the AP-streptavidin solution was decanted, and the plates were washed 6 times with wash buffer. Alkaline phosphatase substrate pNpp solution was added 50 ul/well to plates. The plates were incubated at 37° C. for 20 min and read at 405 nm using a Bio-Rad microplate reader. Results are shown in FIG. 12. Maximal signal was defined as B7-1 binding in the absence of C2 mAb or Ipilimumab. All samples were tested in duplicate. The results show that C2 mAb and Ipilimumab both can compete efficiently with B7-1 to bind CTLA-4. C2 mAb inhibited B7-1 and CTLA-4 binding more efficiently than Ipilimumab. and inhibited 45-50% binding of B7-1 to CTLA-4 at a molar ratio of 1:1 between C2 mAb and B7-1, indicating that C2 mAb has very high binding affinity to CTLA-4.

Example 7

PBMC IL-2 Production Enhanced by C2 mAb

Upon TI cell activation, the lymphocyte secrets the cytokine interleukin-2 (IL-2). C1LA-4 suppresses T cell activity by decreasing the production of cytokine IL-2. In order to test the function of the antibodies disclosed herein to act as positive regulators of T cell activation, we performed the following experiments to quantify the enhancement of T cell IL-2 production upon CTLA-4 signal blockade with the disclosed antibodies.

Fresh human peripheral blood mononuclear cells (PBMCs) were prepared using Accuspin, and stimulated with various concentration of phytohemagglutnin (PHA) (Sigma). In a 96-well plate PBMC at a concentration of $1\times10^6$ cells/ml were stimulated in 200 ul of RPMI 1640 medium containing L-glutamine, MEM non-essential amino acids, 25 mM Hepes and 10% FBS with 0.1 ug/ml, 1 ug/ml and 10 ug/ml of PHA, respectively. PBMC were cultured at 37° C. for 2 days. The cells were washed and resuspended in the medium to $5\times10^6$ cells/ml. Raji cells (ATCC), a NK-resistent target cell line, was used to measure the intrinsic NK activity of the TL-2. The Raji cells were treated with 25 ug/ml of mitomycin C (Roche) for one hour at 37° C. Raji cells were washed 4 times with the medium and diluted in the medium to $1\times10^6$ cells/ml. PBMC ($5\times10^5$ cells) stimulated with various concentrations of PHA, Raji cells ($1\times10^5$ cells) and C2 mAb at the concentration of 25 ug/ml were added to 96-well culture plates and plates were incubated at 37° C. for 48 hours to 96 hours. Culture supernatants were collected from the plate at the incubation time of 48 hours, 72 hours and 96 hours. Harvested supernatants were frozen for later determination of IL2 amount using standard ELISA methods and procedures.

Figure 13A:
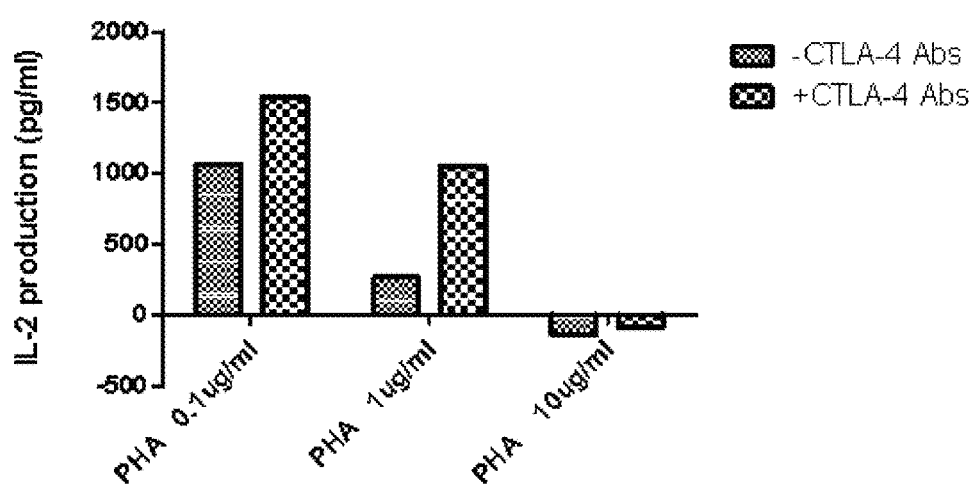
FIGS. 13A and 13B show enhancement of PBMC IL-2 production by C2 mAb. Particularly.
Figure 13B:
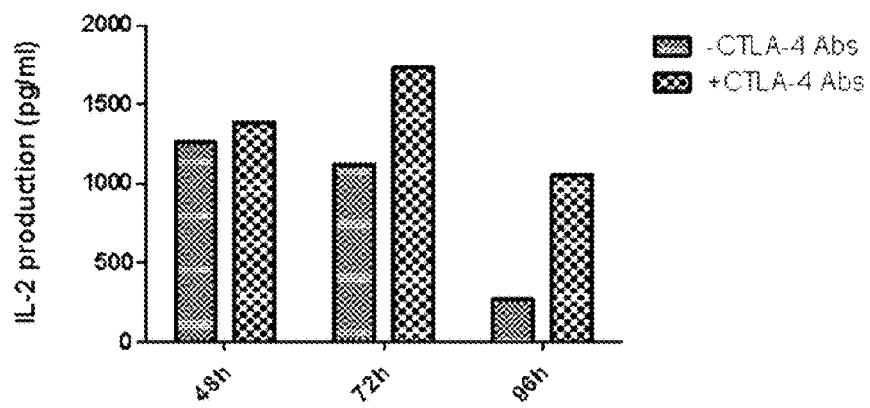

Results from above experiments are shown in FIG. 13. PBMC stimulated with different PHA concentrations were measured for IL-2 production with 72 hour treatment of C2 mAb (Panel A). C2 mAb was able to enhance IL-2 production of PBMC stimulated with PHA at 0.1 ug/ml and 1 ug/ml. No IL-2 was detected from PBMC stimulated with 10 ug/ml of PHA and reason for this could be due to complete IL-2 consumption by fast growing T cells. IL-2 production from 1 ug/ml PHA stimulated PBMC was determined at 48 hours, 72 hours and 96 hours post treatments with C2 mAb (Panel B). Effects of CTLA-4 signal blockade by C2 mAb were observed at 72 hours and 96 hours post treatments of C2 mAb.

Example 8

C2 mAb Binding to rhCTLA-4 Treatment Enhances Antibody Responses to a Hepatitis B Surface Antigen (HBsAg).

Figure 14A:
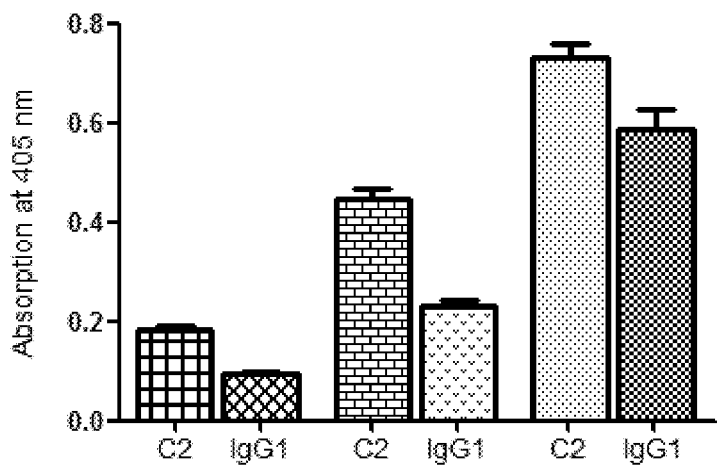
FIG. 14A shows the enhancement of the plasma titer of anti-HBsAg antibody in cynomolgus monkey induced by C2 mAb.
Figure 14B:
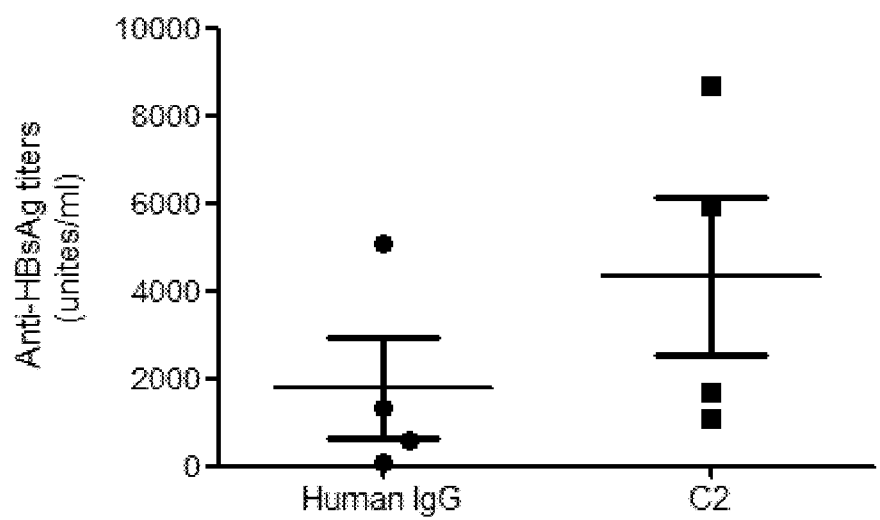
FIG. 14B shows the increase of anti-HBsAg antibody amount in two groups of four monkeys upon C2 mAb administration.

Hepatitis B surface antigen (HBsAg) can immunize primates and generate strong neutralizing antibodies against HBsAg in those primates. CTLA-4 is a negative regulator of such in vivo immune responses. Accordingly, the ability of the C2 mAb disclosed herein to enhance antibody responses to a HBsAg vaccine was examined in cynomolgus monkeys. Two groups of 4 monkeys of each (two males and two females) were administered intravenously with a control human IgG1 (anti-Her2 mAb) or anti-CTLA-4 mAb C2 at a dose of 10 mg/kg on days 1 and 29. Antibodies were prepared at 5 mg/ml in PBS and sterilized using 0.22 um filters. All monkeys were vaccinated intramuscularly with 10 ug/each of HBsAg (Engerix-B, commercially available from GlaxoSmithKline, China) on days 2 and 30. Plasma levels of antibody to HBsAg were measured on days 1, 35 and 49 using standard ELISA methods and procedures. Briefly, HBsAg was diluted in 200 mM NaHCO3 (pH9.6) to 2 ug/ml and was coated on %-well microplates at 4° C. overnight. HBsAg was removed and plates were washed three times with TBST (TBS containing 0.05% Tween-20). Plates were blocked with 100 ul of 3% BSA in TBST at 37° C. for 1 hour. For anti-HBsAg antibody titer assays, plasma mixtures were used. The plasma mixtures were prepared using 5 ul from each monkey in the same group. Mixtures were diluted in binding buffer (1% BSA in TBST) to 100, 500, 2500 and 12500 fold. After blocking buffer was removed, the mixtures were added to 96-well plates and incubated at 37° C. for 2 hours. To compare amounts of anti-HBsAg antibodies, each monkey's plasma was diluted 1000 fold in binding buffer and was added to 96-well plates and incubated at 37° C. for 2 hours. The plasma mixture from day-49 of C2 mAb treated monkeys was used as a standard reference, anti-HBsAg antibody concentration was set at 2500 units/ml. After 2-hour incubation, all plasma was removed and plates were washed 3 times with TBST. 2000-fold diluted goat anti-monkey IgG was added to plates and incubated at 37° C. for 2 hours. Plates were washed 6 times and 50 ul/well of pNpp substrate (Southern Biotech, China) was added and incubated at room temperature, and then plates were read at 405 nm using a microplate reader (Bio-Rad). All samples were tested in duplicate. The titer assay results and amount comparison results were shown in FIGS. 14A and 14B, respectively. Results represent the mean of four monkeys in the same group. These results demonstrate that the C2 mAb disclosed herein is able to enhance in vivo immune response to a viral immunization in primates.

What is claimed is:

1. An isolated human antibody, or an antigen-binding portion thereof, that specifically binds to human CTLA-4, the antibody comprising:
   a heavy chain variable region comprising three complementarity determining regions (CDRs): VHCDR1 of SEQ ID NO: 34, VHCDR2 of SEQ ID NO: 35, and VHCDR3 of SEQ ID NO: 36; and
   a light chain variable region comprising three CDRs: VLCDR1 of SEQ ID NO: 25, VLCDR2 of SEQ ID NO: 26, and VLCDR3 of SEQ ID NO: 27.

2. An isolated human antibody, or an antigen-binding portion thereof, that specifically binds to human CTLA-4, the antibody comprising:
   a heavy chain variable region comprising three CDRs: VHCDR1 of SEQ ID NO: 37, VHCDR2 of SEQ ID NO: 38, and VHCDR3 of SEQ ID NO: 39; and
   a light chain variable region comprising three CDRs: VLCDR1 of SEQ ID NO: 28, VLCDR2 of SEQ ID NO: 29, and VLCDR3 of SEQ ID NO: 30.

3. An isolated human antibody, or an antigen-binding portion thereof, that specifically binds to human CTLA-4, the antibody comprising
   a heavy chain variable region comprising three CDRs: VHCDR1 of SEQ ID NO: 40, VHCDR2 of SEQ ID NO: 41, and VHCDR3 of SEQ ID NO: 42; and
   a light chain variable region comprising three CDRs: VLCDR1 of SEQ ID NO: 31, VLCDR2 of SEQ ID NO: 32, and VLCDR3 of SEQ ID NO: 33.

4. The antibody of claim 1, which is an IgG1 antibody, optionally wherein the antibody is an IgG1,κ or IgG1,λ antibody.

5. The antibody of claim 1, which is a single chain antibody (scFv).

6. The scFv of claim 5, comprising a heavy chain variable region comprising the amino acid sequence as set forth in SEQ ID NO: 8, and a light chain variable region comprising the amino acid sequence asset forth in SEQ ID NO: 2.

7. The antibody of claim 1, wherein the heavy chain variable region comprises:
   (i) the amino acid sequence set forth in SEQ ID NO: 8,
   (ii) an amino acid sequence encoded by a nucleic acid comprising the nucleotide sequence as set forth in or degenerate to SEQ ID NO: 7,
   or
   (iii) an amino acid sequence having at least 90% identity with (i) or (ii).

8. The antibody of claim 1, wherein the light chain variable region comprises:
   (i) the amino acid sequence set forth in SEQ ID NO: 2,
   (ii) an amino acid sequence encoded by a nucleic acid comprising the nucleotide sequence as set forth in or degenerate to SEQ ID NO: 1,
   or
   (iii) an amino acid sequence having at least 90% identity with (i) or (ii).

9. An isolated nucleic acid comprising a nucleotide sequence encoding the amino acid sequence of the antibody of claim 1.

10. A host cell line that produces the antibody of claim 1, wherein the host cell line is a CHO cell line that expresses the isolated nucleic acid of claim 9.

11. The isolated nucleic acid of claim 9 comprising:
(i) the nucleotide sequence set forth in SEQ ID NO: 7,
(ii) a nucleotide sequence having at least 90% identity with (i),
(iii) a nucleotide sequence encoding h antibody heavy chain variable region amino acid sequence set forth in SEQ ID NO: 8, or
(iv) a nucleotide sequence degenerate to (i), (ii) or (iii).

12. The isolated nucleic acid of claim 9 comprising:
(i) h nucleotide sequence set forth in SEQ ID NO: 1,
(ii) a nucleotide sequence having at least 90% identity with (i),
(iii) a nucleotide sequence encoding h antibody light chain variable region amino acid sequence set forth in SEQ ID NO: 2, or
(iv) a nucleotide sequence degenerate to (i), (ii) or (iii).

13. A pharmaceutical composition comprising the antibody of claim 1, and a pharmaceutically acceptable carrier.

14. The pharmaceutical composition according to claim 13, further comprising one or more additional therapeutic agents, optionally wherein the additional therapeutic agent is a chemotherapeutic agent or an immune checkpoint inhibitors.

15. A method of treating a cancer or for stimulating a response to a pathogen in a subject, which comprises administering to the subject a therapeutically effective amount of the pharmaceutical composition of claim 13.

16. The method according to claim 15, further comprising administering to the subject one or more additional therapeutic agents, optionally wherein the additional therapeutic agent is a chemotherapeutic agent, an immune checkpoint inhibitors or a vaccine.

17. The method according to claim 15, wherein the cancer is melanoma, non-small cell lung cancer, or prostate cancer.

18. A method for activating a cell expressing CTLA-4, the method comprising contacting the antibody of claim 1 with the cell.

19. A method for detecting in vitro or in vivo the presence of human CTLA-4 antigen in a sample, the method comprising contacting the sample with the antibody of claim 1.

20. A method for inducing, augmenting or prolonging an immune response to an antigen in a patient, comprising administering a therapeutically effective amount of a pharmaceutical composition of claim 13, wherein the pharmaceutical composition blocks binding of human CTLA-4 to human B7 ligands, optionally wherein the antigen is a tumor antigen, or an antigen from a pathogen.

* * * * *